(12) United States Patent
Veerasamy

(10) Patent No.: US 10,229,364 B2
(45) Date of Patent: *Mar. 12, 2019

(54) MOISTURE SENSOR AND/OR DEFOGGER WITH BAYESIAN IMPROVEMENTS, AND RELATED METHODS

(71) Applicant: Guardian Glass, LLC, Auburn Hills, MI (US)

(72) Inventor: Vijayen S. Veerasamy, Ann Arbor, MI (US)

(73) Assignee: Guardian Glass, LLC, Auburn Hills, MI (US)

( * ) Notice: Subject to any disclaimer, the term of this patent is extended or adjusted under 35 U.S.C. 154(b) by 166 days.

This patent is subject to a terminal disclaimer.

(21) Appl. No.: 15/171,057

(22) Filed: Jun. 2, 2016

(65) Prior Publication Data

US 2016/0275409 A1 Sep. 22, 2016

Related U.S. Application Data

(63) Continuation of application No. 13/543,415, filed on Jul. 6, 2012, now Pat. No. 9,371,032, which is a
(Continued)

(51) Int. Cl.
*B60S 1/08* (2006.01)
*G06N 7/00* (2006.01)
(Continued)

(52) U.S. Cl.
CPC ....... *G06N 7/005* (2013.01); *B32B 17/10036* (2013.01); *B32B 17/10174* (2013.01);
(Continued)

(58) Field of Classification Search
CPC .. B60S 1/0822; B60S 1/0896; B60S 1/08818; B60S 1/0828; G06F 17/18
See application file for complete search history.

(56) References Cited

U.S. PATENT DOCUMENTS 3,682,528 A 8/1972 Apfel et al.
4,782,216 A 11/1988 Woodard
(Continued)

FOREIGN PATENT DOCUMENTS

DE 196 14 100 10/1997
DE 101 39 514 2/2003
(Continued)

OTHER PUBLICATIONS

Fernando Moura-Pires; "Design of a decision tree with action;" Nov. 3, 1991; IEEE/RSJ Internatinoal Workshop on Intelligent Robots and Systems; IEEE Cat. No. 91TH0375-6; pp. 625-630.*
(Continued)

*Primary Examiner* — John Breene
*Assistant Examiner* — Christine Liao
(74) *Attorney, Agent, or Firm* — Nixon & Vanderhye P.C.

(57) ABSTRACT

In certain example embodiments, moisture sensors, defoggers, etc., and/or related methods, are provided. More particularly, certain example embodiments relate to moisture sensors and/or defoggers that may be used in various applications such as, for example, refrigerator/freezer merchandisers, vehicle windows, building windows, etc. When condensation or moisture is detected, an appropriate action may be taken (e.g., actuating windshield wipers, turning on a defroster, triggering the heating of a merchandiser door or window, etc.). Bayesian approaches optionally may be implemented in certain example embodiments in an attempt to improve moisture detection accuracy. For instance, models of various types of disturbances may be developed and, based on live data and a priori information known about the model, a probability of the model being accurate is calculated. If a threshold value is met, the model may be considered a match and, optionally, a corresponding appropriate action may be taken.

11 Claims, 48 Drawing Sheets

Related U.S. Application Data continuation-in-part of application No. 12/076,238, filed on Mar. 14, 2008, now Pat. No. 8,634,988, which is a continuation-in-part of application No. 11/700,251, filed on Jan. 31, 2007, now Pat. No. 7,551,095, and a continuation-in-part of application No. 11/340,847, filed on Jan. 27, 2006, now Pat. No. 7,551,094, and a continuation-in-part of application No. 11/340,864, filed on Jan. 27, 2006, now Pat. No. 7,492,270, and a continuation-in-part of application No. 11/340,859, filed on Jan. 27, 2006, now Pat. No. 7,561,055, which is a continuation-in-part of application No. 11/340,869, filed on Jan. 27, 2006, now Pat. No. 7,516,002.

(60) Provisional application No. 60/757,479, filed on Jan. 10, 2006.

(51) Int. Cl.
| | | |
|---|---|---|
| *B32B 17/10* | (2006.01) | |
| *B60Q 1/14* | (2006.01) | |
| *G01D 5/24* | (2006.01) | |
| *G01J 1/42* | (2006.01) | |
| *G01N 27/22* | (2006.01) | |

(52) U.S. Cl.
CPC ...... *B32B 17/10761* (2013.01); *B60Q 1/1423* (2013.01); *B60S 1/087* (2013.01); *B60S 1/0818* (2013.01); *B60S 1/0822* (2013.01); *B60S 1/0825* (2013.01); *G01D 5/24* (2013.01); *G01J 1/42* (2013.01); *G01N 27/223* (2013.01); *B60Q 2300/112* (2013.01); *B60Q 2300/314* (2013.01)

(56) References Cited

U.S. PATENT DOCUMENTS

| | | | |
|---|---|---|---|
| 5,276,389 A * | 1/1994 | Levers | B60S 1/0818 318/444 |
| 5,998,929 A | 12/1999 | Bechtel et al. | |
| 6,084,285 A | 7/2000 | Shahani et al. | |
| 6,104,349 A | 8/2000 | Cohen | |
| 6,105,336 A | 8/2000 | Katoh et al. | |
| 6,105,461 A | 8/2000 | Bauer et al. | |
| 6,127,977 A | 10/2000 | Cohen | |
| 6,140,975 A | 10/2000 | Cohen | |
| 6,144,022 A | 11/2000 | Tenenbaum et al. | |
| 6,373,263 B1 | 4/2002 | Netzer | |
| 6,379,013 B1 | 4/2002 | Bechtel et al. | |
| 6,552,690 B2 | 4/2003 | Veerasamy | |
| 6,614,241 B2 | 9/2003 | Schmitt et al. | |
| 6,654,070 B1 | 11/2003 | Rofe | |
| 6,686,050 B2 | 2/2004 | Lingle et al. | |
| 6,723,211 B2 | 4/2004 | Lingle et al. | |
| 6,730,352 B2 | 5/2004 | Stachowiak | |
| 6,749,941 B2 | 6/2004 | Lingle | |
| 6,782,718 B2 | 8/2004 | Lingle et al. | |
| 6,802,943 B2 | 10/2004 | Stachowiak | |
| 6,809,530 B2 | 10/2004 | Schmitt et al. | |
| 6,809,692 B2 | 10/2004 | Puente Baliarda et al. | |
| 6,888,465 B2 | 5/2005 | Schmitt et al. | |
| 6,936,347 B2 | 8/2005 | Laird et al. | |
| 6,937,191 B2 | 8/2005 | Puente Baliarda | |
| 6,967,608 B1 | 11/2005 | Maloberti et al. | |
| 6,972,704 B2 | 12/2005 | Rivoir | |
| 6,975,257 B2 | 12/2005 | Reefman et al. | |
| 6,975,277 B2 | 12/2005 | Tran | |
| 6,980,144 B1 | 12/2005 | Maloberti et al. | |
| 7,015,868 B2 | 3/2006 | Puente Baliarde | |
| 7,156,168 B2 | 1/2007 | Gutbrod et al. | |
| 7,198,402 B2 | 4/2007 | Ruettiger | |
| 7,235,767 B2 | 6/2007 | Gutbrod et al. | |
| 7,256,385 B2 | 8/2007 | Rüttiger et al. | |
| 7,325,972 B2 | 2/2008 | Ruettiger | |
| 7,331,531 B2 | 2/2008 | Rüttiger et al. | |
| 7,504,957 B2 | 3/2009 | Veerasamy | |
| 7,830,267 B2 | 11/2010 | Veerasamy | |
| 9,371,032 B2 | 6/2016 | Veerasamy | |
| 2001/0042822 A1 | 11/2001 | Hochstein | |
| 2003/0034926 A1 | 2/2003 | Veerasamy | |
| 2004/0007759 A1 | 1/2004 | Chu et al. | |
| 2004/0019603 A1 | 1/2004 | Haigh et al. | |
| 2004/0051396 A1 | 3/2004 | Supper et al. | |
| 2004/0201483 A1 | 10/2004 | Stam et al. | |
| 2006/0015307 A1 * | 1/2006 | Holschneider | G06F 17/18 703/2 |
| 2007/0044542 A1 | 3/2007 | Barguirdjian et al. | |
| 2007/0157720 A1 | 7/2007 | Veerasamy | |
| 2007/0157721 A1 | 7/2007 | Veerasamy | |
| 2007/0157722 A1 | 7/2007 | Veerasamy | |
| 2007/0162201 A1 | 7/2007 | Veerasamy | |
| 2007/0200718 A1 | 8/2007 | Veerasamy | |
| 2008/0222827 A1 | 9/2008 | Veerasamy | |
| 2008/0223127 A1 | 9/2008 | Schmitt et al. | |
| 2008/0234895 A1 | 9/2008 | Veerasamy | |
| 2009/0206068 A1 | 8/2009 | Ishizeki et al. | |
| 2010/0209730 A1 | 8/2010 | Thomsen et al. | |
| 2011/0212279 A1 | 9/2011 | Lemmer et al. | |
| 2012/0090246 A1 | 4/2012 | Nunez-Regueiro et al. | |
| 2013/0019618 A1 | 1/2013 | Veerasamy et al. | |
| 2013/0024169 A1 | 1/2013 | Veerasamy et al. | |

FOREIGN PATENT DOCUMENTS

| | | |
|---|---|---|
| EP | 1 767 401 | 3/2007 |
| GB | 2 467 649 | 8/2010 |
| WO | WO 01/77763 | 10/2001 |
| WO | WO 2007/009767 | 1/2007 |
| WO | WO 2007/081470 | 7/2007 |
| WO | WO 2008/024639 | 2/2008 |

OTHER PUBLICATIONS

U.S. Appl. No. 13/543,415, filed Jul. 6, 2012; Veerasamy.
"Bayesian Inference in Physics"; Toussaint; 2011 American Physical Society; vol. 83, Jul.-Sep. 2011, pp. 943-999.
"The Impact of Model Based Despeckling on Soil Moisture Estimation", Gleich et al., 2009 IEEE, pp. 1-4.
Lenore Zuck, Amir Pnuell, "Model Checking and Abstraction to the aid of Parameterized Systems", Feb. 18, 2004, Elsevier Ltd., Computer Languages, Systems & Structures 30, 139-169/.
International Search Report dated Sep. 3, 2013.
U.S. Appl. No. 60/757,479, filed Jan. 10, 2006; Veerasamy et al.
European Search Report dated Aug. 10, 2010.
European Search Report dated Aug. 24, 2010.
European Search Report dated Apr. 4, 2011.
European Office Action dated Apr. 7, 2011.

* cited by examiner

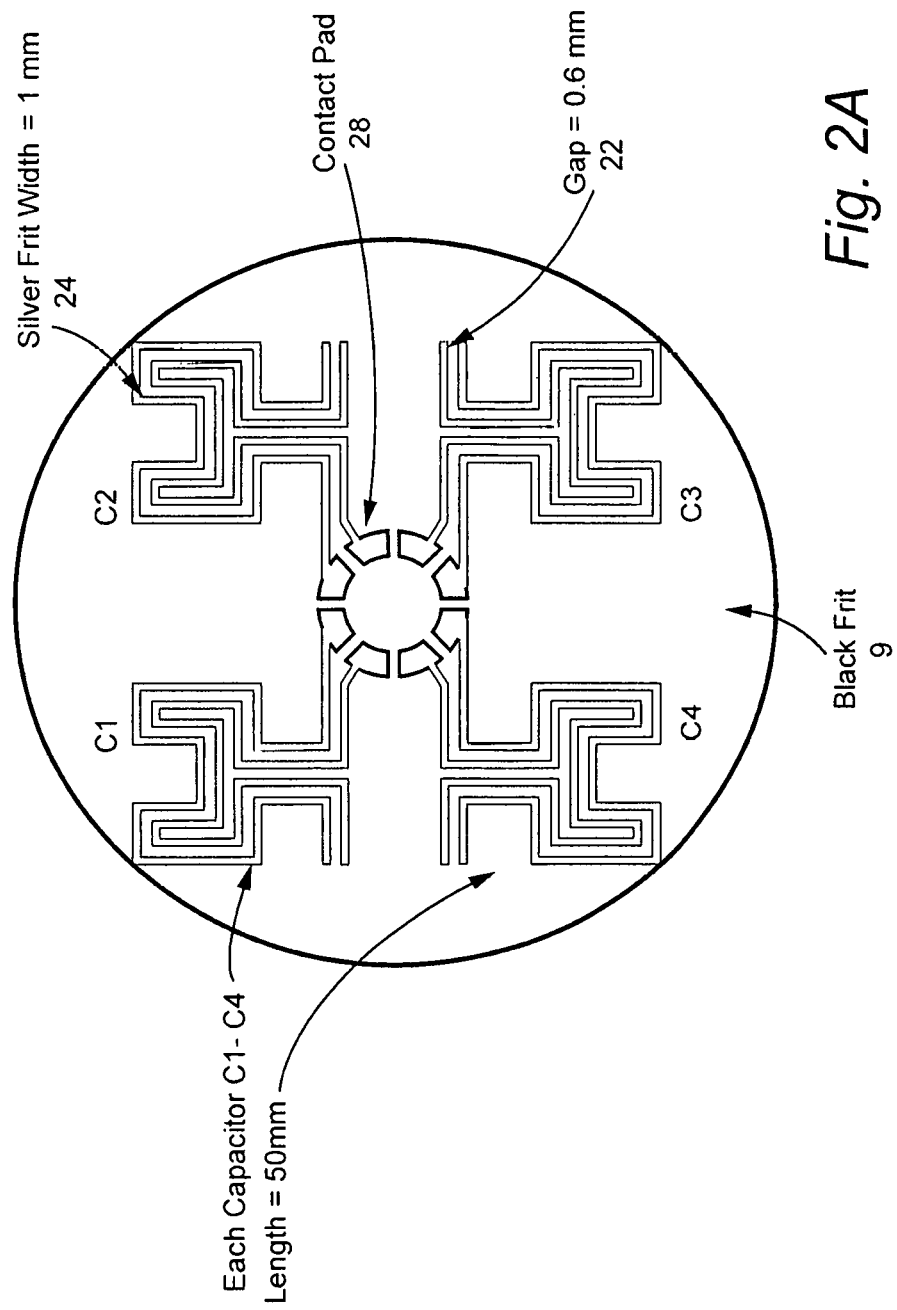

Outer line width = 2mm
Inner line width = 1mm
Air gap = 0.6mm

All units are in mm

Inner circle diameter = 6mm
Outer circle diameter = 13mm
Distance between contact pads = 1mm

|    | C1 | C2 | C3 | C4 |
|----|----|----|----|----|
| C1 | H  | L  | H  | H  |
| C2 | L  | H  | H  | H  |
| C3 | H  | H  | H  | L  |
| C4 | H  | H  | L  | H  |

*Fig. 12A*

|    | C1 | C2 | C3 | C4 |
|----|----|----|----|----|
| C1 | H  | L  | H  | H  |
| C2 | L  | H  | H  | H  |
| C3 | H  | H  | H  | L  |
| C4 | H  | H  | L  | H  |

*Fig. 12B*

|  | Signal | Delta |
|---|---|---|
| No-Disturbance @ 65 F | N1 | 0 |
|  | N2 | 0.8 |
|  | N3 | 0.3 |
|  | N4 | 0.7 |
|  | N5 | 0.3 |
|  |  |  |
| on target water @ 65 F | S1 | 6 |
|  | S2 | 55 |
|  | S3 | 52 |
|  | S4 | 63 |
|  | S5 | 60 |
|  |  |  |
| off target water @ 65 F | F1 | 1 |
|  | F2 | 0.3 |
|  | F3 | 5 |
|  | F4 | 3 |
|  | F5 | 0.6 |
|  |  |  |
| no-disturbance @ 130 F | H1 | 0.3 |
|  | H2 | 0.5 |
|  | H3 | 0.4 |
|  | H4 | 0.7 |
|  |  |  |
| on target water @ 130 F | W1 | 61 |
|  | W2 | 49 |
|  | W3 | 66 |
|  | W4 | 19 |
|  | W5 | 64 |
|  |  |  |
| off target water @ 130 F | K1 | 6 |
|  | K2 | 24 |
|  | K3 | 4.8 |
|  | K4 | 4 |
|  | K5 | 2 |

*Fig. 14*

*Note:* Delta = difference computed between each signal's normalized autocorrelation datapoint and the normalized autocorrelation of a reference (no-disturbance)

1. (S1 & S3)

2. (S2 & S4)

3. (S3 & S2)

4. (S1, S5)

5. (S4 & S1)

1. (W1 & W2)

4. (W4 & W1)

5. (W4 & W5)

2. (W3 & W4)

3. (W2, W5)

```
1:  select initial parameter values: m^(0)
2:  select leapfrog step sizes: ς
3:  FOR k = 1, 2, ... DO
4:      p^(0) ← sample from N(0, 1)
5:      τ ← 0
6:      m̃^(τ) ← m^(k−1)
7:      FOR n = 1, 2, ..., N_leap DO                              {execute leapfrogging}
8:          p^(τ+ς/2) ← p^(τ) − ½ς^T ∇_m U(m̃^(τ))
9:          m̃^(τ+ς) ← m̃^(τ) + ς^T p^(τ+ς/2)
10:         p^(τ+ς) ← p^(τ+ς/2) − ½ς^T ∇_m U(m̃^(τ+ς))
11:         τ ← τ + ς
12:     END FOR                                                    {end leapfrogging}
13:     calculate acceptance probability:
        α ← min (1, exp [H(m^(k−1), p^(0)) − H(m̃^(τ), p^(τ))])
14:     u ← sample from uniform(0, 1)
15:     IF u < α THEN
16:         m^(k) ← m̃^(τ)                                         {accept the sample}
17:     ELSE
18:         m^(k) ← m^(k−1)                                        {reject the sample}
19:     END IF
20: END FOR
```

*Fig. 49*

MOISTURE SENSOR AND/OR DEFOGGER WITH BAYESIAN IMPROVEMENTS, AND RELATED METHODS

CROSS-REFERENCES TO RELATED APPLICATIONS

This application is a continuation of U.S. Ser. No. 13/543,415, filed Jul. 6, 2012, which is a continuation-in-part (CIP) of U.S. Ser. No. 12/076,238, filed Mar. 14, 2008 (now U.S. Pat. No. 8,634,988), which is a CIP of U.S. Ser. No. 11/700,251, filed Jan. 31, 2007(now U.S. Pat. No. 7,551,095), which is a CIP of each of U.S. Ser. No. 11/340,847, filed Jan. 27, 2006 (now U.S. Pat. No. 7,551,094), U.S. Ser. No. 11/340,864, filed Jan. 27, 2006 (now U.S. Pat. No. 7,492,270), U.S. Ser. No. 11/340,859, filed Jan. 27, 2006 (now U.S. Pat. No. 7,561,055), and U.S. Ser. No. 11/340,869, filed Jan. 27, 2006 (now U.S Pat. No. 7,516,002), which claim priority on U.S. Provisional Patent Application No. 60/757,479, filed Jan. 10, 2006, the entire disclosures of which are all hereby incorporated herein by reference.

FIELD OF THE INVENTION

Certain example embodiments relate to moisture sensors and/or defoggers, and/or related methods. More particularly, certain example embodiments relate to moisture sensors and/or defoggers that may be used in various applications such as, for example, refrigerator/freezer merchandisers, vehicle windows, building windows, etc. Bayesian approaches optionally may be implemented in certain example embodiments in an attempt to improve moisture detection accuracy.

BACKGROUND AND SUMMARY OF EXAMPLE EMBODIMENTS OF THE INVENTION

The presence of moisture (e.g., rain or condensation) and/or other material or debris on vehicle windshields and/or backlites may create hazardous driving conditions for drivers, passengers, and pedestrians if not promptly removed. Wiper blades are a well-known, common way to remove such materials and reduce the hazards of driving during dangerous conditions. Rain sensors have been developed to detect the presence of moisture (e.g., rain or other condensation) on a vehicle windshield, and to turn on and off wipers, as necessary, when such moisture is detected. Automatically detecting rain, sleet, fog, and the like, and taking appropriate action—for example, turning on/off wiper blades at a proper speed—potentially reduces distractions to the driver, allowing the driver to better concentrate on the road ahead. However, inappropriately turning on/off wipers or failing to actuate wipers when moisture is present may also create hazardous conditions. Moreover, such systems are also susceptible to "dirt" distractions which may cause false reads/wipes when dirt is on the windshield.

Certain conventional rain sensors are based on an electro-optical concept. According to certain such techniques, rain droplets are sensed solely by measuring the change in the total internal reflection of a light beam off the glass-air interface. Other electro-optical techniques have attempted to analyze the brightness of a section of a window "image" to detect rain droplets or fog on a window. However, these optical techniques have limited sensing areas, are fairly expensive, and may result in erroneous detection indications due to the use of optical imaging as the sole detection method.

Thus, it will be appreciated that there exists a need in the art for a moisture (e.g., rain) sensor that is efficient in operation and/or detection.

In certain example embodiments of this invention, a plurality of sensing capacitors are supported by a window such as a vehicle windshield, the capacitors each having a different field. A sensing circuit outputs an analog signal that is based on and/or related to the capacitances of the sensing capacitors. In certain example embodiments, a switching circuit is provided in order to selectively switch between different sensing capacitors or different combinations thereof (or even possibly antennas and/or bands), in order to change the sensing field being analyzed and/or change the feature being searched for. For example, in certain example embodiments, the switching circuit may selectively switch between: (a) capacitor(s) for detecting rain on an exterior surface of the window, and (b) capacitor(s) for detecting one or more of ice on an exterior surface of the window, mist on an exterior surface of the window, and/or moisture on an interior surface of the window. Such embodiments may or may not be used in combination with any other embodiment(s) of this invention discussed herein.

In certain example embodiments of this invention, there is provided a rain sensor comprising: a sensing circuit comprising a plurality of sensing capacitors supported by a vehicle window, one or more of the sensing capacitors being sensitive to moisture on an external surface of the window and including first and second spaced apart capacitor electrodes that are substantially coplanar; and a switching circuit for selectively coupling the plurality of sensing capacitors to read-out circuitry of the rain sensor.

In other example embodiments of this invention, there is provided an electronic device (e.g., rain sensor, antenna system, or the like) comprising: a sensing circuit comprising a plurality of different fractal structures, and a switching circuit for selectively coupling different ones or combinations of the fractal structures to read-out circuitry. The fractal structures may be capacitive sensors, antennas having different bands, or the like in different example instances.

In certain example embodiments of this invention, there is provided a rain sensor comprising: a sensing circuit comprising at least one sensing capacitor that is sensitive to moisture on an external surface of a window; an adder receiving, directly or indirectly, an analog output signal from the sensing circuit and determining a difference between the analog output signal from the sensing circuit and a feedback signal; a quantizer including a comparator downstream of the adder that outputs a bitstream based at least on whether a received signal level is higher or lower than a predetermined threshold; a lowpass digital filter downstream of the quantizer for lowpass filtering the bitstream so as to output a filtered digital signal; and a correlation engine that performs correlation on the filtered digital signal in order to determine whether rain is present on the external surface of the window. In certain example instances, this system may be said to use sigma-delta modulation in analog to digital signal conversion.

In certain example embodiments of this invention, there is provided a method of determining whether moisture is present on an external surface of a vehicle window, the method comprising: receiving a signal relating to at least one sensing capacitor, and processing the signal to obtain a signal footprint; and comparing the signal footprint with one or more predetermined signal footprints stored in memory to determine whether a detected material on the external surface of the vehicle is moisture or some other material.

In certain example embodiments of this invention, there is provided a rain sensor comprising: at least one sensing capacitor supported by a window, the sensing capacitor being sensitive to rain on an external surface of the window; and wherein the sensing capacitor comprises fractal geometry.

In certain example embodiments of this invention, there is provided a rain sensor comprising: at least one sensing capacitor that is sensitive to moisture on an external surface of a window; and the first sensing capacitor comprising first and second capacitor electrodes each have a meandering shape, and wherein the first and second capacitor electrodes are substantially parallel to each other.

In certain example embodiments of this invention, there is provided a rain sensor comprising: a sensing circuit comprising at least first and second sensing capacitors that are sensitive to moisture on an external surface of a window; the sensing circuit further comprising at least one mimicking capacitor that mimics at least charging and/or discharging of at least one of the first and second sensing capacitors; wherein a writing pulse causes at least the first sensing capacitor to be charged, and an erasing pulse causes each of the first sensing capacitor and the mimicking capacitor to substantially discharge; wherein presence of rain on the external surface of the window in a sensing field of the first sensing capacitor causes a voltage at an output electrode of the mimicking capacitor to fluctuate in a manner proportional to fluctuation of voltage at an output electrode of the first sensing capacitor, even though the rain is not present in a field of the mimicking capacitor; and wherein rain is detected based on an output signal from the output electrode of the mimicking capacitor, wherein the output signal is read at least between an end of the writing pulse and a beginning of the erase pulse.

In other example embodiments of this invention, there is provided a method of detecting rain on a surface of a window, the method comprising: supplying first and second spaced apart writing pulses which respectively cause first and second sensing capacitors of a sensing circuit to charge, wherein the first sensing capacitor charges when the second sensing capacitor is substantially discharged, and the second sensing capacitor charges when the first sensing capacitor is substantially discharged, so that the first and second sensing capacitors are charged at different times; each of the first and second sensing capacitors being sensitive to moisture on the surface of the window; supplying a first erasing pulse, between times of the first and second writing pulses, the first erasing pulse causing the first sensing capacitor to substantially discharge, and supplying a second erasing pulse after the second writing pulse wherein the second erasing pulse causes the second sensing capacitor to substantially discharge; wherein a magnitude of an output of the sensing circuit is affected by presence of rain on the surface of the window; and converting an analog output signal of the sensing circuit to a digital signal and based on the digital signal determining whether rain is present on the surface of the window.

In certain example embodiments of this invention, there is provided a rain sensor comprising: at least one sensing capacitor that is sensitive to moisture on an external surface of a window, the sensing capacitor including a first capacitor electrode that receives a charging signal and a second capacitor electrode spaced apart from the first capacitor electrode; and wherein the second capacitor electrode is floating so that the sensing capacitor is isolated from ground.

The floating characteristic has been found to be advantageous in that it permits false reads due to EMI or external objects (e.g., human hand) to be reduced or prevented.

In certain example embodiments of this invention, there is provided a method of sensing the presence of moisture (e.g., rain, dew, fog, or the like) on a vehicle window, the method comprising: receiving data relating to at least two capacitors supported by the vehicle window; autocorrelating the data relating to each capacitor to obtain autocorrelated data; and determining, based at least on said autocorrelated data, whether moisture is present on an exterior surface of the vehicle window. In certain example embodiments, the data relating to the at least two capacitors is received from circuitry that receives and/or reads capacitance data from the at least two capacitors. In certain example embodiments, the data relating to the at least two capacitors is output from circuitry that: (a) receives and/or reads data and/or signals from the at least two capacitors, and/or (b) includes a capacitor(s) or other circuit element(s) that mimics or substantially mimics charging and/or discharging of the at least two capacitors. In certain example embodiments, the autocorrelation may be used as an initial step to determine whether water may be present on the window. However, it is possible that the autocorrelation may also detect the presence of other materials (e.g., dust or dirt) on the window because the correlation signatures of these materials can be different.

In certain example embodiments of this invention, there is provided a moisture sensor (e.g., rain sensor) for sensing the presence of moisture on a vehicle window, the moisture sensor comprising: one, two or more capacitors; means for autocorrelating data from one, two, three, more, or all of the capacitors to obtain autocorrelated data; and means for determining, based at least on said autocorrelated data, whether moisture is present on the vehicle window.

In certain example embodiments of this invention, cross-correlating data from the at least two capacitors may be performed so as to correlate data from different capacitors to obtain cross-correlated data. Then, based at least on the cross-correlated data, a type and/or amount of moisture may be determined. The cross-correlated data may also or instead be used to determine if the material detected via the autocorrelation is a material other than moisture such as dust or dirt, and if so then not actuating the wipers. In certain example embodiments, the cross-correlating may be performed after the autocorrelating when certain conditions are met. As an example, the cross-correlation may be performed so as to determine whether the moisture on the window is light rain, heavy rain, fog, sleet, snow, or ice (a type of moisture).

In certain example embodiments of this invention, the autocorrelated data from the capacitor(s) may be checked for negative values. When the autocorrelated data has negative value(s), then the system or method may indicate that it is not raining and/or may not actuate windshield wipers.

Moreover, in certain example embodiments, the system or method may calculate whether a gradient of an autocorrelation curve associated with the autocorrelated data is greater than one or some other predetermined value; and if not then the system or method may indicate that it is not raining, park the wipers if they were moving, and/or not actuate wipers of the vehicle.

In certain example embodiments of this invention, the system or method may determine whether the shape of the autocorrelation curve or signal footprint associated with the autocorrelated data is different than a predetermined autocorrelation curve or signal footprint associated with normalized non-disturbed autocorrelation data. When it is not different or substantially different, then it may be indicated that it is not raining, wipers may be parked if they had been moving, and/or wipers may be not actuated. While the footprints are based on autocorrelation data in certain example embodiments of this invention, other types of footprints may instead be used in certain instances.

In certain example embodiments of this invention, conditions checked for in the autocorrelation function include (i) the gradient of the normalized autocorrelation function (e.g., when there is no disturbance the absolute value of the gradient is unity and changes with disturbance), (ii) the sign of the autocorrelation function (e.g., with a CB radio turned on or with a human hand on the windshield the values are oscillatory with positive and negative parts), and (iii) the shape of the autocorrelation function as a function of time lag may also be used as a signature or footprint to distinguish rain from other disturbances, and this shape may also be used to distinguish between different nuances of rain or water content. Thus, in certain example instances, cross-correlating of data from at least two capacitors is only performed when one, two or all of the following conditions are met: (a) the autocorrelated data has no negative values; (b) a gradient of an autocorrelation curve associated with said autocorrelated data is greater than one; and (c) the shape of the autocorrelation curve associated with the autocorrelated data (e.g., signal footprint) is different than a predetermined autocorrelation curve associated with normalized non-disturbed autocorrelation data (e.g., predetermined footprint). Alternatively, (c) may be replaced with (c') the shape of the autocorrelation curve associated with the autocorrelated data (e.g., signal footprint) matches or substantially matches a predetermined autocorrelation curve (e.g., predetermined signal footprint) associated with a known moisture pattern. In certain example embodiments of this invention, a symmetry level of a cross-correlation curve associated with the cross-correlated data can be determined.

In certain example embodiments of this invention, it is possible to compare the autocorrelation between various capacitors. In certain example embodiments of this invention, such a comparison may be used to tell the system whether to initiate a wipe if water is present on the window when the sensor system is turned on.

In certain example embodiments, a sensing capacitor array may include at least n sensing capacitors, wherein n may be two, four, ten or any other suitable number. The array may be any type of array such as a linear array, any of the arrays shown in the figures, or any other type of array. Autocorrelating of data from and/or related to all or less than all of the sensing capacitors may be performed to obtain the autocorrelated data.

In certain example embodiments of this invention, capacitors are formed based on a fractal pattern. For example and without limitation, one or more of the capacitors may be formed based on a fractal pattern, such as a Hilbert fractal pattern. Other capacitive fractal patterns may also be used, including but not limited to a Cantor set. These fractal structures maximize or enlarge the periphery and thus result in a large capacitance for a given area. The use of two dimensional fractal designs also allows the sensor to occupy a small amount of physical space on the window while at the same time being electrically larger than its physical size. The concentration of lateral flux in a fractal geometry may also allow the sensor to detect rain/water not necessarily spread over the actual physical area of the sensor in certain example embodiments of this invention. Furthermore, in its higher iteration(s) a fractal capacitor(s) has an attribute of being its own Faraday shield or quasi-Faraday shield. Also, in certain example embodiments, the rain sensor may be electrically connected to a Local Interconnect Bus of the vehicle.

In certain example embodiments of this invention, there is provided a method of sensing the presence of moisture on a vehicle window such as a windshield, backlite or sunroof, the method comprising: receiving data from at least two capacitors supported by the vehicle window; correlating data from one or more of the capacitors to obtain correlated data; determining, based at least on said correlated data, (a) whether moisture is present on an exterior surface of the vehicle window, and/or (b) a type and/or amount of material present on an exterior surface of the vehicle window. For example and without limitation, the correlation may be autocorrelation and/or cross-correlation.

In certain example embodiments of this invention, there is provided a method of engaging vehicle windshield wiper(s) in response to detected rain, the method comprising reading data from a capacitive array having at least two capacitors; autocorrelating data from each capacitor individually; determining from the autocorrelation data whether it is raining; cross-correlating data from the capacitors; determining from the cross-correlated data a type and/or an amount of rain; engaging the wipers if rain is detected; and, stopping or not actuating the wipers if one or both of the determining steps determines that it is not raining. In certain example embodiments, a symmetry level of the cross-correlation curve may be determined, and a wiper speed related to the symmetry level may be selected. A wiper speed may be selected from a plurality of predetermined wiper speeds in certain example instances. In some example embodiments, only a single wipe is initiated for boundary conditions detected in one or both of the determining steps.

In certain example embodiments of this invention, there is provided a method of engaging windshield wipers of a vehicle in response to detected rain, the method comprising reading data from a capacitive array having at least two capacitors; mathematically comparing data from each capacitor individually (e.g., autocorrelating); determining from the mathematically compared individual capacitor data whether it is raining; mathematically comparing data from different capacitors (e.g., cross-correlating); determining from the mathematically compared different capacitor data a type and/or an amount of rain; engaging the wipers if rain is detected; and, stopping or not actuating the wipers if one or both of the determining steps determines that it is not raining.

In certain example embodiments, a sigma-delta modulator or other suitable circuit or software may be used to perform an analog-to-digital (A/D) conversion of data from the capacitive array. Additionally, in certain example embodiments, a software or other type of comparator may perform at least one of checking autocorrelation data for negative values, calculating whether a gradient of autocorrelation data is greater than one, and/or attempting to match or Substantially match a shape of autocorrelation data with autocorrelation data stored in a database. In certain instances, the correlating engine computes cross-correlations when all conditions tested for by the comparator are met.

In certain example embodiments of this invention, there is provided a system or method for engaging windshield wipers in response to detected rain, the system (or method) comprising a capacitive array having at least two capacitors; circuitry that reads capacitance data from the capacitive array; a correlating engine or correlator that autocorrelates data from the circuitry to determine the existence of rain, and cross-correlates data from the circuitry to determine a type and/or an amount of rain if it is determined that rain exists; and, a wiper motor that is capable of receiving a signal for directing whether the wipers should move or stop. In certain example embodiments, a symmetry level of a cross-correlation curve is computed, and the wiper motor may select a wiper speed related to the symmetry level.

In certain example embodiments, a rain sensor comprises at least two sensing devices (e.g., sensing capacitors or the like) that are affected by rain on a surface of a window; circuitry that provides an output related to the sensing devices; and at least one correlating engine that (a) auto-correlates information from said circuitry to determine whether rain is present, and/or (b) cross-correlates information from said circuitry to determine how fast to operate at least one wiper of a vehicle and/or an amount of rain.

In certain example embodiments, a method or system for engaging window wiper(s) in response to detected rain is provided and comprises a capacitive array having at least two capacitors; circuitry that reads capacitance data from the capacitive array; an algorithm that mathematically determines existence of rain on the window based on data from the circuitry, and mathematically quantifies a type and/or amount of rain if it is determined that rain exists; and, a wiper motor capable of receiving a signal(s) directing whether the wiper(s) should move or stop.

In certain example embodiments, a rain sensor for a vehicle is provided. A printed circuit board (PCB) supported by a vehicle window comprises first and second outer layers and at least one inner layer. The first outer layer is closest to an interior of the vehicle, and the second outer layer is closest to an exterior of the vehicle. First and second capacitor arrays are provided. The first capacitor array is formed on an outer surface of the first outer layer of the PCB, and the second capacitor array is formed on an outer surface of the second outer layer of the PCB. One or more sensing capacitors in the first and/or second capacitor arrays is/are sensitive to moisture on an external surface of the window. Programmed logic circuitry is configured to distinguish between moisture on the exterior surface of the vehicle window, humidity on the interior surface of the vehicle window, and EMI. The at least one inner layer is arranged so as to decouple the first and second capacitor arrays and to shield the first capacitor array from fields emanating from the second capacitor array and vice versa. EMI is detected when the first and second capacitor arrays detect identical or similar signals substantially simultaneously.

In certain example embodiments, a flexible printed circuit board (PCB) supported by a vehicle window is provided. A first outer layer is provided, with the first outer layer being closest to an interior of the vehicle and being formed from a flexible polymer. A second outer layer is provided, with the second outer layer being closest to an exterior of the vehicle and being formed from a flexible polymer. A first capacitor array comprising a first plurality of sensing capacitors is printed or etched on the first outer layer of the PCB. A second capacitor array comprising a second plurality of sensing capacitors is printed or etched on the second outer layer of the PCB closest to the vehicle window. Programmed logic circuitry is configured to distinguish between moisture on the exterior surface of the vehicle window, humidity on the interior surface of the vehicle window, and EMI, in dependence on signals generated by the first and second capacitor arrays. At least one substantially metallic inner layer is arranged so as to decouple the first and second capacitor arrays and to shield the first capacitor array from fields emanating from the second capacitor array and vice versa. The first and second capacitor arrays are formed on opposing surfaces of the flexible PCB. EMI is detected when the first and second capacitor arrays detect identical or similar signals substantially simultaneously.

In certain example embodiments, an electronic device mountable in or on a vehicle window is provided. A flexible printed circuit board (PCB) is provided. First and second sensing circuits are formed on opposing sides of the flexible PCB, with each said sensing circuit comprising a plurality of different fractal structures. A ground plane is located between the first and second sensing circuits, with the ground plane being arranged so as to decouple the first and second capacitor arrays and to shield the first capacitor array from fields emanating from the second capacitor array and vice versa. The electronic device is configured to detect moisture on an exterior surface of the vehicle window, humidity on an interior surface of the vehicle window, and EMI.

In certain example embodiments, a light sensor for a vehicle is provided. A printed circuit board (PCB) supported by a vehicle window comprises first and second outer layers and at least one inner layer, with the first outer layer being closest to an interior of the vehicle and the second outer layer being closest to an exterior of the vehicle. A light sensor flip-chip is mounted to an inner surface of the first outer layer of the PCB, with the light sensor flip-chip including at least two light sensor arrays, and with each said sensor array being configured to sense light of a predetermined wavelength. Programmed logic circuitry is configured to set a state of the vehicle lights in dependence on the light sensor. The at least two light sensor arrays are arranged so as to see through a hole formed in the PCB, the hole in the PCB acting as a lens.

In certain example embodiments, a flexible printed circuit board (PCB) supported by a vehicle window is provided. A first outer layer is provided, with the first outer layer being closest to an interior of the vehicle and being formed from a flexible polymer. A second outer layer is provided, with the second outer layer being closest to an exterior of the vehicle and being formed from a flexible polymer. At least one substantially metallic inner layer is provided. A light sensor comprising a light sensor flip-chip is mounted to an inner surface of the first outer layer of the PCB, with the light sensor flip-chip including at least two light sensor arrays, and with each said sensor array being configured to sense light of a predetermined wavelength. Programmed logic circuitry is configured to set a state of the vehicle lights in dependence on the light sensor. The at least two light sensor arrays are arranged so as to see through a hole formed in the PCB, the hole in the PCB acting as a lens.

In certain example embodiments, a vehicle window is provided. First and second substantially parallel spaced-apart glass substrates are laminated together via a polymer-inclusive layer. An opaque layer is provided. A printed circuit board (PCB) includes a light sensor comprising a light sensor flip-chip, the light sensor flip-chip including at least two light sensor arrays, each said sensor array being configured to sense light of a predetermined wavelength. An adhesive bonds the light sensor to the PCB. A hole is formed in the PCB and the opaque layer so as to allow the light sensor arrays to see through the hole formed in the PCB and the opaque layer. A state of the vehicle lights is settable in dependence on the light sensor. The PCB is located in or is supported by the vehicle windshield.

In certain example embodiments, a method of operating vehicle lights is provided. A capacitive light sensor is configured to sense a presence and intensity of light over at least one wavelength, with each said wavelength being associated with a respective output channel of the light sensor. A buffer is filled with data from the at least one output channel, with the buffer being filled with a predetermined number of data points at a predetermined frequency. An edge change is detected in the data in the buffer. An on/off state of the vehicle lights is maintained when an edge change is not detected. When an edge change is detected, when the data passes from a high value to a low value through a first predefined threshold and remains lower than the first predefined threshold for a persistence interval, the vehicle lights are turned on, and when the data passes from a low value to a high value through a second predefined threshold and remains higher than the second predefined threshold value for the persistence interval, the vehicle lights are turned off. The second threshold is equal to the first threshold plus a hysteresis factor.

In certain example embodiments, a method of operating vehicle lights is provided. A capacitive light sensor is configured to sense a presence and intensity of light over three wavelengths, with each said wavelength being respectively associated with first, second, and third output channels of the light sensor. A buffer is filled with data from the output channels, with the buffer being filled with a predetermined number of data points at a predetermined frequency. An edge change is detected in the data in the buffer. A speed of the vehicle is determined. When the vehicle speed exceeds a first speed threshold, a predefined speed hysteresis factor is added to the first and second thresholds until the vehicle speed drops below a second speed threshold. Edge changes in at least two of the first, second, and third channels are correlated. The on/off state of the vehicle lights is changed in dependence on the correlation. The second threshold is equal to the first threshold plus a hysteresis factor.

In certain example embodiments, a light sensor for a vehicle is provided. At least one capacitive light sensor array is configured to sense a presence and intensity of light over at least one wavelength, with each said wavelength being associated with a respective output channel of the light sensor array. A buffer is configured to store data from the at least one output channel, with the buffer being filled with a predetermined number of data points at a predetermined frequency. Light sensing programmed logic circuitry is configured to: (a) detect an edge change in the data in the buffer, (b) maintain an on/off state of the vehicle lights when an edge change is not detected, and (c) when an edge change is detected: when the data passes from a high value to a low value through a first predefined threshold and remains lower than the first predefined threshold for a persistence interval, generate a signal indicating that the vehicle lights are to be turned on, and when the data passes from a low value to a high value through a second predefined threshold and remains higher than the second predefined threshold value for the persistence interval, generate a signal indicate that the vehicle lights are to be turned off. The second threshold is equal to the first threshold plus a hysteresis factor.

In certain example embodiments, a light sensor for a vehicle is provided.

At least one capacitive light sensor array is configured to sense a presence and intensity of light over a plurality of wavelengths, with each said wavelength being associated with a respective output channel of the light sensor array. A buffer is configured to store data from the output channels, with the buffer being filled with a predetermined number of data points at a predetermined frequency. Light sensing programmed logic circuitry is configured to detect an edge change in the data in the buffet. Speed determining programmed logic circuitry is configured to determine a speed of the vehicle. The light sensing programmed logic circuitry is further configured to add a predefined speed hysteresis factor to the first and second thresholds when the vehicle speed exceeds a first speed threshold until the vehicle speed drops below a second speed threshold, correlate edge changes in at least some of the plurality of channels, and change the on/off state of the vehicle lights in dependence on the correlation. The second threshold is equal to the first threshold plus a hysteresis factor.

In certain example embodiments, there is provided a method of removing condensation from a refrigerator/freezer door including at least one glass substrate. The door is connected to a heating system operable in at least first and second modes. When the heating system is operating in the first mode, the door is heated while condensation is detected as being present thereon, as determined via a moisture detector. When the heating system is operating in the second mode: the door is heated when the door is determined to be open, and the heating is continued until either the door is determined to be closed, or a thermal runaway is detected, whichever comes first.

In certain example embodiments, a refrigerator/freezer merchandiser is provided. A door comprises at least first and second substantially parallel glass substrates. A switch is configured to provide a signal indicative of whether the door is open or closed. At least one moisture detector is configured to detect the presence of condensation on the door. A heating system is configured to apply heat to the door upon instructions from a controller thereof. The controller is configured to: operate in a first mode, wherein the heating system is caused to heat the door while condensation is detected as being present thereon, as determined via the at least one moisture detector; and operate in a second mode, wherein the heating system is caused to heat the door when the switch indicates that the door is open and while the controller does not detect a thermal runaway.

In certain example embodiments, a refrigerator/freezer merchandiser is provided. A door comprises at least first and second substantially parallel glass substrates. A continuous or patterned conductive coating is supported by the first and/or second substrate. At least one moisture detector is configured to detect the presence and type of condensation on the door, if any. A controller is configured to cause an AC power source to generate a pulsed AC signal to be generated and passed to the conductive coating at one or more frequencies selected in dependence on the type of moisture present.

In certain example embodiments, a method of detecting moisture on a glass substrate is provided. A parameterized model (M) is provided for a possible moisture-related disturbance. Background information (I) concerning the model is provided, with I being known a priori. A prior probability of M given I, P(M|I), is calculated. Data from at least one sensor (D) connected to the substrate is collected. A probability of the model given D and I, P(M|D,I), is computed. The computing of P(M|D,I) is repeated as additional data is collected. The model is accepted if P(M|D,I) is greater than 0.9; otherwise, it is rejected. The glass substrate is a part of a vehicle window, building window, or merchandiser.

In certain example embodiments, a method of detecting moisture on a glass substrate is provided. A plurality of parameterized models (Mx) are provided for different possible disturbances. Background information (Ix) concerning each of the models is provided. A prior probability of Mx given Ix, P(Mx|Ix), is calculated. Data from at least one sensor (D) connected to the substrate is collected. A probability of each said model given D and Ix, P(Mx|D,Ix), is computed. The computing of P(Mx|D,Ix) is repeated as additional data is collected. The probability of each said model is compared to a predetermined threshold. Each said model is accepted or rejected based on the comparing. When a particular model is accepted, an action is caused relative to the glass substrate in dependence on the particular model that is accepted.

In certain example embodiments, there is provided non-transitory computer readable storage medium tangibly storing instructions that, when executed by at least one processor, perform one of these methods.

In certain example embodiments, there is provided an electronic device located in close relative proximity to a glass substrate. A first memory location stores a plurality of parameterized models (Mx) for different possible disturbances. A second memory location stores background information (Ix) concerning each of the models. At least one sensor is configured to collect data from at least one sensor (D) connected to the substrate. At least one processor is configured to: calculate a prior probability of Mx given Ix, P(Mx|Ix); compute a probability of each said model given D and Ix, P(Mx|D,Ix); repeat computations of P(Mx|D,Ix) as additional data is collected by the at least one sensor; compare the probability of each said model to a predetermined threshold; and accept or reject each said model based on the comparing.

Parameterized models may be stored for both moisture-related disturbances and non-moisture-related disturbances.

The device may be incorporated into a vehicle in certain example embodiments, in which the glass substrate is at least a part of a vehicle windshield, and the action to be taken is selected from the group consisting of turning on/off windshield wipers, turning on/off defrosters, and turning on/off the vehicle's lights.

The device may be incorporated into a merchandiser in certain example embodiments, in which the glass substrate is at least a part of a door to the merchandiser, and the action to be taken includes turning on/off a heater so as to facilitate removal of condensate built up on the door.

BRIEF DESCRIPTION OF THE DRAWINGS

These and other features and advantages will be better and more completely understood by reference to the following detailed description of exemplary illustrative embodiments in conjunction with the drawings, of which:

FIG. 2A is an exemplary optimized pattern for a quadrant capacitive array based on Hilbert fractals, where such capacitors may be provided on the window as a sensor array in the embodiments of one or more of FIGS. 1(a)-1(f) and 4-12 for example.

FIG. 12A is an exemplary correlation matrix indicative of light rain.

FIG. 12B is an exemplary correlation matrix indicative of heavy rain.

FIG. 14 is a chart setting forth example cross-correlation data from capacitors C1, C2 according to examples of certain embodiments of this invention.

FIG. 31 illustrates a switching circuit which may be used in conjunction with any of the other embodiments of this invention, so as to selectively switch between different sensing capacitors in order to change the sensing field being analyzed and/or change the feature being searched for.

FIG. 49 is pseudo-code for the Hamiltonian Markov Chain Algorithm.

DETAILED DESCRIPTION OF EXAMPLE EMBODIMENTS OF THE INVENTION

Figure 1A:
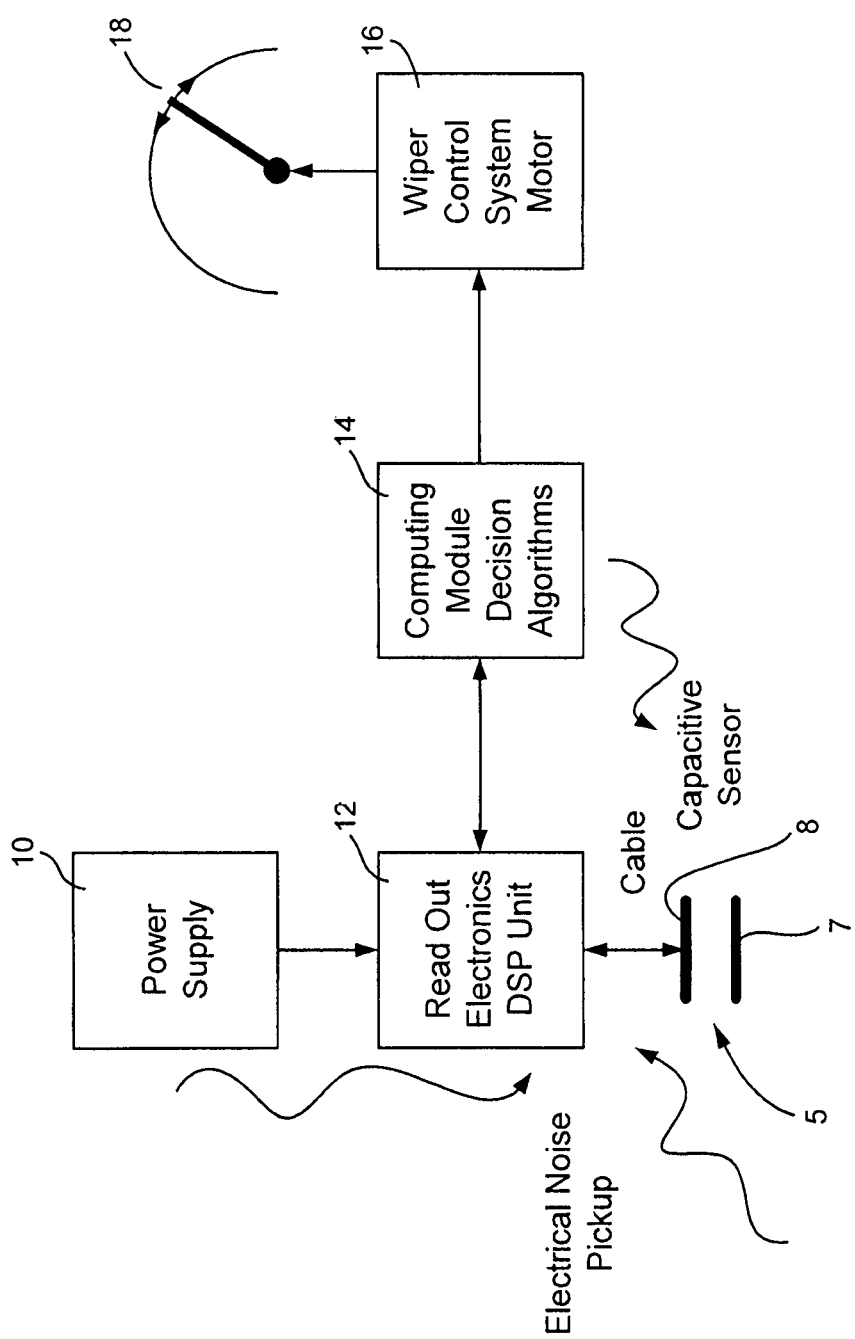
FIG. 1(a) is a block diagram of components of an exemplary rain sensor according to an example embodiment of this invention.

Referring now more particularly to the accompanying drawings in which like reference numerals indicate like parts throughout the several views.

In certain example embodiments of this invention, a moisture (e.g., rain) sensor system and/or method is provided and includes capacitance-based detection which translates a physical input signal (e.g., the presence of a drop of water on a windshield, or the like) into a digital electrical voltage signal which is received and interpreted by a software program(s) or circuit(s) that decides whether windshield wipers should be activated, and, if so, optionally their proper speed. Thus, capacitive coupling is used to detect water and/or other material in the exterior surface of a window such as a vehicle windshield, sunroof, and/or backlite. It will be appreciated that computational methods may be performed by hardware or a combination of hardware and software in different example embodiments of this invention. In certain example embodiments of this invention, no reference capacitance or capacitor is needed (i.e., no compensation capacitor is needed).

In certain example embodiments of this invention, a plurality of sensing capacitors are supported by a window such as a vehicle windshield, the capacitors each having a different field. A sensing circuit outputs an analog signal that is based on and/or related to the capacitances of the sensing capacitors. In certain example embodiments, a switching circuit is provided in order to selectively switch between different sensing capacitors or different combinations thereof (or even possibly antennas and/or bands), in order to change the sensing field being analyzed and/or change the feature being searched for (e.g., see FIGS. 4, 5, 26 and 31). For example, in certain example embodiments, the switching circuit may selectively switch between: (a) capacitor(s) for detecting rain on an exterior surface of the window, and (b) capacitor(s) for detecting one or more of ice on an exterior surface of the window, mist on an exterior surface of the window, and/or moisture on an interior surface of the window. Such embodiments may or may not be used in combination with any other embodiment(s) of this invention discussed herein.

Certain example embodiments of this invention take advantage of a permittivity equation, which gives a physical quantity that describes how an electric field affects and is affected by a medium. An example basic permittivity equation is:

$$D=\varepsilon_0 E+P,$$

where D is electrical flux, $\varepsilon_0$ is the dielectric constant of a vacuum, E is an electrical field (e.g., the voltage setup between plates or electrodes divided by distance, or V/m), and P is polarization. Polarization P can be further described mathematically as:

$$P=\varepsilon_r\varepsilon_0 E,$$

where $\varepsilon_r$ is relative permittivity (e.g., the dielectric constant of water, ice, dirt or anything else that could be on an exterior surface of a window such as a windshield). In general, a high value of $\varepsilon_r$ will correspond to high polarizability. The permittivity of glass is approximately 8, and the permittivity of water is approximately 85. By substitution and factorization, then, the permittivity equation can be rewritten as:

$$D=\varepsilon_0(\varepsilon_r+1)E.$$

In this form, it will be appreciated that D is the response to excitation E.

Capacitance C is given by C=Q/V, where Q is the charge and V is the potential, in volts. Additionally, C=Φ/V, where Φ is the electric flux associated with charge Q. By Gauss' Law:

$$\Phi=o\int_S E \cdot dA,$$

where dA is the area of a differential square on the closed surface S. By substitution, then, it becomes clear that capacitance is related to potential difference:

$$C=\int D dA/V.$$

These equations form the basis of an example technique for measuring the interaction of water on glass by using a sensor with a capacitive array to probe above the window (e.g., glass). In particular, data from a sensor including at least one, or two or more, capacitor(s) (e.g., C1, C2, C3, etc.) may be used to detect whether moisture (e.g., rain, or the like) is present on an exterior surface of a window such as a vehicle windshield or backlite. The above equations illustrate that the presence of water on the surface of a window can affect the capacitance of an appropriately positioned sensing capacitor.

FIG. 1(*a*) is a block diagram of example components of a moisture (e.g., rain) sensor according to an example embodiment of this invention. Power supply 10 is connected to readout electronics 12 which may include one or more of hardware, firmware, and/or software. As will be described in greater detail below, the sensor includes one or more capacitors so as to make up a capacitive sensor 5 in certain example embodiments. While different types of capacitors may be used, capacitors each having a pair of approximately coplanar electrodes arranged in a fractal pattern may be used in the sensor in certain example embodiments of this invention. In certain example embodiments, a fractal pattern may be divided into a capacitive array. Data from and/or related to the sensing capacitor(s) of the capacitive sensor 5 is received and read by readout electronics 12 which may be made up of one or more of hardware, firmware and/or software. Readout electronics 12 pick up electrical noise and convert the same to digital signal(s). This digital signal(s) is passed to computing module 14 (which may be made up of one or more of hardware, firmware and/or software) which determines what action the wipers should take. For example, the wipers might initiate a single wipe, low-speed wipes, high-speed wipes, etc., based on the data analyzed from and/or related to the capacitive sensor. The wipers also may be caused to turn off, slow/increase the speed at which they are wiping, etc., based on the data analyzed from and/or related to the capacitive sensor. Wiper control system motor 16 receives instructions from computing module 14 and directs wipers 18 to take the appropriate action.

In certain example embodiments, the capacitive sensor 5 interfaces with a Local Interconnect Bus (LIN bus) of a vehicle. A LIN bus (not shown) typically is a serial bus to which slave devices in an automobile are connected. A LIN bus typically executes a handshake(s) with slave devices to ensure that they are, for example, connected and functional. Additionally, a LIN bus may provide other information to slave devices, such as, for example, the current time.

In certain example embodiments of this invention, the capacitive sensor 5 includes a plurality of capacitors in the form of any suitable array.

FIG. 1(*b*) is a cross-sectional view of a vehicle window including a moisture sensor according to an example embodiment of this invention. A windshield of the vehicle includes inner glass substrate 1 and outer glass substrate 2 that are laminated together via a polymer-inclusive interlayer 3 of a material such as polyvinyl butyral (PVB) or the like. An optional low-e (low emissivity) coating 4 may be provided on the inner surface of the exterior glass substrate 2 (or even on the surface of substrate 1) in certain example embodiments of this invention. A low-E coating 4 typically includes at least one thin IR reflecting layer of a material such as silver, gold or the like sandwiched between at least first and second dielectric layers of material such as silicon nitride, tin oxide, zinc oxide, or the like. Example low-E coatings 4, for purposes of example and without limitation, are described in U.S. Pat. Nos. 6,686,050, 6,723,211, 6,782, 718, 6,749,941, 6,730,352, 6,802,943, 4,782,216, 3,682,528, and 6,936,347, the disclosures of which are hereby incorporated herein by reference.

Figure 1B:
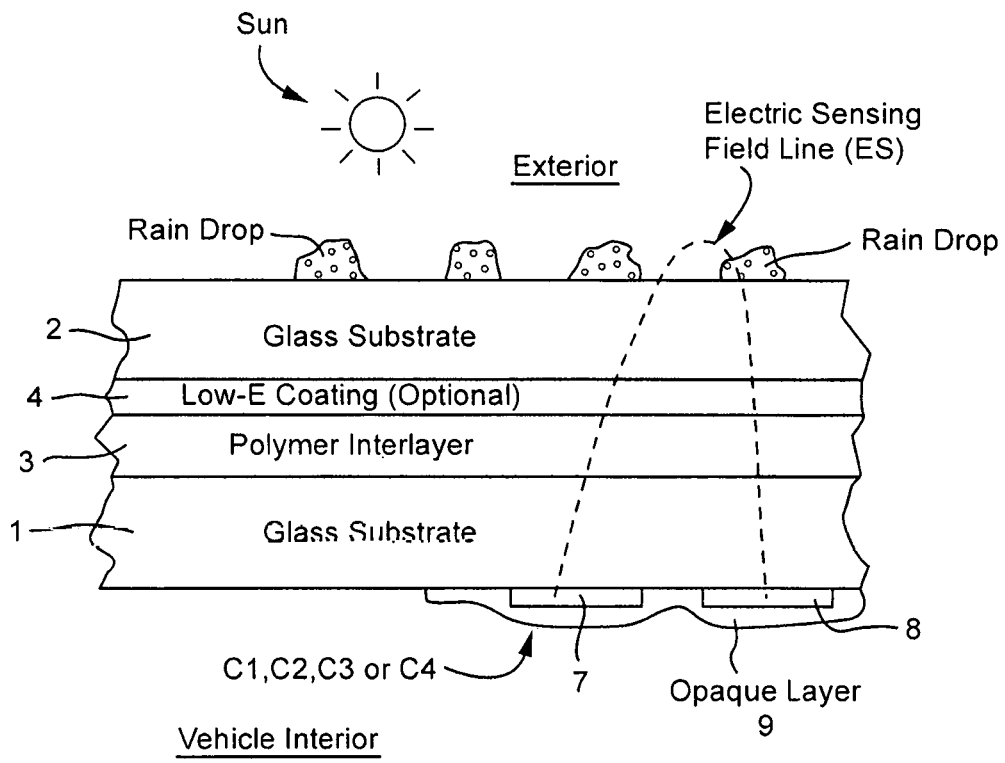
FIG. 1(b) is a cross sectional view of a rain sensor according to an example embodiment of this invention, that may use the features of FIG. 1(a) and/or one or more of FIGS. 2-12.

FIG. 1(b) illustrates an example capacitor of the capacitive sensor. While the capacitive sensor of FIG. 1(a) typically includes a plurality of capacitors in an array, only one capacitor of the sensor is shown in FIG. 1(b) for purposes of simplicity. The other capacitors are similar in cross section to the one shown in FIG. 1(b) in certain example embodiments of this invention. The example capacitor (C1, C2, C3 or C4) of the capacitive sensor shown in FIG. 1(b) includes a pair of spaced apart coplanar or substantially coplanar capacitor electrodes 7 and 8. The electrodes 7 and 8 are of a conductive material that may be printed or otherwise formed on the window. For example, the capacitor electrodes 7 and 8 of the sensing capacitor may be made of or include silver, ITO (indium tin oxide), or other suitable conductive material. In certain example embodiments, the capacitor shown in FIG. 1(b) is affected by a rain droplet on the exterior surface of the window because electric field Es of the capacitor extends to or beyond the exterior surface of the window as shown in FIG. 1(b) and thus can interact with the rain droplet or other material on the window's exterior surface. Signals received from and/or relating to the sensing capacitor(s) and analysis thereof is described herein.

In the FIG. 1(b) embodiment, an opaque insulating layer (e.g., black frit or enamel, or the like) 9 is provided on the window over the electrodes 7 and 8 in order to shield the electrodes 7, 8 from the view of a passenger(s) sitting inside the vehicle. Thus, it will be appreciated that the opaque layer 9 is only provided on a small portion of the window, including in the area where the capacitive array of the rain sensor's array of capacitors is located. In certain example instances, the rain sensor's capacitive array and thus the opaque layer 9 may be located on a vehicle windshield in an area proximate the rear-view mirror mounting bracket. In certain example embodiments, the opaque layer 9 (e.g., black frit or enamel) may contact the fractal pattern of the capacitor electrodes 7, 8 directly because the layer 9 is not conductive. However, even if a black frit layer 9 were conductive (which is possible), its dielectric constant is close to that of water so that it will not adversely interfere with the capturing of data from and/or related to the capacitors C1-C4 and associated analysis.

FIG. 2A is a top or, plan view illustrating an example capacitive sensor array including four capacitors C1, C2, C3 and C4. Each of these capacitors C1, C2, C3 and C4 includes first and second spaced apart coplanar capacitor electrodes 7 and 8 as shown in FIG. 1(b) (or any of FIGS. 1(c)-1(f)). The capacitor electrodes 7 and 8 of each capacitor C1-C4 may be made of conductive silver frit or the like as shown in FIG. 2A. Moreover, in certain example embodiments, there may be a gap 22 of from about 0.2 to 1.5 mm, more preferably from about 0.3 to 1.0 mm (e.g., 0.6 mm), between the coplanar capacitor electrodes 7 and 8 of a capacitor (C1, C2, C3 and/or C4) as shown in FIG. 2A. In the FIG. 2A embodiment, the capacitors C1-C4 are covered with an insulating black frit layer 9 which is the same as the opaque layer 9 discussed above with respect to FIG. 1(b). In FIG. 2A, a contact pad array is provided in the center of the sensor array, and includes four contact pads electrically connected to the respective electrodes 7 of the capacitors C1-C4, and four contact pads electrically connected to the respective electrodes 8 of the capacitors C1-C4. An example contact pad is referred to by reference numeral 28 in FIG. 2A. The four white colored contact pads 28 in FIG. 2A are electrically connected to the respective capacitor electrodes 7 of capacitors C1-C4, whereas the dark grey colored contact pads 28 in FIG. 2A are electrically connected to the respective capacitor electrodes 8 of the capacitors C1-C4. All of the sensing capacitors C1-C4 are sensitive to moisture such as rain on the external surface of the window.

In the FIG. 2A embodiment, each of the capacitors C1-C4 of the capacitive sensor is formed using fractal geometry. In particular, each of the coplanar electrodes 7 and 8 of each capacitor C1-C4 is formed with a fractal geometry. Fractal design patterns allow, for example, a high capacitance to be realized in a small area, and are therefore desirable over other geometries in certain example rain sensor applications. Fractal geometry may be grouped into (a) random fractals, which may be called chaotic or Brownian fractals and include a random noise component, and (b) deterministic or exact fractals. In deterministic fractal geometry, a self-similar structure results from the repetition of a design or motif (or "generator") (i.e., self-similarity and structure at all scales). In deterministic or exact self-similarity, fractal capacitors may be constructed through recursive or iterative means. In other words, fractals are often composed of or include many copies of themselves at different scales.

In the FIG. 2A embodiment, it can be seen that the coplanar electrodes 7 and 8 of each capacitor (where the electrodes 7 and 8 are shown but not labeled in FIG. 2A due to the dark color of the frit 9, but are spaced apart by gaps 22) have fractal geometries and are arranged substantially parallel to each other throughout the meandering length of each capacitor. In other words, each electrode 7, 8 of a given capacitor (e.g., C1, C2, C3 or C4) has a meandering shape in the fractal geometry, but stays substantially parallel to the other electrode (the other of 7, 8) of the capacitor throughout the meandering length of the capacitor. The overall length of each capacitor (e.g., C1), along the meandering length of the fractal, is from about 25 to 200 mm in certain example embodiments of this invention, more preferably from about 30 to 90 mm, with an example being about 50 mm.

Figure 2B:
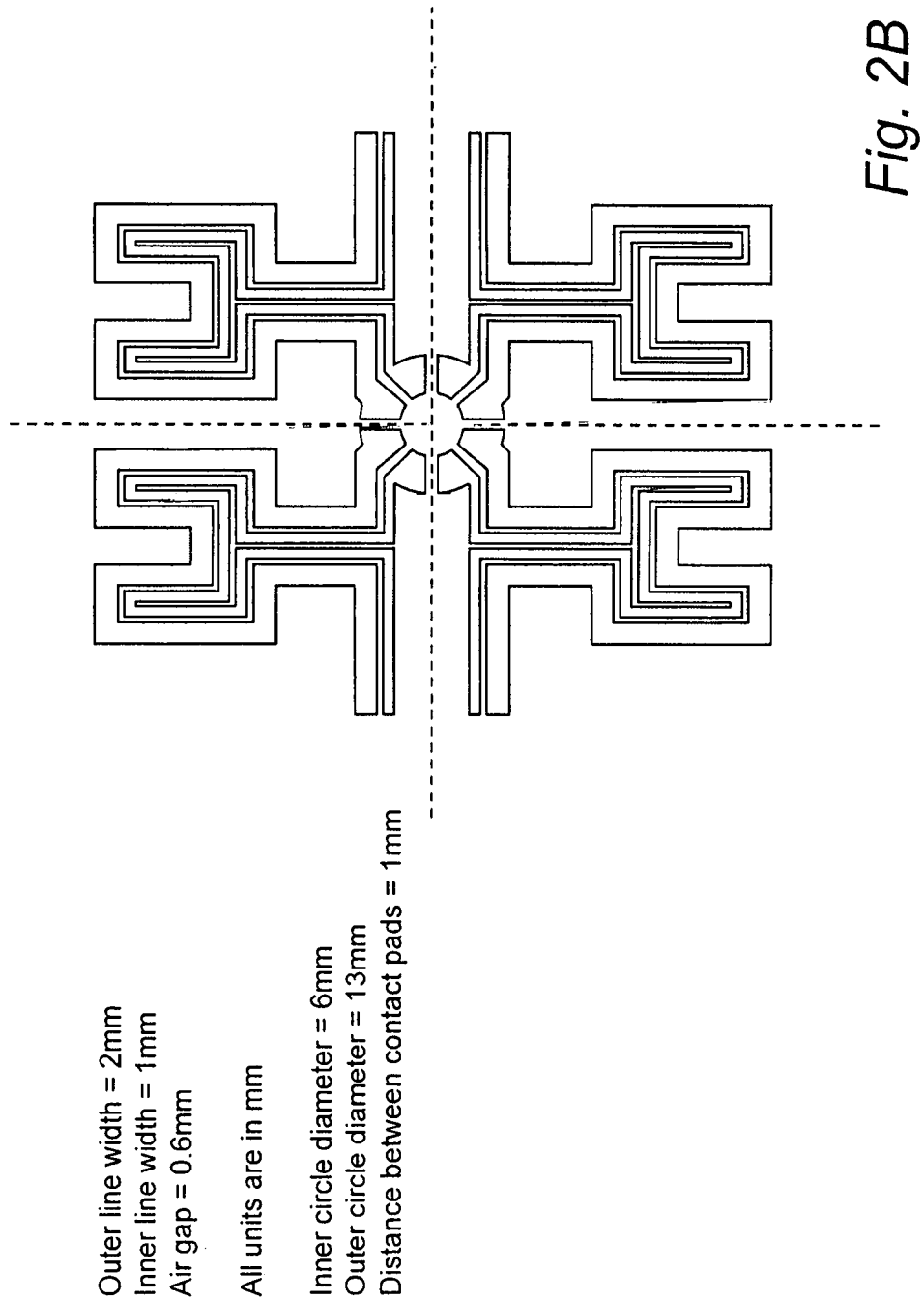
FIG. 2B is another exemplary optimized pattern for a quadrant capacitive array, where such capacitors may be provided on the window as a sensor array in the embodiments of one or more of FIGS. 1(a)-1(f) and 4-12 for example.
Figure 3:
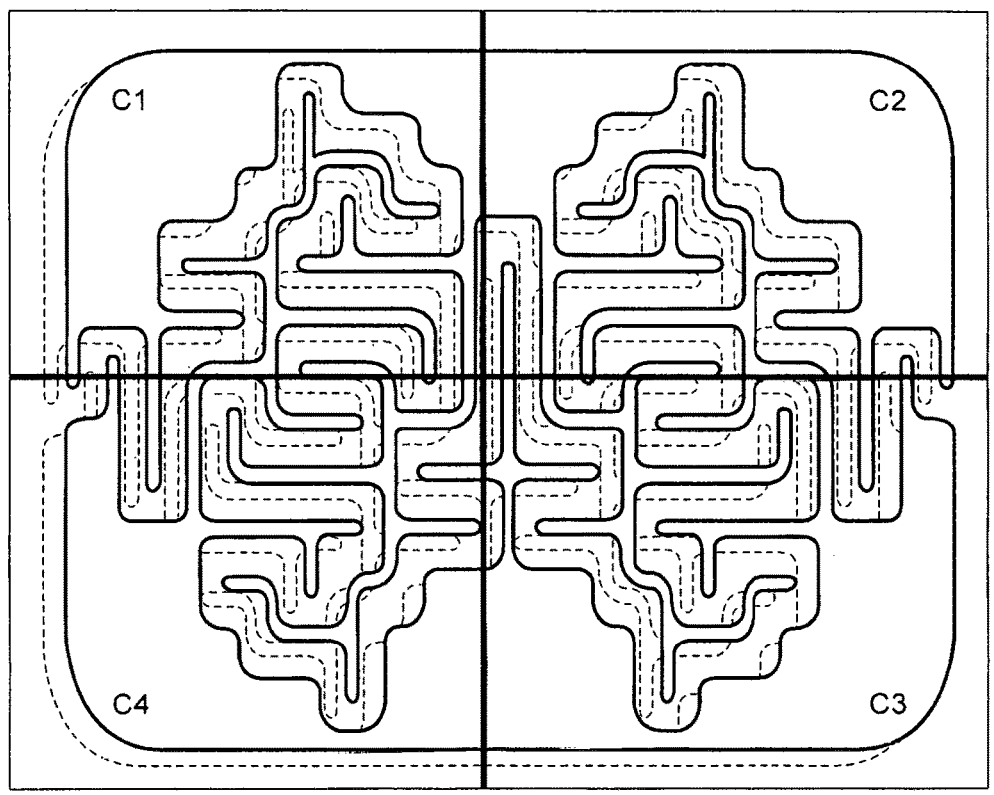
FIG. 3 is an enlarged picture of yet another exemplary quadrant capacitive array, where such capacitors may be provided on the window as a sensor array in the embodiments of one or more of FIGS. 1(a)-1(f) and 4-12 for example.

The fractal pattern of FIG. 2A is a Hilbert fractal pattern. The electrodes 7, 8 of the capacitors C1-C4 in the FIG. 2A embodiment form a Hilbert fractal pattern, for purposes of example only and without limitation. In particular, the capacitors shown in FIG. 2A are shaped in a third-order Hilbert fractal manner. Hilbert fractals are continuous space-filling fractals, with fractal dimensions of two. This means that higher-order fractals will become more square-like. A Hilbert fractal can be formed by using the following L-system:

```
Hilbert {
    Angle 90
    Axiom X
    X = -YF+XFX+FY-
    Y = +XF-YFY-FX+
}
``` where "Angle 90" sets the following rotations to 90 degrees, X and Y are defined functions, "F" means "draw forward", "+" means "turn counterclockwise", and "−" means "turn clockwise". While Hilbert fractal geometries may be used in forming the capacitors C1-C4 in certain example embodiments of this invention, this invention is not so limited, and other types of fractals may also be used to form the capacitor shapes. For example, the capacitor electrodes 7, 8 of capacitors C1-C4 in any embodiment herein may be formed using any of the fractal designs disclosed in any of U.S. Pat. Nos. 6,552,690, 6,104,349, 6,140,975, 6,127,977, 6,084,285, 6,975,277, the disclosures of which are hereby incorporated herein by reference. In certain example embodiments of this invention, as shown in FIGS. 2A, 2B and 3, all sensing capacitors of the sensing array may be identical or substantially identical in shape.

In preferred embodiments, each of the capacitors C1-C4 in the sensor array may be electrically floating (this may be called a virtual ground in certain example instances) so as to not have a fixed common ground such as a fixed zero volts, and/or spatially separated or the like which may be useful with respect to the correlation functions. Additionally, the lack of a common ground means that the capacitive array will not be subject to adverse effects from interference such as, for example, EMI interference thereby reducing the potential for false wipes, false detections, and the like.

The fractal design for capacitors C1-C4 may be used in any of the embodiments of FIGS. 1(a)-1(f).

Figure 1C:
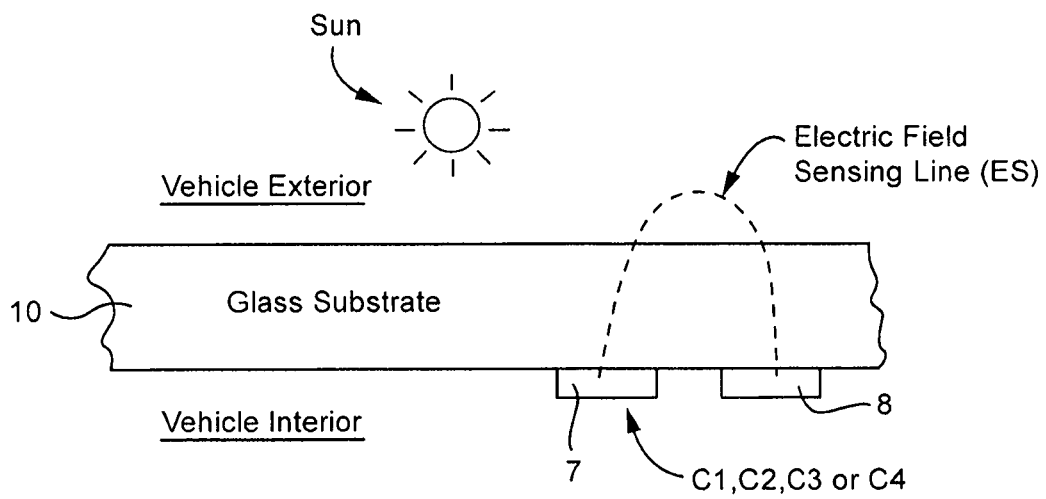
FIG. 1(c) is a cross sectional view of a rain sensor according to another example embodiment of this invention, that may use the features of FIG. 1(a) and/or one or more of FIGS. 2-12.

FIG. 1(c) is a cross sectional view of another example embodiment of this invention, which may use the system of FIG. 1(a) and one or more of the embodiments of FIGS. 2-12. In the FIG. 1(c) embodiment, the vehicle window (e.g., backlite) is made up of only one glass sheet 10, and the electrodes 7, 8 of the capacitor are provided on, directly or indirectly, the interior major surface of the glass sheet 10. The capacitor (e.g., C1) shown in FIG. 1(c) is designed such that it is affected by a rain droplet (or other material) on the exterior surface of the window because the electric field Es of the capacitor extends to or beyond the exterior surface of the window as shown in FIG. 1(c) and thus can interact with the rain droplet or other material on the window's exterior surface. Each of the capacitors C1-C4 is formed in a similar manner. It is noted that the use of the word "on" herein covers both directly on and indirectly on, and is not limited to physical contact or touching unless expressly stated. An opaque layer 9, similar to that shown in the FIG. 1(b) embodiment, may also be provide in the FIG. 1(c) embodiment if desired.

Figure 1D:
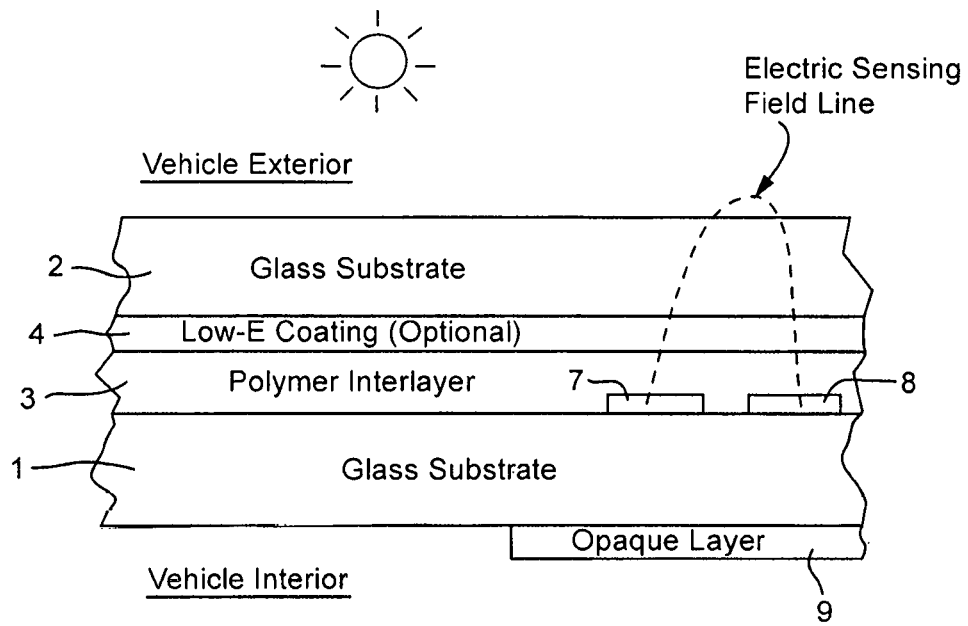
FIG. 1(d) is a cross sectional view of a rain sensor according to another example embodiment of this invention, that may use the features of FIG. 1(a) and/or one or more of FIGS. 2-12.

FIG. 1(d) is a cross sectional view of another example embodiment of this invention, which may use the system of FIG. 1(a) and one or more of the embodiments of FIGS. 2-12. In the FIG. 1(d) embodiment, the vehicle window (e.g., laminated windshield) includes glass sheets 1 and 2 laminated together via polymer based interlayer 3, and optionally includes a low-E coating 4 on either substrate 1 or substrate 2. The FIG. 1(d) embodiment differs from the FIG. 1(b) embodiment in that the electrodes 7, 8 of the capacitor are provided on the major surface of glass substrate 1 that is furthest from the vehicle interior. The capacitor electrodes 7, 8 may contact the polymer interlayer 3 in this embodiment, in certain example instances. The capacitor (e.g., C1, C2, C3 or C4) shown in FIG. 1(d) is designed such that it is affected by a rain droplet (or other material) on the exterior surface of the window because the electric field Es of the capacitor extends to or beyond the exterior surface of the window as shown in FIG. 1(d) and thus can interact with the rain droplet or other material on the window's exterior surface. Each of the capacitors C1-C4 of the sensor array is formed in a manner similar to that shown for the capacitor of FIG. 1(d). Opaque layer 9 may also be provided in the FIG. 1(d) embodiment if desired, over a portion of the window so as to shield the capacitor electrodes from a vehicle passenger's view. In the embodiment shown in FIG. 1(d), the electrodes 7 and 8 may be formed of a conductive silver frit or ITO printed or patterned directly on and contacting the surface of substrate 1. However, this invention is not so limited, and the electrodes 7 and 8 of one or more capacitors of the sensor may instead be formed and patterned from a metallic conductive IR reflecting layer (e.g., silver based layer) of a low-E coating 4 that is supported by the window.

Figure 1E:
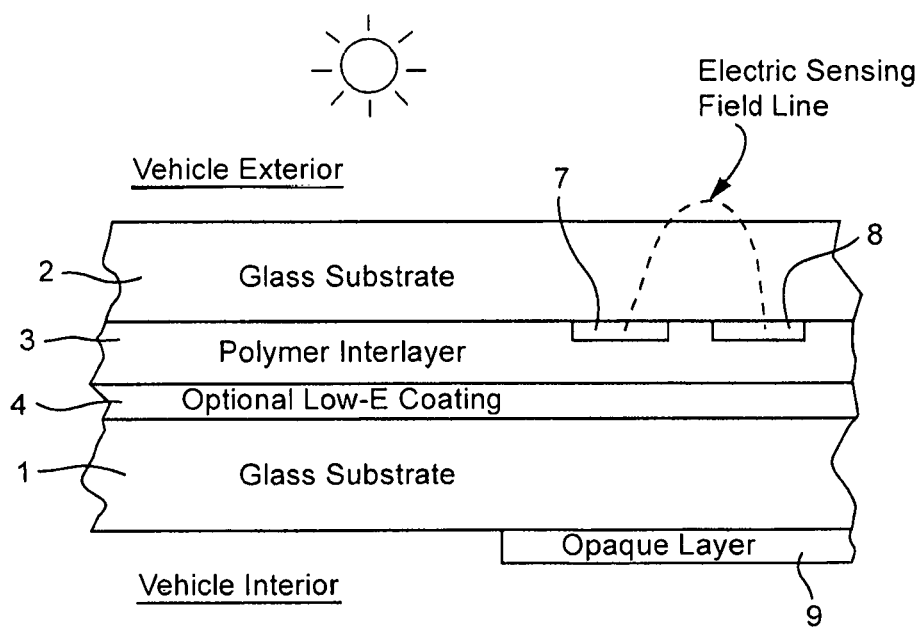
FIG. 1(e) is a cross sectional view of a rain sensor according to another example embodiment of this invention, that may use the features of FIG. 1(a) and/or one or more of FIGS. 2-12.

FIG. 1(e) is a cross sectional view of another example embodiment of this invention, which may use the system of FIG. 1(a) and one or more of the embodiments of FIGS. 2-12. In the FIG. 1(e) embodiment, the vehicle window (e.g., laminated windshield) includes glass sheets 1 and 2 laminated together via polymer based interlayer 3, and optionally includes a low-E coating 4 on either substrate 1 or substrate 2. The FIG. 1(e) embodiment differs from the FIG. 1(b) embodiment in that the electrodes 7, 8 of the capacitor (e.g., C1, C2, C3 or C4) are provided on the major surface of the exterior glass substrate 2 that is closest to the vehicle interior. The capacitor electrodes 7, 8 may contact the polymer interlayer 3 in this embodiment, in certain example instances. The capacitor (e.g., C1, C2, C3 or C4) shown in FIG. 1(e) is designed such that it is affected by a rain droplet (or other material) on the exterior surface of the window because the electric field Es of the capacitor extends to or beyond the exterior surface of the window as shown in FIG. 1(e) and thus can interact with the rain droplet or other material on the window's exterior surface. Each of the capacitors C1-C4 of the sensor array is formed in a manner similar to that shown for the capacitor of FIG. 1(e). Opaque layer 9 may also be provided in the FIG. 1(e) embodiment if desired, over a portion of the window so as to shield the capacitor electrodes from the view of a vehicle passengers(s).

Figure 1F:
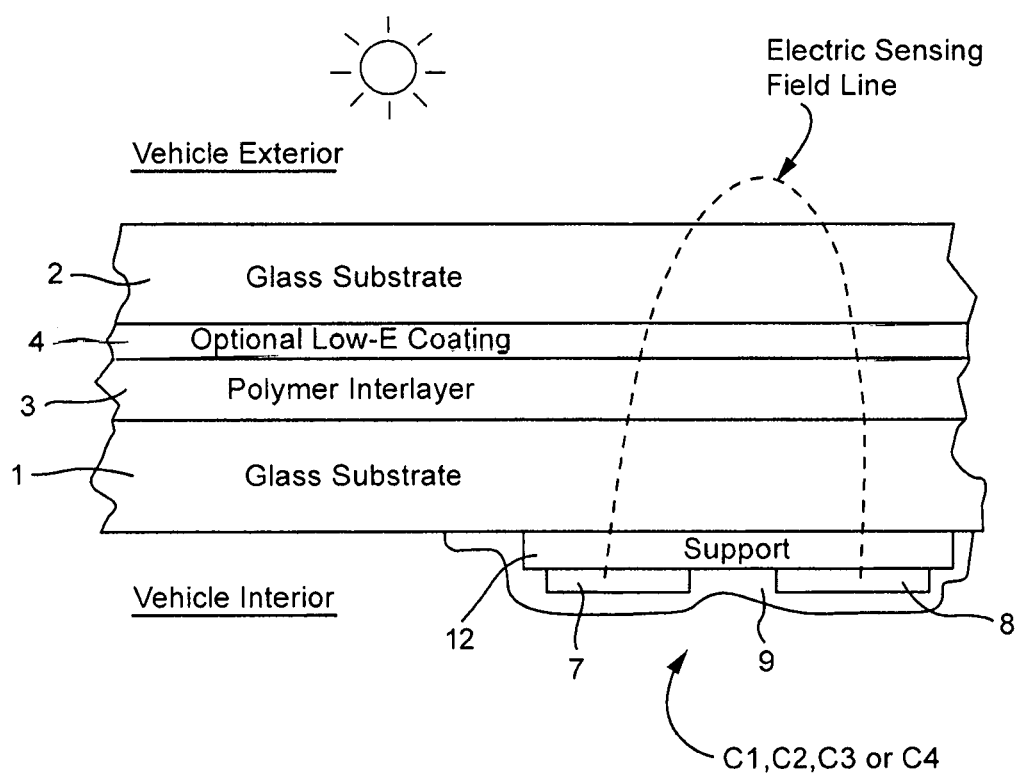
FIG. 1(f) is a cross sectional view of a rain sensor according to another example embodiment of this invention, that may use the features of FIG. 1(a) and/or one or more of FIGS. 2-12.

FIG. 1(f) is a cross sectional view of another example embodiment of this invention, which may use the system of FIG. 1(a) and one or more of the embodiments of FIGS. 2-12. In the FIG. 1(f) embodiment, the vehicle window (e.g., laminated windshield) includes glass sheets 1 and 2 laminated together via polymer based interlayer 3, and optionally includes a low-E coating 4 on either substrate 1 or substrate 2. The FIG. 1(f) embodiment differs from the FIG. 1(b) embodiment in that the electrodes 7, 8 of the capacitor (e.g., C1, C2, C3 or C4) are provided on the major surface of the interior glass substrate 1 that is closest to the vehicle interior, via support member 12. The support member 12, located between the glass substrate 1 and the electrodes 7, 8, may be made of glass, silicon or the like. The capacitor (e.g., C1, C2, C3 or C4) shown in FIG. 1(e) is designed such that it is affected by a rain droplet (or other material) on the exterior surface of the window because the electric field Es of the capacitor extends to or beyond the exterior surface of the window as shown in FIG. 1(f) and thus can interact with the rain droplet or other material on the window's exterior surface. Each of the capacitors C1-C4 of the sensor array is formed in a manner similar to that shown for the capacitor of FIG. 1 (f). Opaque layer 9 may also be provide in the FIG. 1(f) embodiment if desired, over a portion of the window so as to shield the capacitor electrodes 7, 8 from the view of a vehicle passengers(s).

FIG. 2B is a plan view of an example pattern for a quadrant capacitive array of fractal shaped capacitors C1-C4 for the capacitive sensor according to another example embodiment of this invention. The four capacitors shown in FIG. 2B are similar to those of FIG. 2A, except for the precise shapes thereof. The FIG. 2B capacitors may be used in any of the embodiments of FIGS. 1(a)-(f). The superimposed dashed lines show the divisions into four distinct capacitors C1-C4. The outer line width may be about 2 mm, and the inner line width about 1 mm, in certain example embodiments.

FIG. 3 is an enlarged picture of another exemplary quadrant capacitive array of fractal shaped capacitors C1-C4 for the capacitive sensor according to another example embodiment of this invention. The four capacitors shown in FIG. 3 are similar to those of FIGS. 2A and 2B, except for the precise shapes thereof. The FIG. 3 fractal capacitors may be used in any of the embodiments of FIGS. 1(a)-(f). The superimposed lines show example division between capacitors C1-C4 in FIG. 3. It will be appreciated that some example embodiments may have capacitive arrays with as few as two capacitors. However, it is preferable to have at least four capacitors in certain example embodiments to pick up and derive nuances in perturbations.

The use of the fractal geometry for the sensing capacitors C1-C4 can be advantageous in reducing false readings due to EMI interference in certain example embodiments of this invention. In particular, fractals at high iterations help reduce EMI interference issues, because the Faraday cage or quasi-Faraday cage of the fractal at high iterations reduces EMI coupling thereby reducing adverse effects of EMI interference. Fractals at high iterations form quasi-Faraday cages.

In certain example embodiments of this invention, the readout electronics look at the interaction of rain and/or other perturbations on the window. In certain example embodiments, this process may be accomplished by sequentially charging capacitors, reading their data, quantizing that data, and/or erasing the charges.

Figure 4:
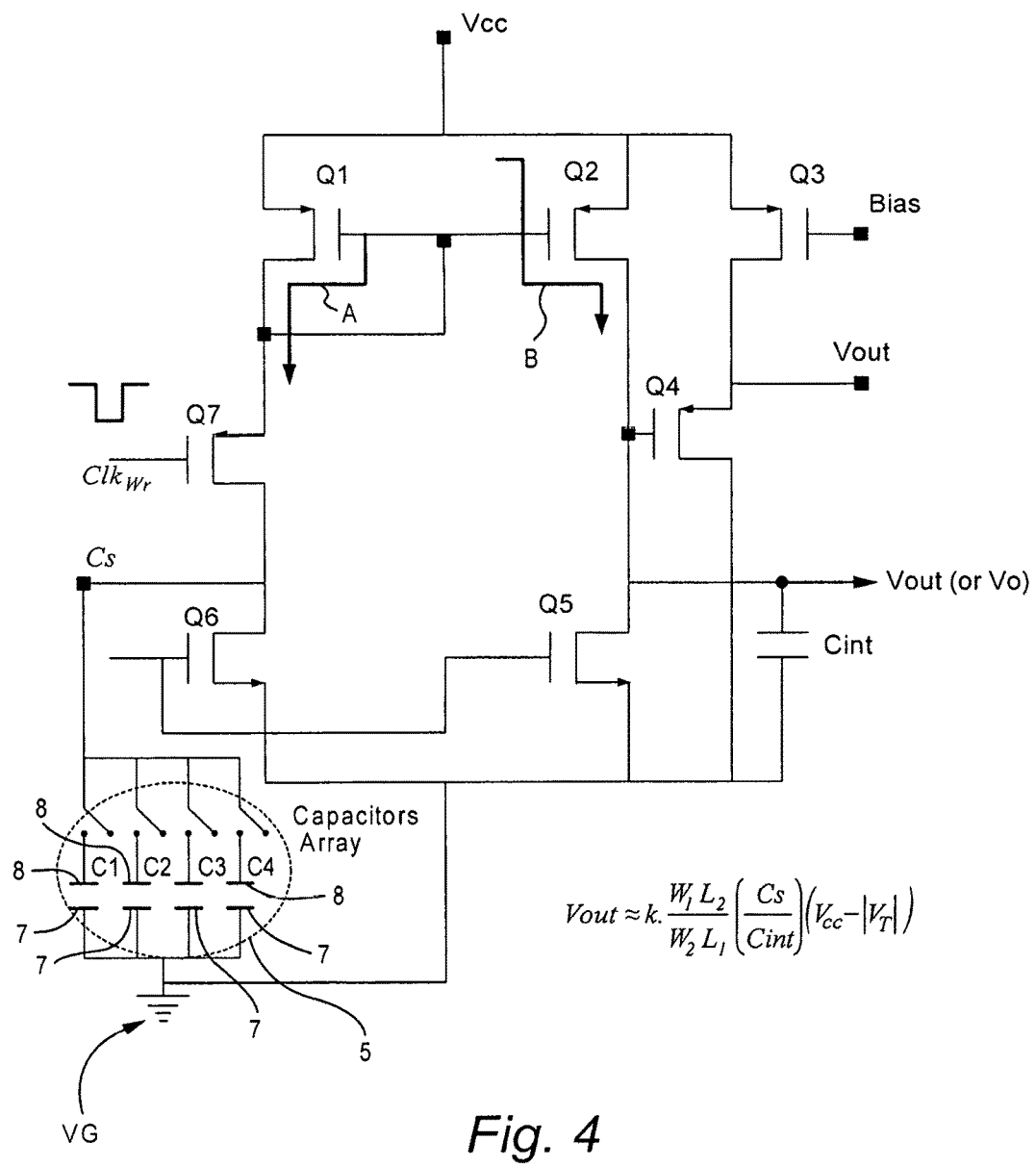
FIG. 4 is an example circuit diagram including exemplary circuitry used for a write clock pulse in readout electronics, for use in one or more of the embodiments of FIGS. 1(a)-1(f) and 5-12 for example.

FIG. 4 is a circuit diagram of a sensing or read-out circuit according to an example embodiment of this invention. The sensing circuit of FIG. 4 may be made up of the electronics unit 12 and the capacitive sensor array 5 of FIG. 1. Any of the capacitors of FIGS. 1(b)-1(f), 2A, 2B, and/or 3 may be used as the capacitors C1-C4 of the circuit in FIG. 4. The FIG. 4 circuitry is used for a write clock pulse in readout electronics, in certain example embodiments of this invention. Transistors Q1, Q2, and Q7 are p-channel MOSFETs, with transistors Q1 and Q2 primarily being responsible for a write phase. Transistors Q5 and Q6 are n-channel MOSFETs.

Figure 6:
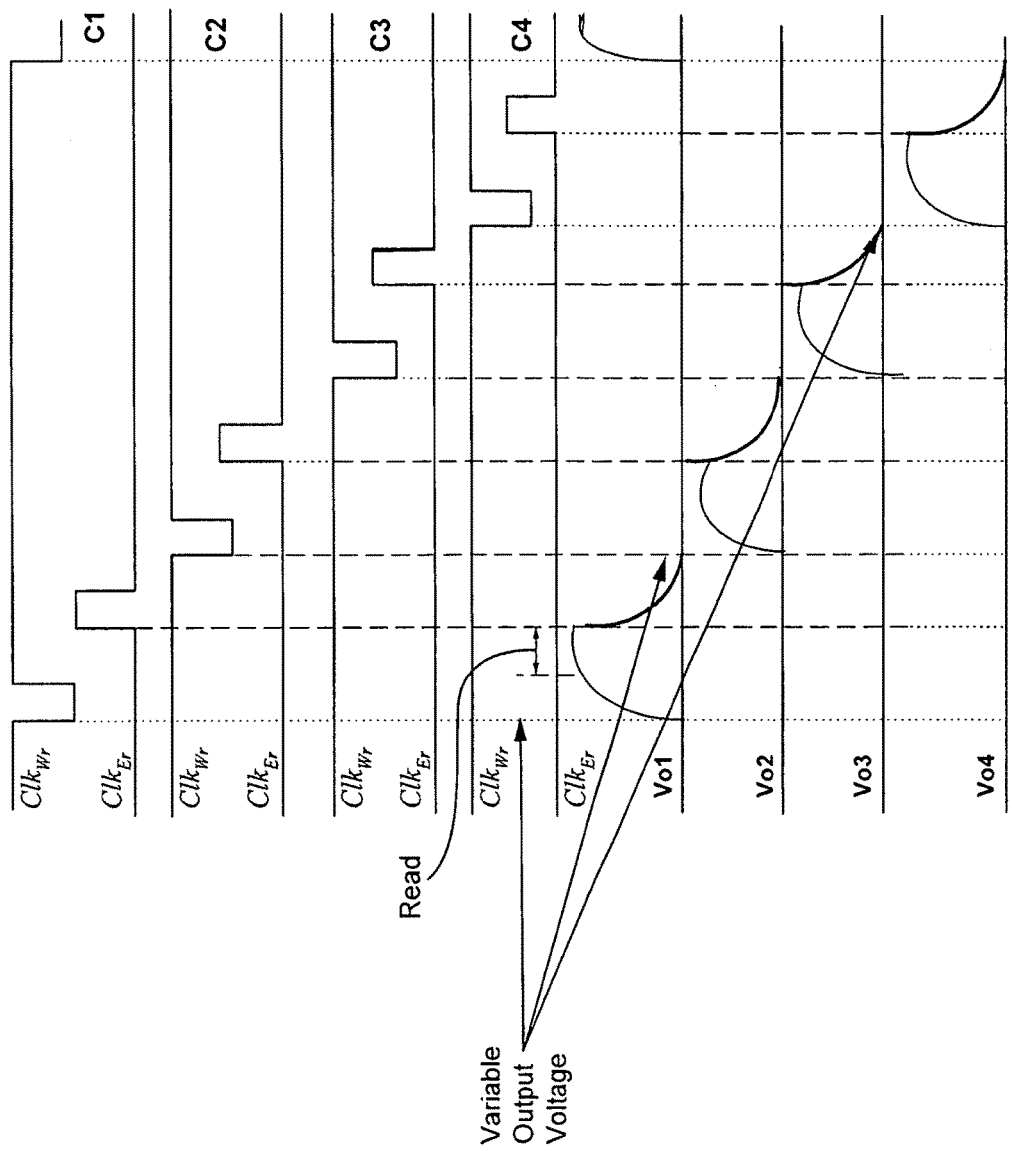
FIG. 6 is an exemplary timing diagram derived from readout circuitry of FIGS. 4-5.

Still referring to FIG. 4, during a write phase a write pulse $Clk_{wr}$ is input to the gate of transistor Q7, which functions like a resistor or switch, charging one or more of the capacitors C1-C4 of the sensor capacitance $C_s$. FIG. 6 includes certain signals used in the FIG. 4 circuit in the write cycle. In the write cycle, Transistor Q1 is in a saturated mode, since its gate and drain are connected, so that Q1 is on. Q4, Q5 and Q6 are turned off, and Q2 is on during the write mode. Transistors Q3 and Q4 are optional. When Q7 is turned on by the write pulse, we have a write cycle, and Vcc appears at Cs via A and charges one or more of the capacitors C1-C4 of the sensor capacitance Cs. $V_{cc}$ may be a constant voltage, such as 5V, in certain example embodiments. One or more of the capacitors C1-C4 may be charged at a time during a write cycle. However, in certain example embodiments of this invention, the circuit charges and reads the capacitors C1, C2, C3 and C4, one at a time (e.g., see FIG. 6). Thus, during one write cycle, only one of the capacitors C1, C2, C3 or C4 is charged in certain example embodiments of this invention.

The above process described for the left side of the FIG. 4 sensing circuit is essentially mirrored on the opposite or right side of the FIG. 4 circuit. As current flows through the left-side branch, current also flows at B through the right-side branch, and changes to $C_s$ are mimicked, or substantially mimicked in internal mimicking capacitance $C_{int}$. When Q7 is turned on, current also flows through Q2 (which is on) and charges $C_{int}$ using Vcc. Thus, the charging of one of the capacitors C1-C4 is mimicked by the charging of capacitor $C_{int}$. In other words, $C_{int}$ is charged to the same degree, or substantially the same degree, as the capacitor (e.g., C1) being charged on the other side of the FIG. 4 circuit. The output voltage of the FIG. 4 circuit, Vout (or Vo), is based on $C_{int}$ and is taken at or proximate an electrode of the capacitor $C_{int}$ as shown in FIG. 4. An example formula reflecting Vout (or Vo) is shown at the bottom of FIG. 4. Accordingly, it will be appreciated that the output Vout (or Vo) of the FIG. 4-5 circuit is related to and based on the capacitors C1-C4 of the sensor Cs. More specifically, the output Vout of the FIG. 4-5 circuit is related to and indicative of the status of capacitors C1-C4 and the effects on those capacitors of moisture on the exterior window surface, even though Vout is not taken directly from capacitors C1-C4. In particular, Vout (or Vo) is read out during the write cycle, due to the write pulse shown in FIG. 4 (see also FIG. 6). In the formula at the bottom of FIG. 4 for Vout, W1 is for Q1, W2 is for Q2, L1 is for Q1, L2 is for Q2, where W is transistor channel width, and L is transistor channel length; and $V_T$ is a threshold voltage of each MOSFET. It is noted that in alternative embodiments of this invention, the output Vout of the circuit may be taken directly (instead of indirectly via $C_{int}$) from the sensing capacitors C1-C4.

Transistors Q3 and Q4 are optional. In certain example embodiments, these transistors may be at low voltages (e.g., off) during the write phase, and on during the erase phase.

The output signal Vout (or Vo) of the FIG. 4 (and FIG. 5) sensing circuit is sigma-delta modulated in certain example embodiments of this invention. Sigma-delta modulators, which can be used in a sigma-delta digital-to-analog converter (DAC), can provide a degree of shaping or filtering of quantization noise which may be present. Example sigma-delta modulators that may be used are described in U.S. Pat. Nos. 6,975,257, 6,972,704, 6,967,608, and 6,980,144, the disclosures of which are hereby incorporated herein by reference. In certain examples of sigma-delta conversion, oversampling, noise shaping and/or decimation filtering may be brought to bear. Example advantages of sigma-delta modulation include one or more of: (i) analog anti-aliasing filter requirements are less complex and thus may be cheaper than certain example nyquist based systems; (ii) sample and hold circuitry may be used due to the high input sampling rate and low precision A/D conversion; (iii) since digital filtering stage(s) may reside behind the A/D conversion, noise injected during the conversion process such as power-supply ripple, voltage reference noise and noise in the A/D converter itself may be controlled; (iv) since the sigma-delta converter may be essentially linear it may not suffer from appreciable differential non-linearity and/or background noise level(s) may be independent of input signal level. Improved S/N ratios may be realized.

Figure 5:
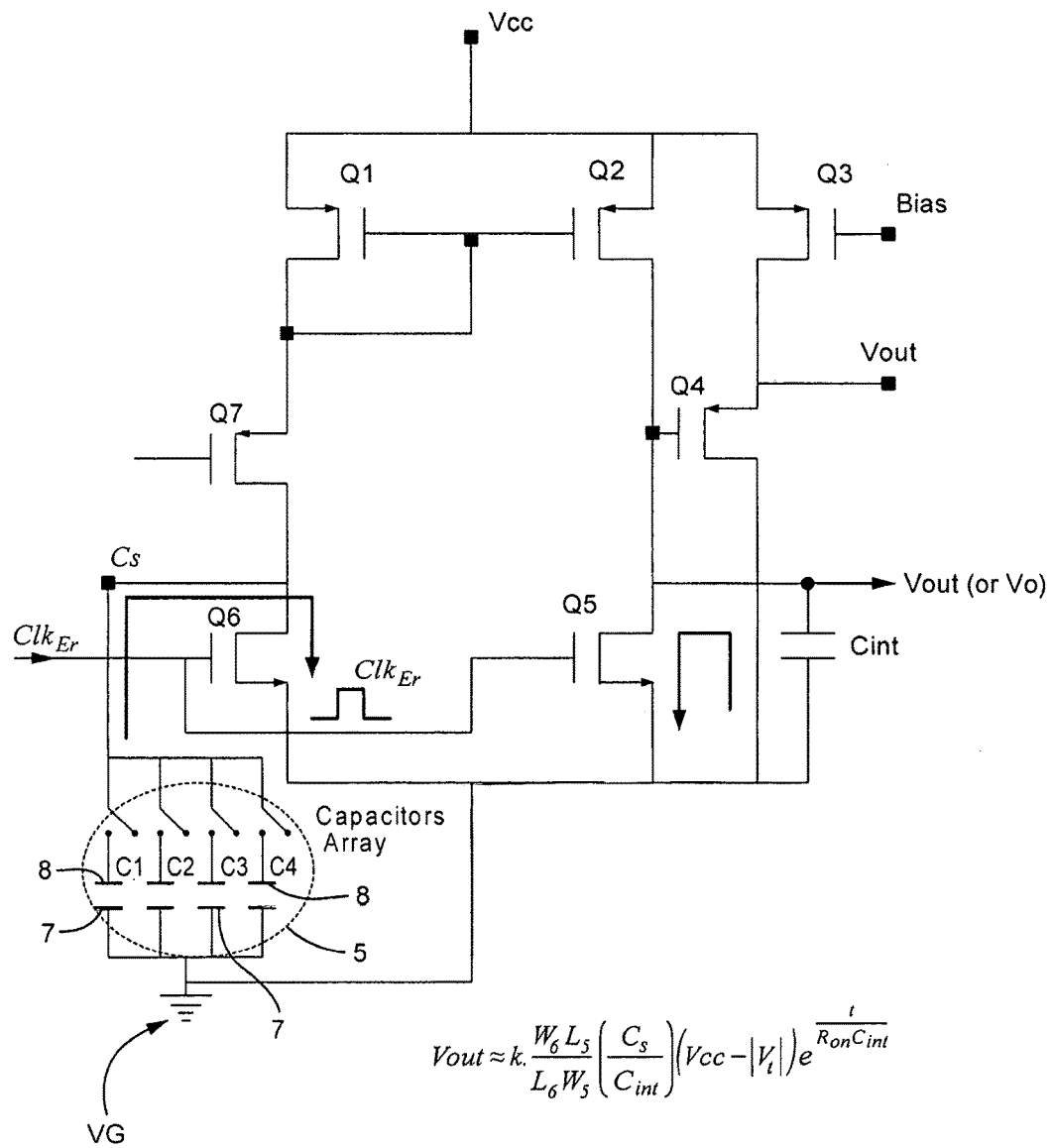
FIG. 5 is an example circuit diagram including exemplary circuitry used for an erase clock pulse in readout electronics, for use in one or more of the embodiments of FIGS. 1(a)-1(f), 4 and 6-12 for example.

FIGS. 4-5 illustrate switches for selectively coupling the various capacitors C1-C4 to the rest of the circuit. The circuit may read out signals from all of the capacitors C1-C4 simultaneously, or alternatively may only read out signals from one capacitor at a time selected from C1-C4, or as a further alternative may read out signals from a combination of some but not all of capacitors C1-C4 at a given point in time. An example non-limiting switching circuit for selective coupling the read-out electronics to one or more of capacitors C1-C4 as needed or as desired in discussed below in connection with FIG. 31.

Figure 25:
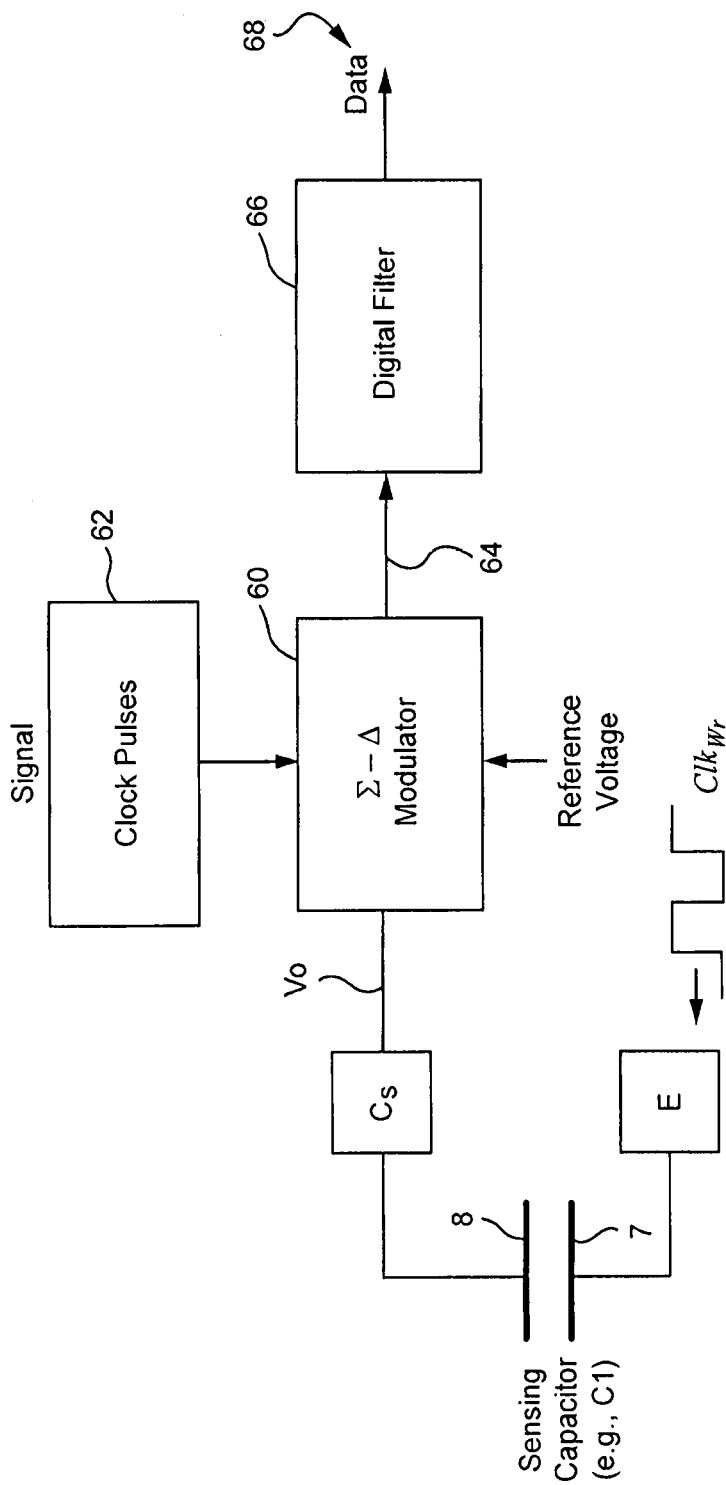
FIG. 25 is a block diagram illustrating circuitry and/or processing of signals according to an example embodiment of this invention where a sensing capacitor (e.g., C1) is present, including sigma-delta modulation.
Figure 26:
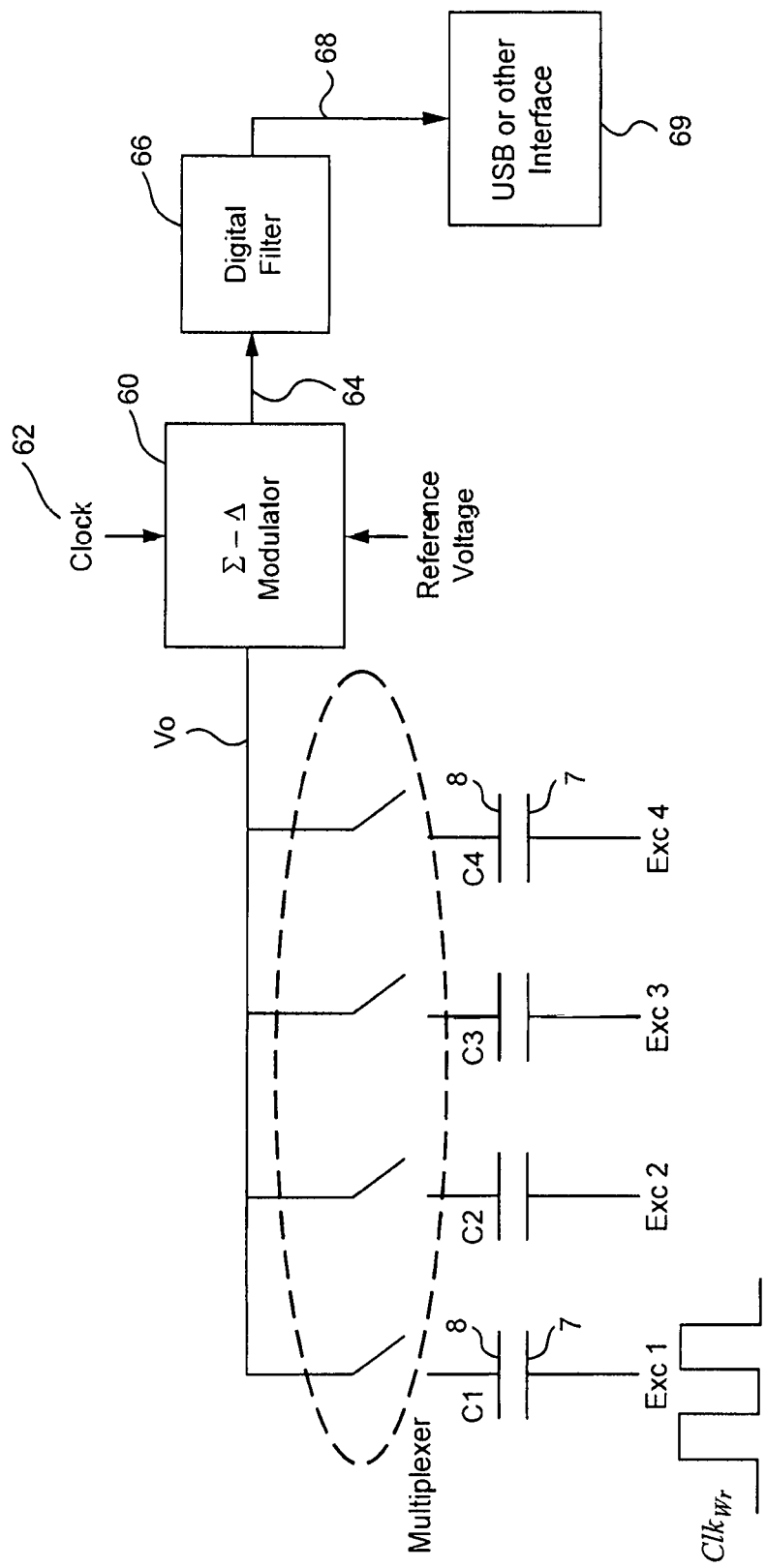
FIG. 26 is a block diagram illustrating circuitry and/or processing of signals according to an example embodiment of this invention where a plurality of capacitors (e.g., C1-C4) are present, including sigma-delta modulation.

FIG. 25 which is a simplified version of a sigma-delta modulator system according to an example embodiment of this invention, for modulating and/or converting the output signal Vout (or Vo) of the FIG. 4 (and FIG. 5) circuit. In FIG. 25, a write pulse (see pulse at the bottom of FIG. 25), is used to charge the sensing capacitor (C1, C2, C3 or C4) as explained above with respect to FIG. 5. The square wave excitation (e.g., for writing and/or erasing cycles) is used on the sensing capacitor to charge and discharge it. This process is mirrored or mimicked, for $C_{int}$ as explained herein. The output signal Vout (or Vo) of the FIG. 4 circuit is sigma-delta modulated by sigma-delta modulator 60. The modulator 60 make take the form of a hardware circuit, firmware, and/or software in different example embodiments of this invention. Clock pulses 62 from a clock are input to the modulator 60, which trigger the latch of a quantizer of the modulator 60. After the output signal Vout (or Vo) are sigma-delta modulated by modulator 60, the modulated signals 64 are forwarded to an optional digital filter 66 (e.g., lowpass filter or the like). Digital filter 66 processes the sigma-delta modulator digital output 64, which is a stream of 0 s and 1 s. The data is then scaled appropriately using calibration coefficient(s). The filtered data 68 is then read through a serial interface 69 or the like and sent to a computer which does the correlation calculations for chunks of data packets. Thus, the data from the interface 69 is then correlated (e.g., autocorrelated and/or cross-correlated) as explained herein. FIG. 26 is similar to FIG. 25, except that FIG. 26 illustrates an array of sensing capacitors C1-C4 which are multiplexed via a multiplexer. The multiplexer shown in FIG. 26 may be used for selectively coupling the various capacitors C1-C4 to the rest of the circuit including modulator 60. The circuit may read out signals from all of the capacitors C1-C4 simultaneously via multiplexer, or alternatively may only read out signals from one capacitor at a time selected from C1-C4, or as a further alternative may read out signals from a combination of some but not all of capacitors C1-C4 at a given point in time. An example non-limiting switching circuit for use in the position of the multiplexer shown in FIG. 26, for selectively coupling the read-out electronics to one or more of capacitors C1-C4 as needed or as desired, in discussed below in connection with FIG. 31.

Figure 27:
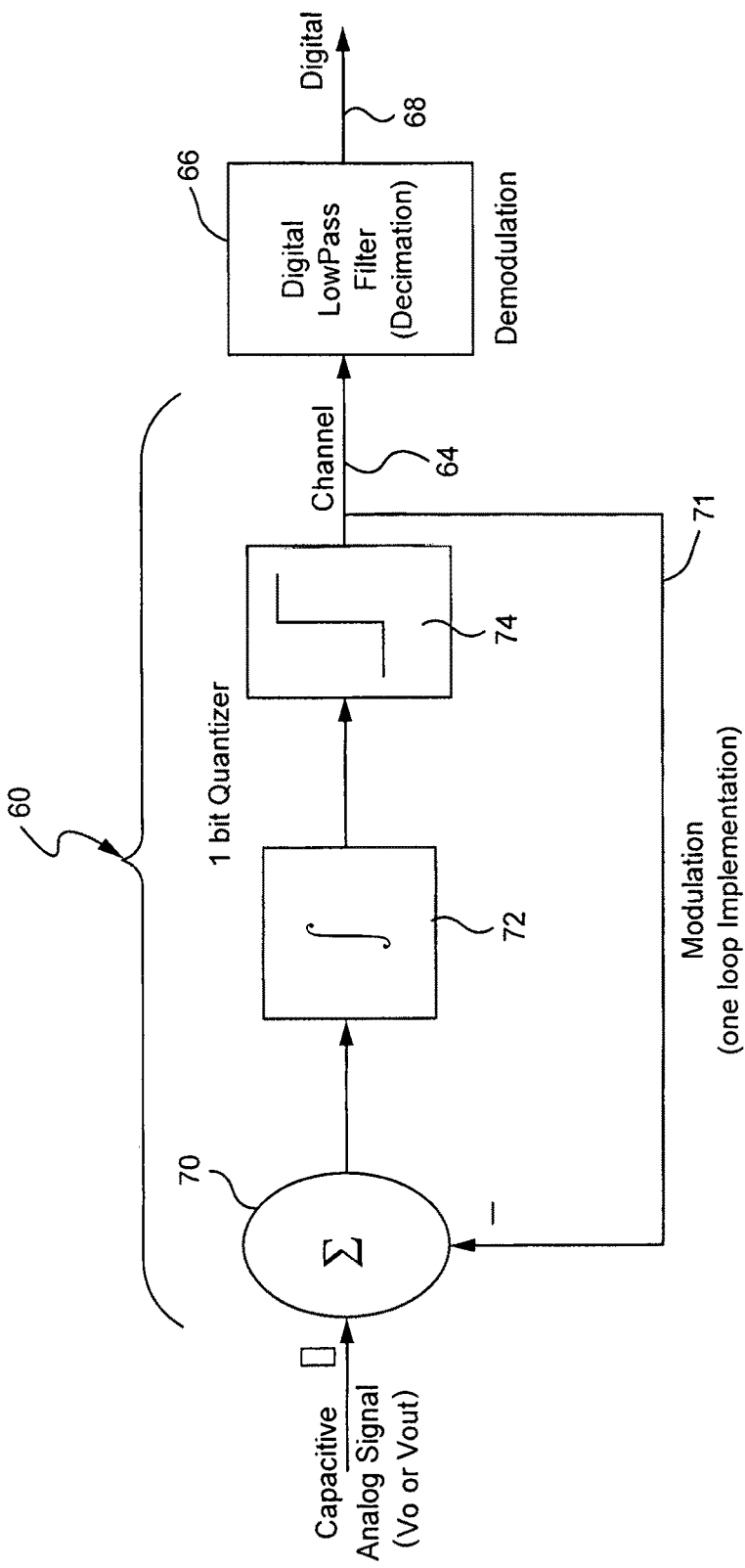
FIG. 27 is a block diagram illustrating sigma-delta modulation according to an example embodiment of this invention; this processing being performed in circuitry, firmware and/or software.

FIG. 27 is a block diagram illustrating an example of sigma-delta modulation which may be performed in the modulator 60 of FIGS. 25-26. Again, this modulation may be performed by circuitry, firmware and/or software in different example embodiments of this invention. The analog output signal Vout (or Vo) of the FIG. 4 (and FIG. 5) circuit is received by a summer 70 of the sigma-delta modulator 60. Adder or summer 70 receives the analog Vout (or Vo) signal as well as a feedback signal from a feedback loop 71 of the modulator 60. The output of adder or summer 70 is received by integrator 72 whose output is received by a quantizer 74 such as a one bit quantizer. The digital output 64 is then filtered 66 as explained above, and so forth. The sigma-delta modulation is advantageous in that it provides oversampling and allows noise such as EMI to be treated and its adverse effects reduced. In particular, the noise is spread by the sigma-delta modulation out over the frequency band so that the signal-to-noise (S/N) ratio can be improved.

Figure 29:
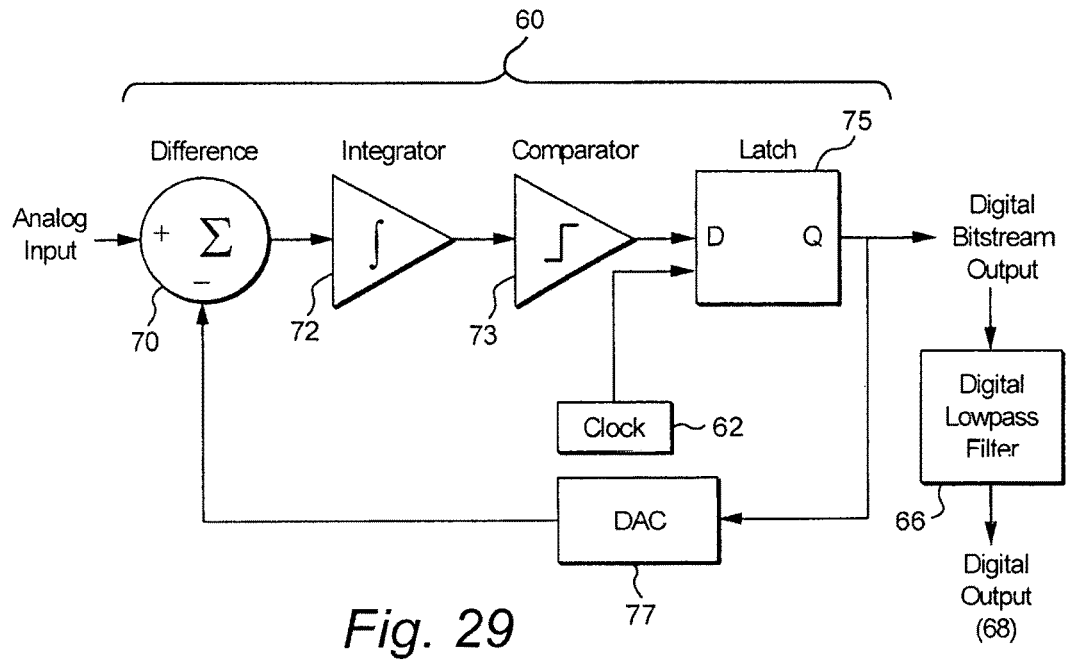
FIG. 29 is a block diagram illustrating sigma-delta modulation according to another example embodiment of this invention; this processing being performed in circuitry, firmware and/or software.

FIG. 29 illustrates another example of a sigma-delta modulation according to an example of this invention. The sigma-delta modulator of FIG. 29 receives an analog input from the FIG. 4, 5 sensing circuit that reaches adder or summer 70. Adder 70 determines the difference between a feedback signal and the input, and its output is forwarded to integrator 72. The output of the integrator 72 is sent to comparator 73. Comparator 73 decides whether its input is higher or lower than a predetermined threshold and can put out a single bit signal based on the same, a bitstream, to the latch 75 (note that quantizer 74 in FIG. 27 may include each of comparator 73 and latch 75). The comparator's output is received by latch 75 for sampling. A way to reduce noise is to increase clock rate from clock 62; e.g., a sampling rate of at least twice the maximum input frequency, with further increases referred to as oversampling rate. The digital bitstream output from the latch is received by the lowpass digital filter 66. The lowpass filter is used because it is sometimes desired to gain the average signal level out of the bitstream. The digital output may be a single-bit serial signal with a bit rate much higher than the data rate, and its average level may represent an average input signal level. The feedback loop, like the one in FIG. 27, includes a digital-to-analog (DAC) converter 77 that may be of the one-bit type or any other suitable type. The filtered data 68 is read through a serial interface 69 or the like and sent to a computer which does the correlation calculations for chunks of data packets.

Figure 30:
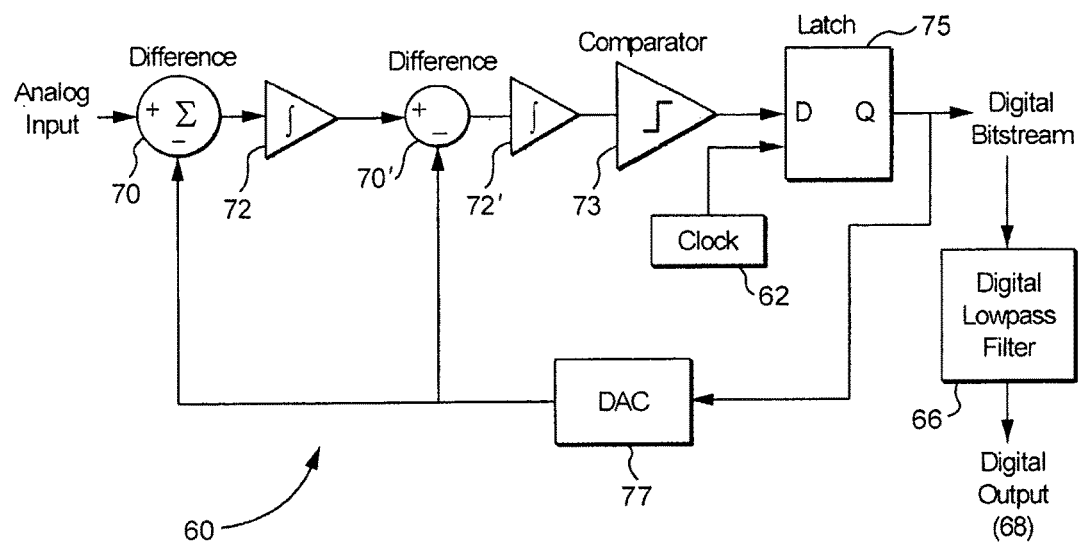
FIG. 30 is a block diagram illustrating sigma-delta modulation according to yet another example embodiment of this invention; this processing being performed in circuitry, firmware and/or software.

FIG. 30 illustrates another example of a sigma-delta modulation according to an example of this invention. The sigma-delta modulator of FIG. 30 receives an analog input from the FIG. 4, 5 sensing circuit that reaches first adder or summer 70. The FIG. 30 sigma-delta modulator scheme is the same as that of FIG. 29 discussed above, except that a second adder or summer 70' and a second integrator 72' are provided in the modulator of the FIG. 30 embodiment.

Referring back to FIG. 4, each capacitor (C1, C2, C3, C4) is discharged before charging the next, in certain example embodiments of this invention. The process of discharging each capacitor is described in connection with the erase pulse, with respect to FIGS. 5-6.

FIG. 5 is a circuit diagram of the FIG. 4 sensing circuit, with respect to an erase cycle. During an erase cycle, a previously charged capacitor (C1, C2, C3 and/or C4) is discharged before the next write cycle. FIG. 6 includes example signals used during the erase cycle(s). No reading is performed during the erase phase, in certain example instances. During an erase cycle or phase, Q7 is turned off (the write pulse $Clk_{Wr}$ is not present), and transistors Q5 and Q6 are turned on by an erase pulse $Clk_{Er}$ (see also FIG. 6). Thus, the capacitor (C1, C2, C3 and/or C4) discharges to ground (e.g., V=0) or virtual ground (VG), as does $C_{int}$. Again, $C_{int}$ mimics the capacitance of the sensor Cs. Once the capacitances Cs and $C_{int}$ have been connected to ground and discharged, the erase pulse and cycle ends. Then, the next capacitor (C1, C2, C3 or C4) in the sequence can be prepared, charged, and read.

Thus, referring to FIGS. 4-6, it will be appreciated that according to certain example embodiments of this invention a rain sensor comprises: a sensing circuit comprising at least first and second sensing capacitors (e.g., C1 and C2) that are sensitive to moisture on an external surface of a window, and at least one mimicking capacitor ($C_{int}$) that mimics at least charging and/or discharging of at least one of the first and second sensing capacitors; wherein a writing pulse ($Clk_{Wr}$) causes at least the first sensing capacitor (e.g., C1) to be charged, and an erasing pulse ($Clk_{Er}$) causes each of the first sensing capacitor (e.g., C1) and the mimicking capacitor ($C_{int}$) to substantially discharge; wherein presence of rain on the external surface of the window in a sensing field of the first sensing capacitor (e.g., C1) causes a voltage (see Vo or Vout) at an output electrode of the mimicking capacitor ($C_{int}$) to fluctuate in a manner proportional to fluctuation of voltage at an output electrode (8) of the first sensing capacitor (e.g., C1), even though the rain is not present in a field of the mimicking capacitor ($C_{int}$); and wherein rain is detected based on an output signal (see Vo or Vout) from the output electrode of the mimicking capacitor ($C_{int}$), wherein the output signal is read at least between an end of the writing pulse ($Clk_{Wr}$) and a beginning of the erase pulse ($Clk_{Er}$) (see the "read" area in FIG. 6).

Still referring to FIG. 5, in certain example embodiments of this invention, during the erase cycle, the erase pulse $Clk_{Er}$ causes the capacitor (C1, C2, C3 and/or C4) and thus also the mimicking capacitance $C_{int}$ to discharge to ground (e.g., a fixed potential such as V=0) (see the conventional ground symbol in FIG. 5). However, in other example embodiments of this invention, it has been found that a fixed ground can lead to certain problems. Thus, in such other example embodiments of this invention, during the erase cycle the erase pulse $Clk_{Er}$ causes the capacitor (C1, C2, C3 and/or C4) and thus also the mimicking capacitance $C_{int}$ to discharge to a virtual ground VG that is floating (see VG and the ground symbol in FIG. 5). Stated another way, an electrode of each of capacitors C1-C4 is floating. It may be at a floating or reference potential/voltage. It has been found that a floating or virtual ground can be highly advantageous in certain example embodiments of this invention (e.g., a floating ground and/or capacitor electrode(s) can lead to a significant reduction in EMI interference problems). For example, such a floating or virtual ground may help reduce the chance of the sensor system being tricked by EMI interference. In this respect, reference is made to FIGS. 28(*a*) and 28(*b*) (along with FIG. 5).

Figure 28A:
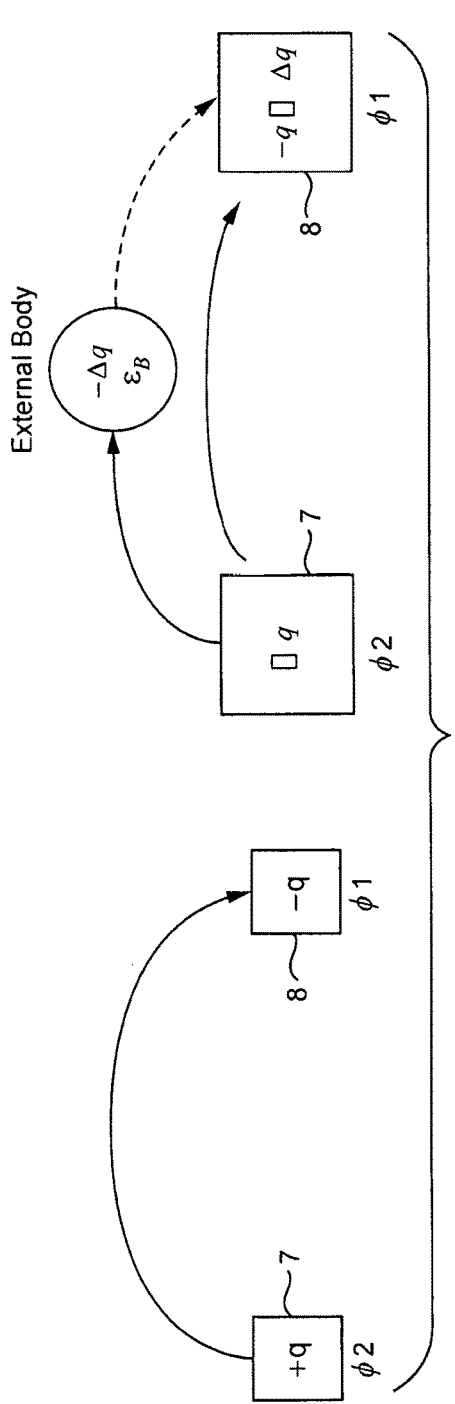
FIGS. 28(a) AND 28(b) are schematic diagrams illustrating advantages of using floating electrodes for sensing capacitors (e.g., C1-C4) according to certain example embodiments of this invention.
Figure 28B:
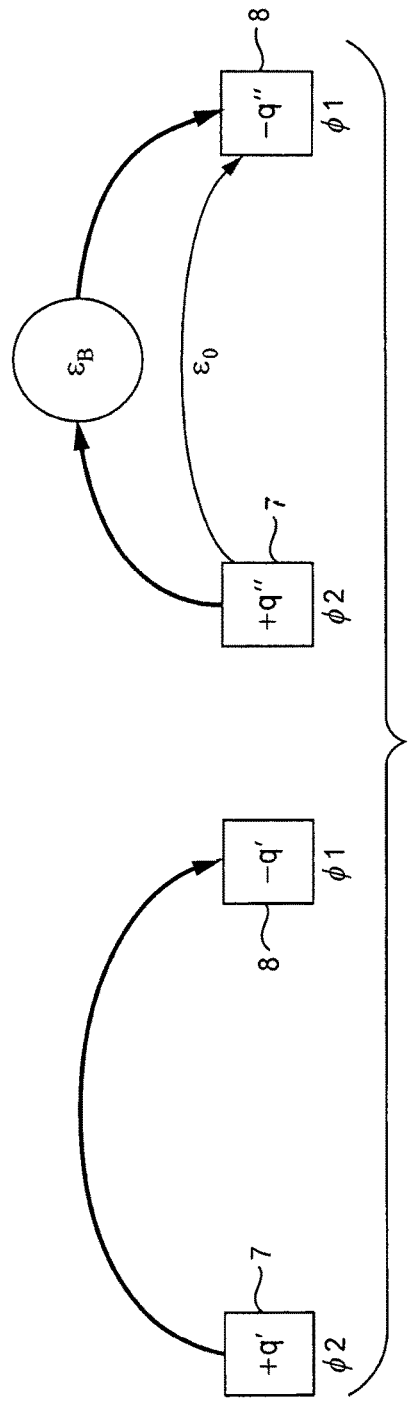

In FIGS. 28(*a*)-(*b*), reference numerals 7 and 8 refer to the electrodes of a capacitor (e.g., C1, C2, C3 or C4). In these figures, "q" refers to charge and Φ refers to potential (Φ1 is different than Φ2). In FIG. 28(*a*) the capacitor (e.g., C1) is grounded at a fixed potential such as 0 volts (the charge at grounded electrode 7 is fixed at +q). In this respect, when the charge at grounded electrode 7 is fixed at +q, when one brings an external body $E_B$ (e.g., human finger with a higher dielectric constant) into a sensing area of the capacitor (e.g., touching the front surface of the windshield over the capacitor) this external body induces a change in charge –Δq and the other electrode 8 which is not fixed changes from a charge of –q to a charge of –q. +Δq in an attempt to balance charge. Thus, if one were to ground the capacitor at a fixed potential such as 0 volts, and read an output voltage of the capacitor, one would read charge changes caused by Δq which is not needed, and this may lead to false readings. Comparing FIGS. 28(*a*) and 28(*b*), FIG. 28(*b*) illustrates an advantage of causing an electrode 7 of the sensing capacitor (e.g., any of C1-C4) to be floating (e.g., at a floating or virtual ground). In FIG. 28(*b*), the charge q at electrode 7 is not fixed. E.g., the charge at electrode 7 changes from +q' to +q" when the external body comes into contact with the windshield at a sensing area of the capacitor, thereby indicating the floating nature of the electrode. In FIG. 28(*b*), when the external body (e.g., human finger) is applied to the windshield over the capacitor sensing area the free charges on both electrodes 7 and 8 of the capacitor change. Thus, the adverse effect of Δq is eliminated or reduced by using the floating or virtual ground VG (electrode 7 is floating). In particular, when electrode 7 is floating as in FIG. 28(*b*), the external body ($E_B$) does not adversely affect summation of charge because adding the charges (+q" and –q") of the electrodes 7 and 8 when the external body is present gives zero or substantially zero. False readings due to EMI interference can also be reduced by using this floating feature. Thus, in certain example embodiments, the floating nature may allow the absolute values of the charges q at capacitor electrodes 7 and 8 to be the same or substantially the same even when the external body is present since the electrode 7 is floating and is not fixed at ground. This is one example reason why it may be advantageous to cause the electrodes 7 of the capacitors C1-C4 to be floating, or be at a virtual ground VG as shown in FIG. 5. Thus, referring to FIGS. 5 and 28, the sensing capacitors C1-C4 are floating and both electrodes thereof are isolated from ground. Accordingly, according to certain example embodiments of this invention, the rain sensor comprises at least one sensing capacitor (C1, C2, C3 and/or C4) that is sensitive to moisture on an external surface of a window, the sensing capacitor including a first capacitor electrode (8) that receives a charging signal and a second capacitor electrode (7) spaced apart from the first capacitor electrode (8); and wherein the second capacitor electrode (7) is floating so that the sensing capacitor is isolated from ground.

FIG. 6 is an exemplary timing diagram of signals applied to or read out from the FIG. 4-5 circuit during the write and erase modes/cycles. As noted above, the capacitors (C1-C4) are sequentially charged, read, quantized, and erased. FIG. 6 shows a clock write ($Clk_{Wr}$) and erase ($Clk_{Er}$) pulse for each capacitor C1-C4, in sequence. Then, voltages are quantized and output. Variable output voltage Vo1-Vo4 correspond to capacitors C1-C4 respectively, and thus $C_{int}$. It is noted that the output signals Vo1-Vo4 in FIG. 6 are taken at $V_{out}$ (or Vo) in FIGS. 4-5. Moreover, in FIG. 6, the output signals Vo are read or analyzed (e.g., for autocorrelation and/or cross-correlation) at the peak read areas (see "Read" in FIG. 6) of the output signals where the output signals are substantially stabilized and/or the capacitor saturated. In particular, the output signal $V_{out}$ (or Vo) in FIG. 6 for a particular capacitor (C1) is read in the "read area" after the end of the write pulse ($Clk_{Wr}$) for that capacitor, and before and/or up to the beginning of the erase pulse ($Clk_{Er}$) for that capacitor.

Still referring to FIG. 6, for example, a drop of water on the exterior surface of a windshield will affect the magnitude of the output signal(s) $V_{out}$ (or Vo). For instance, a water drop over the area of a given capacitor (e.g., C1) will cause the level of the output signal(s) $V_{out}$ (or Vo) for that capacitor in the "read" area of the signal to be higher compared to a situation where no such drop was present. The exact magnitude or level depends on the size of the water drop. With increasing water amounts, the magnitude of the signal at the "read" area gets higher because the dielectric constant of water is higher than that of glass and/or air and this causes the capacitance to increase. In a similar manner, if no water drop is present on the windshield over the area of a given capacitor (e.g., C1) then this will cause the level of the output signal(s) $V_{out}$ (or Vo) for that capacitor in the "read" area of the output signal to be lower compared to a situation where a drop was present.

The signals (e.g., from the capacitor(s)) may be converted from analog-to-digital via a sigma-delta modulation scheme or the like, which may be implemented at the software level or in any other suitable manner such as via hardware. The principle behind sigma-delta architecture is to make rough evaluations of the signal, to measure the error, integrate it, and then compensate for that error. Data may be over-sampled at a given rate of at least 32 kHz, e.g., more preferably 64 kHz, though it will be appreciated that other sampling rates may be used. The course quantization can be recovered by the sigma-delta modulation scheme to produce a simple binary 0 or 1 output, corresponding to on and off, respectively. Thus, the sigma-delta modulation scheme may be used to reduce noise (e.g., at the tail of the signal) and produce a digital output stream (e.g., 1 s and 0 s).

Figure 7:
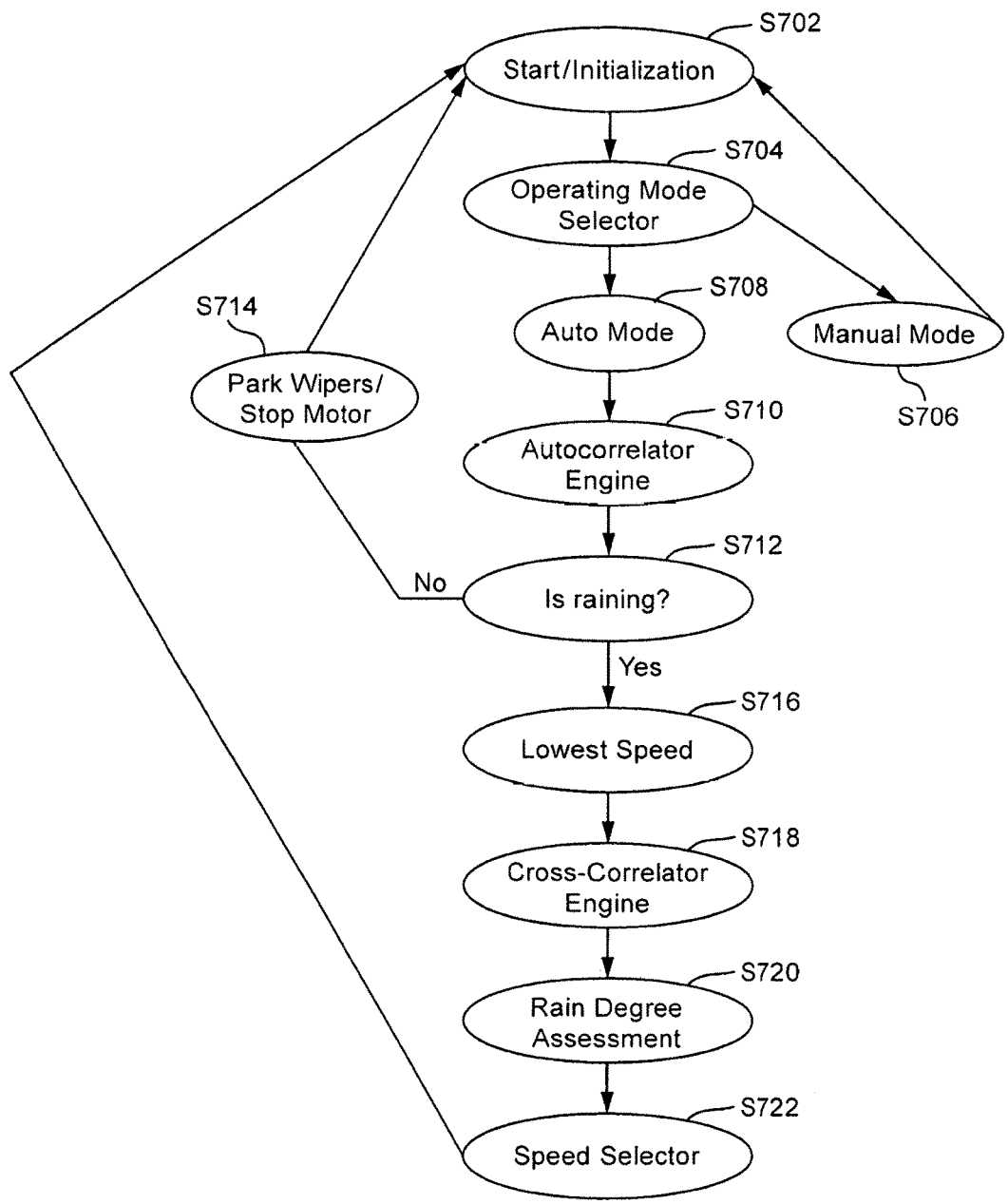
FIG. 7 is an exemplary flowchart or state diagram showing how autocorrelation and cross-correlation data may be used to control wipers according to an example embodiment of this invention, which may be used in conjunction with one of more of FIGS. 1-6 and 8-12.

Before discussing the detailed operation of and example mathematics behind an example sensor algorithm, an overview of the states in which the sensor and/or wipers can take will be given in connection with FIG. 7, which is an exemplary state diagram showing how autocorrelation and cross-correlation data may be used to control vehicle wipers. The system begins in Start/Initialization State S702. In this state, all buffers are cleared in certain example instances. Based on the inputs of capacitors $C_1, C_2, \ldots, C_n$, analog-to-digital conversion of the signals from the respective inputs is accomplished via sigma-delta modulation. Data is read for the plurality of channels over time period T. Operating Mode Selector State S704 functions as a switch to select between the manual or automatic wiper mode. If Operating Mode Selector State S704 indicates that manual mode is selected, then in Manual Mode State S706 an auto mode may be disabled and a pre-existing manual mode enabled. Then, the system returns to Start/Initialization State S702. However, if Operating Mode Selector State S704 indicates that auto mode is selected, the automatic wiper mode is enabled in Auto Mode State S708.

In Autocorrelator Engine State S710, at least three computations are performed. First, a normalized autocorrelation is calculated for each signal input of the capacitive array. Second, the gradient of the autocorrelation is calculated. Third, the difference between the signal input and a reference non-disturbed signal ($\Delta_1$) may be calculated. This information is passed to Is Raining? State S712, in which at least three conditions are checked to determine whether it is likely that it is raining, there is moisture on the windshield, etc. Likely indications of rain are that the gradient of the autocorrelation is greater than 1, all autocorrelation values are positive, and/or $\Delta_1$ is greater than some pre-defined threshold value t1. If these conditions are not met, the system moves to Park Wipers/Stop Motor State S714, where wipers are parked (if they are moving) or not actuated, and the motor is stopped (if it is engaged), and the system is returned to Start/Initialization State S702.

On the other hand, if all conditions are met (e.g., it is likely that there is an interaction of water, moisture or some other perturbation on the glass, etc.), the system moves to Lowest Speed State S716, in which the wiper motor is activated at the lowest speed available. In Cross-Correlator Engine State S718, the cross-correlation between the input signals from the capacitors is calculated. The cross-correlation curve shape is determined, and the symmetry of the two sides of the cross-correlation curve are checked for symmetry. As will be described below, these checks help, for example, to determine the type of perturbation (e.g., light rain, heavy rain, fog, snow, etc.) hitting the window (e.g., windshield). In Rain Degree Assessment State S720, the "degree of rain" (e.g., heavy, light, etc.) is determined. Based on this determination, the wiper motor is activated at the appropriate speed in Speed Selector State S722. Lastly, the system is returned to Start/Initialization State S702 to determine whether there is any change in conditions outside the car.

Figure 8:
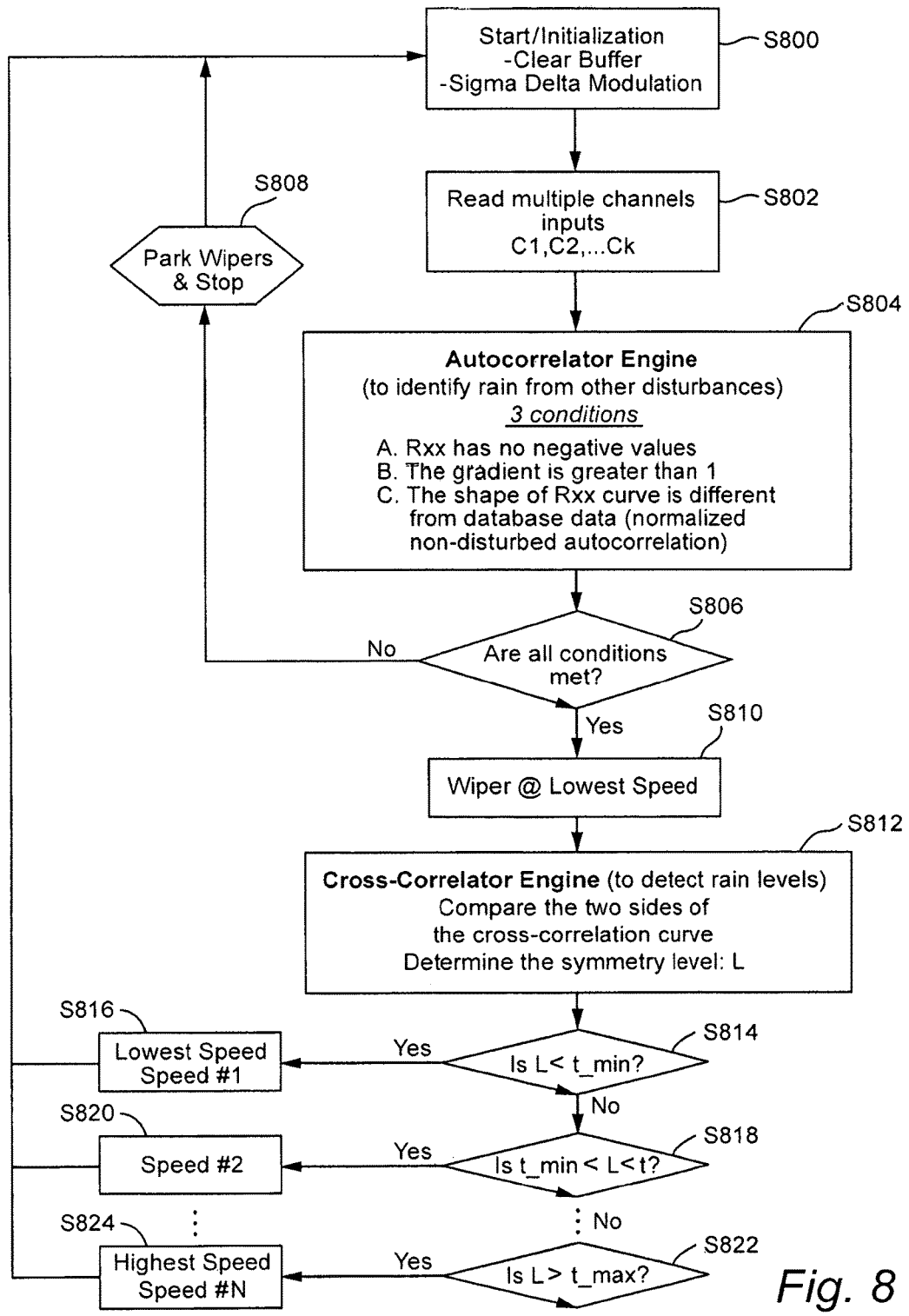
FIG. 8 is an exemplary flowchart showing how autocorrelation and cross-correlation data can be used to control wipers according to an example embodiment of this invention, which may be used in conjunction with one of more of FIGS. 1-7 and 9-12.

The steps performed by the rain sensor will be described in greater detail in connection with FIG. 8, which is an exemplary flowchart showing how autocorrelation and cross-correlation data can be used to control wipers in certain example embodiments of this invention. In FIG. 8, in step S800 buffers are cleared, and data outputted from the FIG. 4-5 circuit (e.g., from $C_{int}$, or from capacitors C1-C4) is sigma-delta modulated, and is read in S802.

The algorithm for determining whether to engage wipers and, if so, the speed at which to engage wipers begins by autocorrelating the sigma-delta modulated data in step S804. Autocorrelation may be used for analyzing functions or series of values, such as time domain signals. An autocorrelation is the cross-correlation of a signal with itself. Autocorrelation is used for finding repeating or substantially repeating patterns in a signal, such as, for example, determining the presence of a periodic signal buried under noise, identifying the fundamental frequency of a signal that does not actually contain that frequency component but implies within it with many harmonic frequencies, etc. Cross-correlation is a measure of the similarity of two signals, and it is used to find features in an unknown signal by comparing it to a known one; in other words it may be used to perform signal fingerprinting in certain instances. Cross-correlation is a function of the relative time between the signals. In certain example embodiments of this invention, digital signals from any two capacitors (e.g., C1 and C2) are cross-correlated, in close spatial proximity, and the system looks for any degree of correlation at time lags other than a time lag of zero. This spatio-temporal cross-correlation allows the system to extract patterns in how the falling rain is electrically projecting itself over the sensor array. As an example, the system may take the case of rain drops moving over one capacitor C1 at a time t0 and the same drop "ringing" another capacitor C4 (spatially separated by distance L from C1). If the drop moves at an average speed Vi, the time (t0+T), where T=L/Vi, the cross-correlation function will have another extremum or kink. The normalized magnitude of this extremum value may allow the system to determine the degree of rain falling on the sensor.

Each capacitor C1-C4 has an autocorrelation function associated with the digitized Vout resulting from the readout thereof (or the corresponding readout of $C_{int}$). In example embodiments, the autocorrelation function depends on time difference, rather than on actual time. Computing autocorrelations is beneficial because it allows, for example, the deduction of the fundamental frequency irrespective of phase. Autocorrelations are advantageous over other methods, such as Fourier transforms (which may also be used in certain example embodiments of this invention) which provide information about the underlying harmonics only. Thus, the use of autocorrelation of the readouts from capacitors C1-C4 (which as explained above, includes the corresponding readouts from mimicking $C_{int}$) can be used to detect and distinguish between beads of water, dirt, dust, droplets, downpour, etc.

It is noted that herein data from $C_{int}$ is considered to be data from the capacitors C1-C4 because the capacitance $C_{int}$ mimics or substantially mimics the capacitances C1-C4 as explained above. Thus, when we talk about receiving data from the capacitors (e.g., C1-C4), this covers and includes receiving data from capacitance $C_{int}$. In other words, the output from the FIG. 4-5 circuit is considered to be from the capacitors C1-C4, even though it is not taken directly therefrom.

Rain, as a function of time, may be represented by the following formula:

$$b(\vec{r}, t) = \begin{cases} 1 & \text{rain projects electrically} \\ 0 & \text{otherwise} \end{cases}.$$

Essentially, b takes on a binary value indicating whether it is raining (1), or not (0). It will be appreciated that b is at least two bits, and that for sigma-delta modulation 24-bits may be used in certain example embodiments. It also will be appreciated that a scale could be introduced, potentially to capture more data related to the voltages in the capacitors C1-C4 (or $C_{int}$).

At the end of a sampling cycle L, for example, the output from the FIG. 4-5 circuit, e.g., from the array of four capacitors C1-C4 (or via $C_{int}$), ranges from 0000 to 1111 in certain example embodiments, using binary digital data. A single bit turned on can initiate a single wipe in certain example instances. In the case when all bits are off (0000) or all bits are on (1111), then no wipes may be initiated in certain example instances, because likely there is nothing on the windshield, the car is completely submerged, etc., since all capacitors in the array would be reading the same which is not consistent with rain falling on a window. Thus, the most probable events where wipers will be needed are those in the range of 0001 to 1110 (i.e., when the output from all capacitors in the array is not the same). When the data falls in this range, or even if it does not fall within this range, correlation functions (auto and/or cross correlation functions) may be performed using the following integral. It will be appreciated that the integral below can be rewritten in other forms, such as, for example, as a summation. The correlations between two drops over a large time period may be computed according to the following formula:

$$R_b(r_1, t; r_2, t_2) = \frac{1}{L}\int_0^L b(r_1, t_1 + t)b(r_2, t_2 + t)dt$$

$$R_b(r_1, t; r_2, t_2) = R_b(\Delta \vec{r}, \Delta t)$$

where $R_b$ is the correlation of a binary event, given as a function of the resistances $r_i$ at given times $t_i$; and L is a large sampling period during which a burst of data is captured. In certain example embodiments, the sampling period L may be from about 10 to 100 ms, and more preferably from about 20-30 ms, which corresponds approximately to the frequency an average human eye can discern. $R_b$ also is equal to a function of the correlation of the changes in resistances across capacitors $\Delta \vec{r}$ and the change in time. When $\Delta \vec{r} = 0$, the autocorrelation value is determined since data from the same capacitor is being analyzed, and when $\Delta \vec{r} \neq 0$, cross-correlations are computed since correlation is performed on data from different capacitors.

These functions are subject to several example constraints and underlying assumptions. First, $$\Delta \vec{r} = V \vec{i} \Delta t.$$

This constraint essentially means that a drop of water or the like is moving at a given time scale. Second, $$b(\vec{r} + V\vec{i}\Delta t, t+\Delta t) = b(\vec{r}, t).$$

This constraint mimics or substantially mimics what happens when drops of water or the like move from one capacitor to another. Thus, the correlation functions might be thought of as discrete steps p in space and T in time. This feature may be mathematically represented as the following equation:

$$R_b(m\vec{p}, nT) = R(V\vec{i}\Delta t, \Delta t)$$

Figure 9:
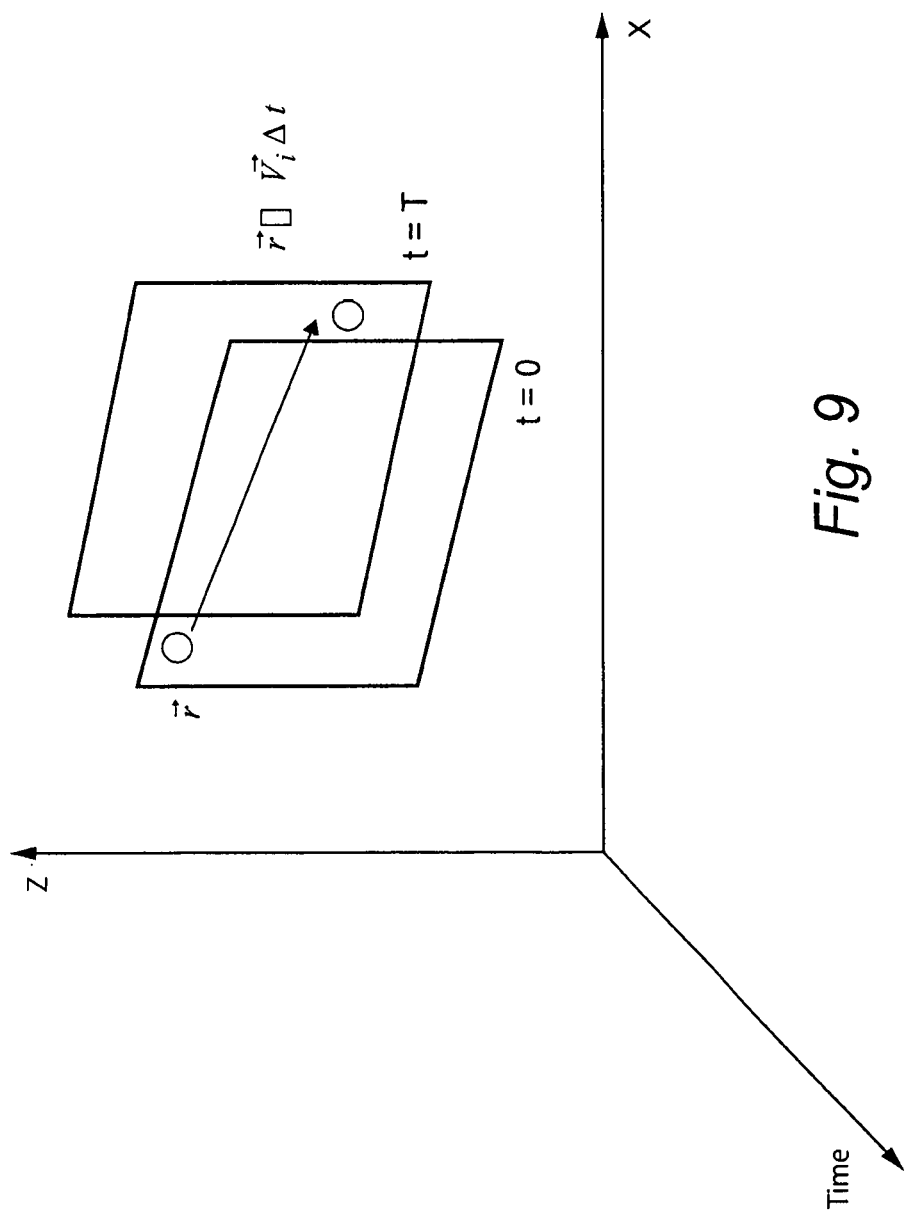
FIG. 9 is an exemplary stylized view of how a rain droplet might travel across a windshield.

Essentially, the left-hand side of the equation establishes a theoretical grid in space and time across which a drop of water or the like moves. For example, FIG. 9 is an exemplary stylized view of how a rain droplet might travel across a windshield. FIG. 9 shows a rain droplet moving across a windshield on the X-Z plane during an initial time period (t=0) and some late quantum of time (t=T). The assumption that drop distribution is uniform over space and time allows the creation of a binary field caused by rain that is in a wide sense stationary. The system also assumes that the temporal correlation between preferred pixels in the same neighborhood is high in the direction of rain. Lastly, the degree of autocorrelation and cross-correlation in time quantifies rain fall and other disturbances.

It will be appreciated that in certain example embodiments, computational time can be saved because of the nature of correlation matrices and the nature of rainfall. For example, correlation matrices may be symmetrical in certain example instances. Additionally, as another example, because rain tends to fall down from the sky and move up along a windshield, it may be sufficient to compare only capacitors that are disposed vertically relative to one another in cross-correlation, while ignoring horizontally adjacent capacitors.

It is noted that while binary data is used in certain example embodiments of this invention, this invention may also utilized grey scale data in certain example instances with respect to outputs from the circuit of FIGS. 4-5, or from similar or other suitable circuit(s).

After the autocorrelation has been performed in step S804 (e.g., using the equation(s) discussed above, or some other suitable correlation equation(s)), one or more checks may be performed to enhance the accuracy of the system. Examples of such checks (e.g., if the autocorrelated data Rxx has negative values, if a gradient is greater than one, and/or if the shape of a Rxx curve is different or substantially different from a normalized non-disturbed autocorrelation data stored in memory) are listed in the bottom part of the box for step S804 in FIG. 8. One, two or all three of these checks may be performed.

Figure 10:
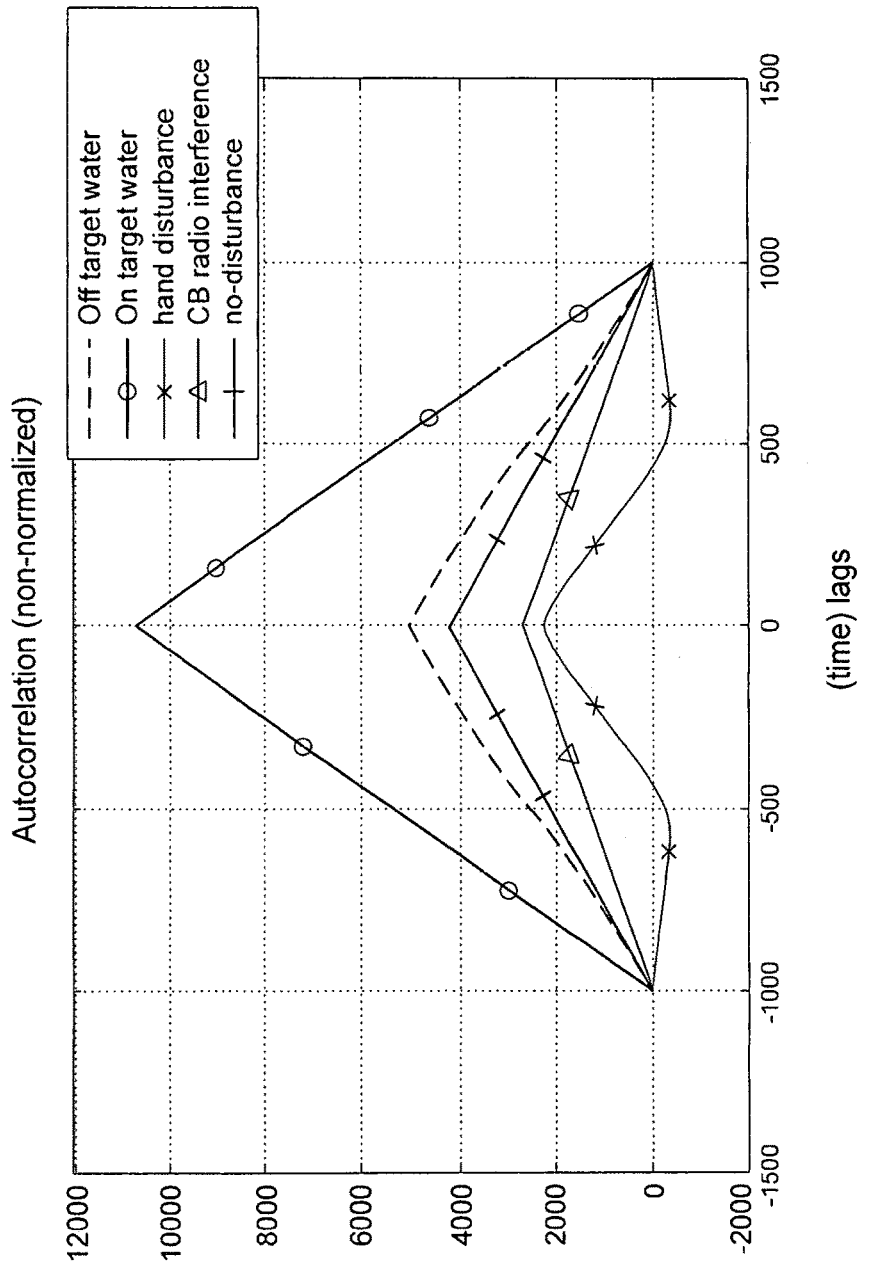
FIG. 10 is an graph plotting example experimentally-obtained maximum values of non-normalized autocorrelations for different disturbances.

For example, one check of the autocorrelation data in step S806 may be to determine whether the autocorrelated data from one or more of the capacitor(s) (C1, C2, C3 and/or C4; or via mimicking $C_{int}$) comprises negative values. For instance, when the autocorrelated data has negative value(s), then the system or method may indicate that it is not raining, may park the wipers, and/or may not actuate windshield wipers (see step S808). This check is for determining, for example, whether a detected disturbance is actually rain. In this respect, FIG. 10 is a graph plotting example experimentally-obtained maximum values of non-normalized autocorrelations for different disturbances. FIG. 10 illustrates that water signals are greater than non-disturbed signals and are positive, and that external interferences such as electromagnetic waves from CB radios and human hand touching of a window tend to be below the no-disturbance levels and may be negative. Thus, to eliminate or reduce false detections due to external disturbances such as, for example, a human hand touching the window, radio signal interference, etc., any signal with negative autocorrelation values is considered a "no-rain" event. It will be appreciated that some example embodiments may consider negative autocorrelation values. Other example embodiments may take other measures to eliminate or reduce false detections due to external interferences by, for example, comparing gradients (e.g., any curve lower or less than the no-disturbance curve/plot of FIG. 10 may be considered a "no-rain" event), shielding capacitors, etc.

A second example check of the autocorrelation data is to check whether a gradient of an autocorrelation curve associated with the autocorrelated data is greater than one; and if not then the system or method may indicate that it is not raining, park the wipers and/or not actuate wipers of the vehicle (see step S808). In this check, the gradient of the normalized autocorrelation of the disturbance is checked. The gradient of the normalized autocorrelation of a non-disturbed signal is close to 1. Measuring the gradient is beneficial because it is not affected by temperature change. Thus, the rain sensor may be substantially immune to false reads due to temperature changes in certain example embodiments of this invention. In certain example instances, gradients less than 1 (or some other predetermined value) may be considered no-rain events.

A third example check of the autocorrelation data is to determine whether there is a match or substantial match between an autocorrelation curve (e.g., signal footprint) associated with the autocorrelated data and one or more predetermined autocorrelation curve(s) (e.g., predetermined footprint) stored in a database and/or memory. When the shape of the autocorrelation curve associated with the autocorrelated data from the FIG. 4-5 circuit is different or substantially different from an autocorrelation curve relating to normalized non-disturbed autocorrelation data, this may be considered a no-rain event and it may be indicated that it is not raining, wipers may be parked, and/or wipers may be not actuated (see step S808). However, when there is a match or substantial match between the autocorrelation curve associated with the autocorrelated data from the FIG. 4-5 circuit and a predetermined autocorrelation curve associated with moisture such as rain, then it may be indicated that it is raining, wipers may be actuated, or kept moving.

In this regard, the shape of the autocorrelation curve may be used to reduce false wipes and/or false detections. In particular, the normalized autocorrelation of a non-disturbed signal is used as a reference. Then, the normalized autocorrelation of each signal captured from the FIG. 4-5 circuit is compared to the reference to identify the closest fingerprint in certain example instances. Generally, the more water present in the sensing area, the larger the difference between the reference signal and the observed signal. In this way, correlation snapshots can be compared to reference snapshots of well-known events such as the presence of rain, dirt, no-disturbance, ice, and so forth. In general, correlation snapshots may be normalized, though the invention is not so limited. Correlation snapshots preferably plot r-values versus quantums of time over a discrete time interval in certain example embodiments of this invention.

In certain example embodiments, when there is a match or substantial match between the autocorrelation curve associated with the autocorrelated data from the FIG. 4-5 circuit and a predetermined autocorrelation curve associated with a non-moisture substance such as dirt, then this may be considered a no-rain event and it may be indicated that it is not raining, wipers may parked and/or not actuated (see step S808).

Thus, it will be appreciated that the shape of the autocorrelation curve resulting from the data output from the FIG. 4-5 circuit (from the capacitors C1-C4, or via $C_{int}$) may be used to reduce false wipes as a third condition. For instance, a normalized autocorrelation curve of a non-disturbed signal may be used as a reference. Then, the normalized autocorrelation of each signal captured from the FIG. 4-5 circuit is compared to the reference to identify the closest fingerprint. Generally, the more water present in the sensing area, the larger the difference between the reference signal and the observed/detected signal. In this way, correlation snapshots can be compared to reference snapshots of well-known events. In general, correlation snapshots preferably are normalized, though the invention is not so limited. Correlation snapshots preferably plot r-values versus quantums of time over a discrete time interval.

A potential problem with capacitive rain sensors is that rapid temperature changes (e.g., due to the radiation absorbing black frit used to cosmetically hide the sensor pattern) change the dielectric "constant" (permittivity) of the glass. This is then registered as a capacitance change and may erroneously be interpreted as a rain signal. However, according to certain example embodiments of this invention, a normalized autocorrelation function is unchanged, or substantially unchanged, for different temperatures even though there may be differences for the non normalized autocorrelation functions for the different temperatures. Thus, in certain example embodiments of this invention, the sensing system is unaffected or substantially unaffected by temperature changes.

In addition, extremely slow accumulation of water like ultra-fine mist can slowly build up to a level that triggers sensors based on Nyquist rate converters. In the time of observation that concerns human vision (e.g., 30-60 Hz), the autocorrelation function in certain example embodiments of this invention is able to discriminate between the ultra-slow accumulation of dew or condensation and normal mist and rain.

Figure 11A:
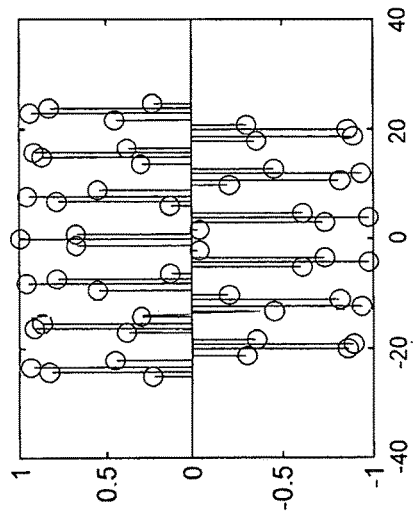
FIG. 11A is an example experimentally-obtained autocorrelation snapshot indicative of heavy rain.
Figure 11B:
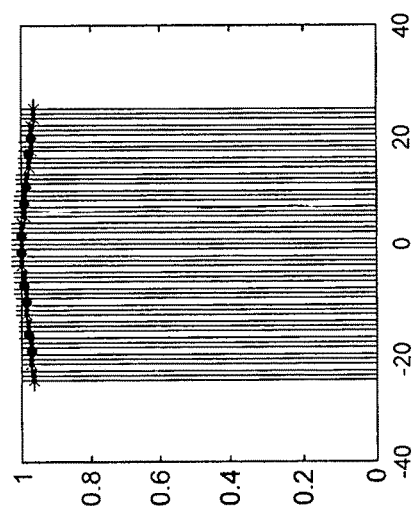
FIG. 11B is an example experimentally-obtained autocorrelation snapshot indicative of a light mist.
Figure 11C:
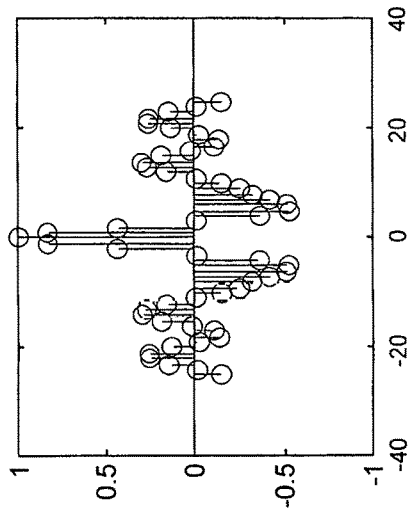
FIG. 11C is an example experimentally-obtained autocorrelation snapshot indicative of CB radio interference.
Figure 11D:
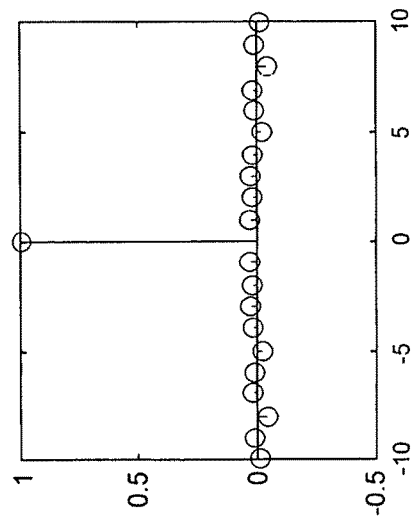
FIG. 11D is an example experimentally-obtained autocorrelation snapshot indicative of a grounded body with a voltage.

FIGS. 11A-11D provide sample experimentally-obtained correlation snapshots. These correlation snapshots, or fingerprints/footprints of an event, can be stored as reference footprints/fingerprints or correlation curves. Observed/detected correlation snapshots (e.g., autocorrelation curves) can be compared to these reference footprints or fingerprints to determine the type of event occurring. For instance, FIG. 11A is an experimentally-obtained autocorrelation snapshot indicative of heavy rain. FIG. 11B is an experimentally-obtained autocorrelation snapshot indicative of a light mist. FIG. 11C is an experimentally-obtained autocorrelation snapshot indicative of CB radio interference. FIG. 11D is an experimentally-obtained autocorrelation snapshot indicative of a grounded body with a voltage. The patterns or data of FIGS. 11A-11D may be called predetermined footprints or fingerprints in certain instances, and it will be appreciated that other types and shapes of predetermined footprints may also be used in different embodiments of this invention. It will be appreciated that these fingerprints/footprints are provided as non-limiting examples and reflect experimentally-obtained data. Actual events may differ in various characteristics. Thus, in certain example embodiments of this invention, when it is determined that there is a match or substantial match between the autocorrelation curve associated with the autocorrelated data from the FIG. 4-5 circuit and a predetermined non-moisture autocorrelation curve such as that of FIG. 11C or FIG. 11D, then this may be considered a no-rain event and it may be indicated that it is not raining, wipers may parked and/or not actuated (see step S808). However, in certain example embodiments of this invention, when it is determined that there is a match or substantial match between the autocorrelation curve associated with the autocorrelated data from the FIG. 4-5 circuit and a predetermined moisture-related autocorrelation curve such as that of FIG. 11A or FIG. 11B, then this may be considered a rain event and it may be indicated that it is raining, wipers may be actuated and/or kept moving. In addition to the predetermined autocorrelation curves of FIGS. 11A-11D, other reference fingerprints may be stored and/or compared with observed correlation snapshots in other example embodiments of this invention.

Turning back to FIG. 8, in step S806 it is determined whether each of the three conditions set forth in the bottom portion of the S804 box is met. In particular, it is determined in S806 whether each of the following is met: (a) the autocorrelated data has no negative values; (b) a gradient of an autocorrelation curve associated with said autocorrelated data is greater than a predetermined value such as one; and (c) the shape of the autocorrelation curve associated with the autocorrelated data from the FIG. 4-5 circuit is different than a predetermined autocorrelation curve associated with non-disturbed autocorrelation data. If they are not all met, this is an indication of a non-rain event and the process moves to step S808 where the vehicle wiper(s) are parked (if they were moving) or are kept off, and begins initialization S800 again. However, if all of these requirements are met in S806, then the process moves to S810 and the vehicle's wipers (e.g., windshield wipers) are activated at their lowest speed.

Figure 13:
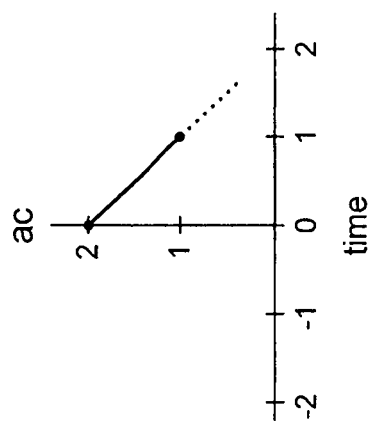
FIG. 13 is an example of autocorrelation according to an example embodiment of this invention.
Figure 15:
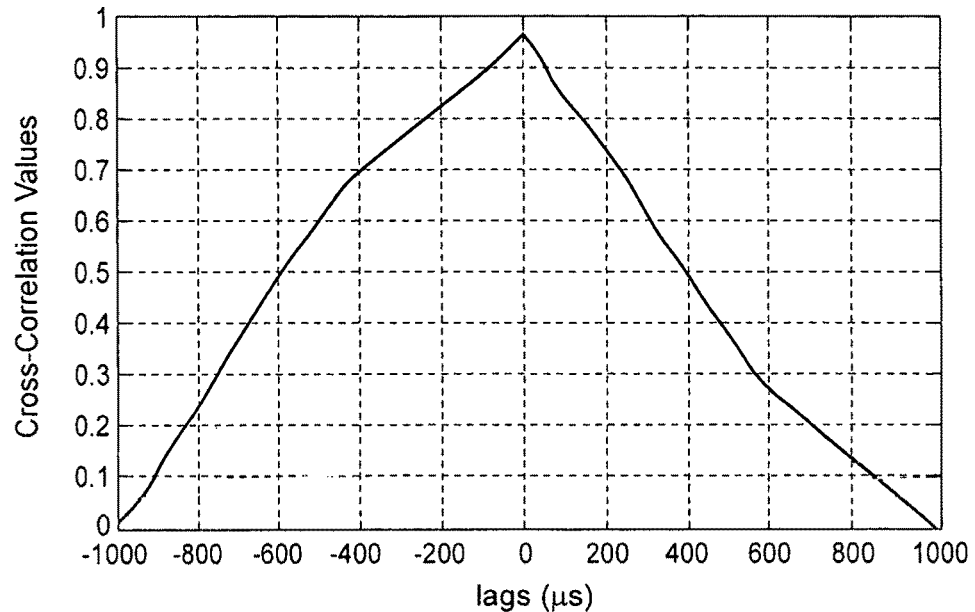
FIG. 15 is a crosscorrelation graph, plotting crosscorrelation values versus time lags (the time lags are in terms of microseconds in the time domain) according to an example of this invention, using certain signals from FIG. 14.
Figure 16:
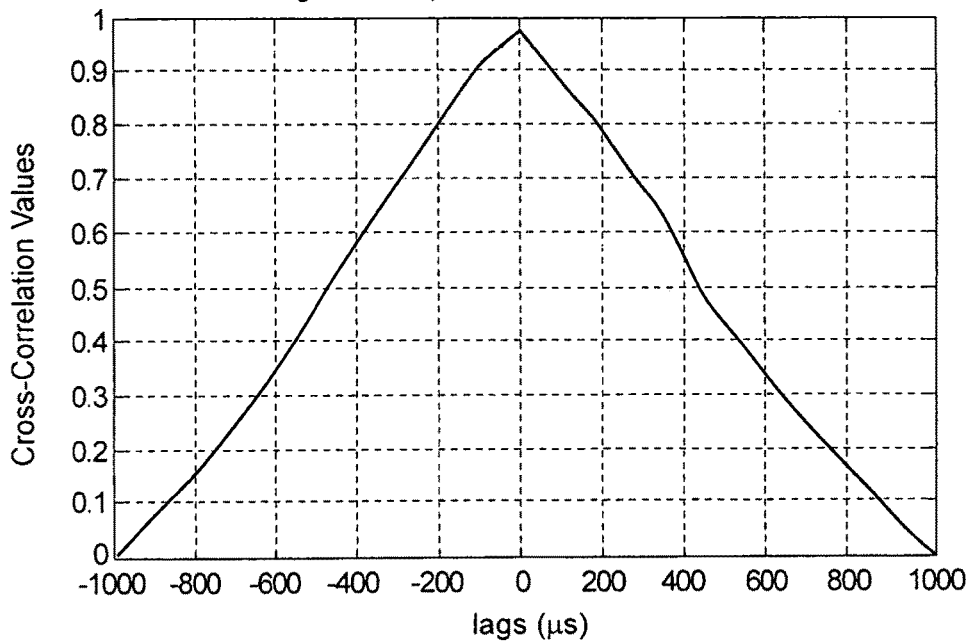
FIG. 16 is a crosscorrelation graph, plotting crosscorrelation values versus time lags (the time lags are in terms of microseconds in the time domain) according to an example of this invention, using certain signals from FIG. 14.
Figure 17:
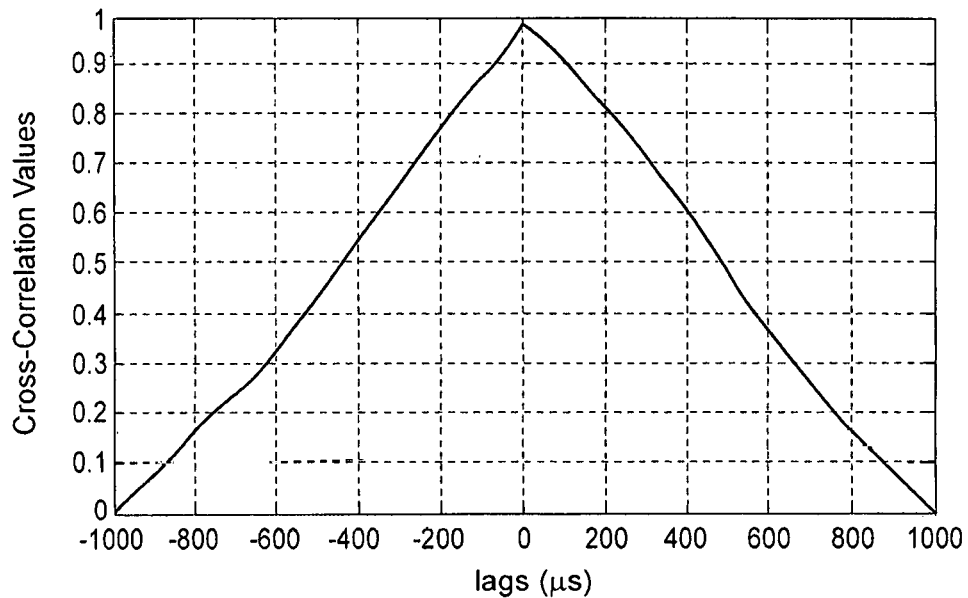
FIG. 17 is a crosscorrelation graph, plotting crosscorrelation values versus time lags (the time lags are in terms of microseconds in the time domain) according to an example of this invention, using certain signals from FIG. 14.
Figure 18:
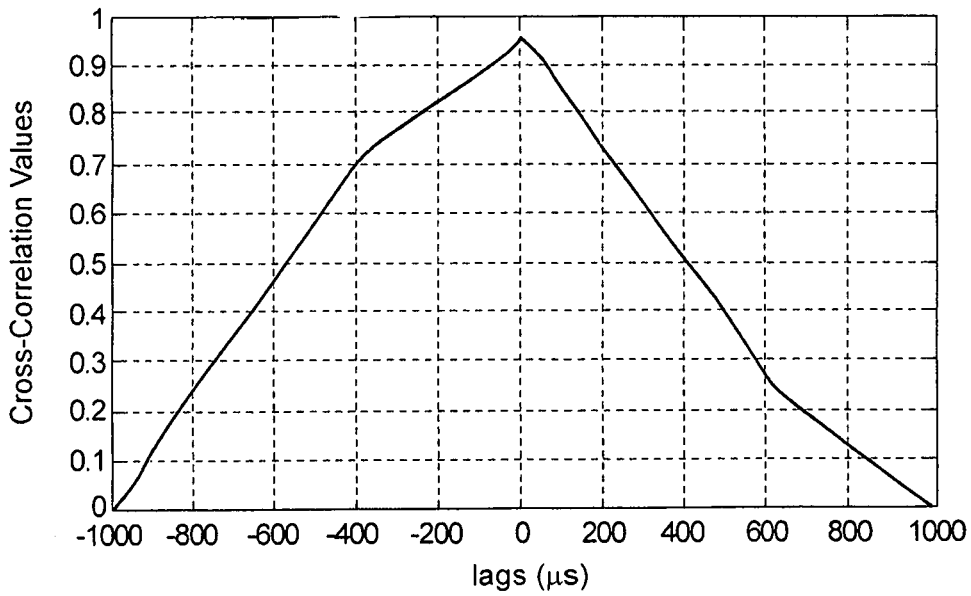
FIG. 18 is a crosscorrelation graph, plotting crosscorrelation values versus time lags (the time lags are in terms of microseconds in the time domain) according to an example of this invention, using certain signals from FIG. 14.
Figure 19:
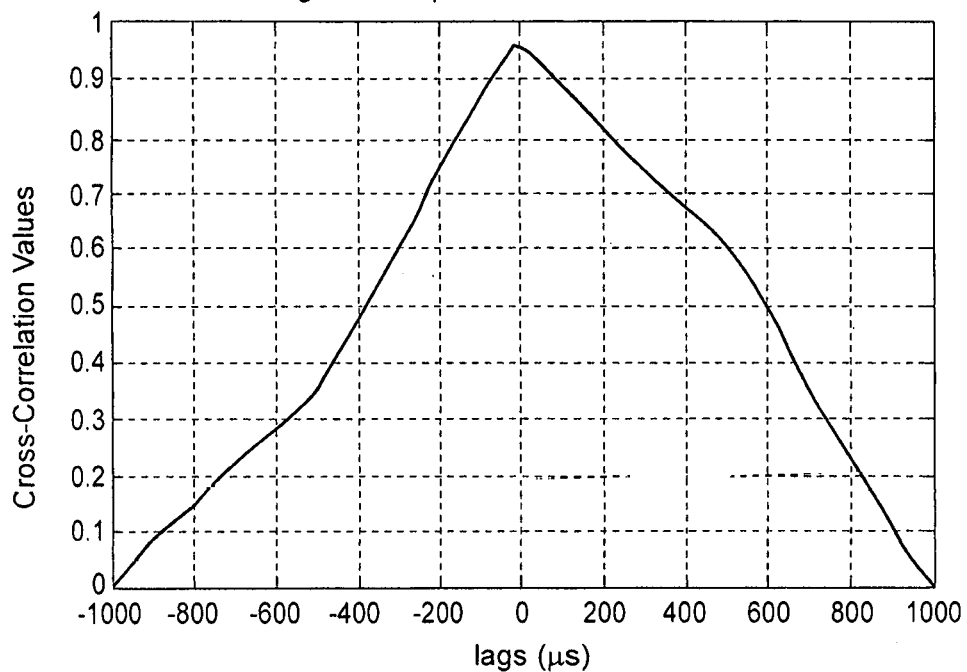
FIG. 19 is a crosscorrelation graph, plotting crosscorrelation values versus time lags (the time lags are in terms of microseconds in the time domain) according to an example of this invention, using certain signals from FIG. 14.
Figure 20:
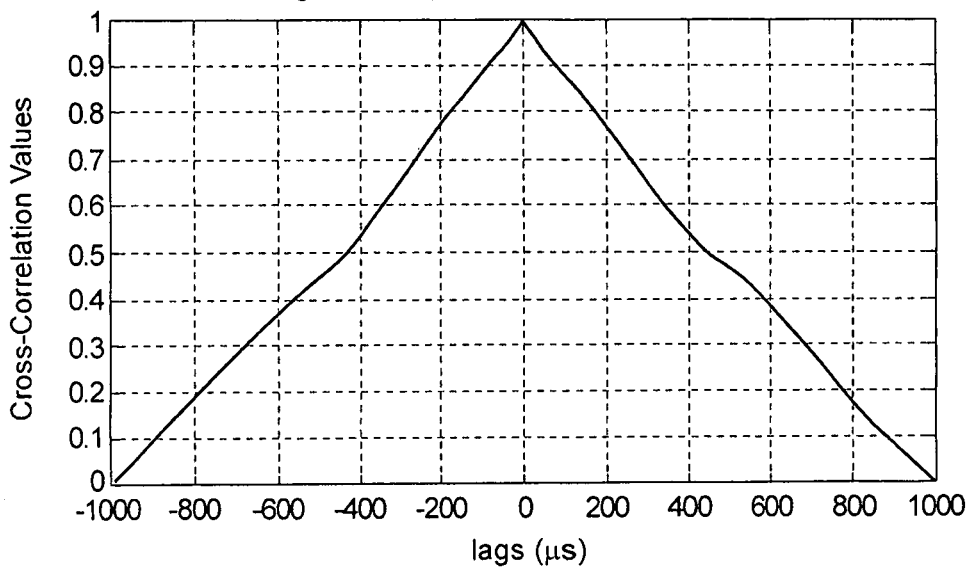
FIG. 20 is a crosscorrelation graph, plotting crosscorrelation values versus time lags (the time lags are in terms of microseconds in the time domain) according to an example of this invention, using certain signals from FIG. 14.
Figure 21:
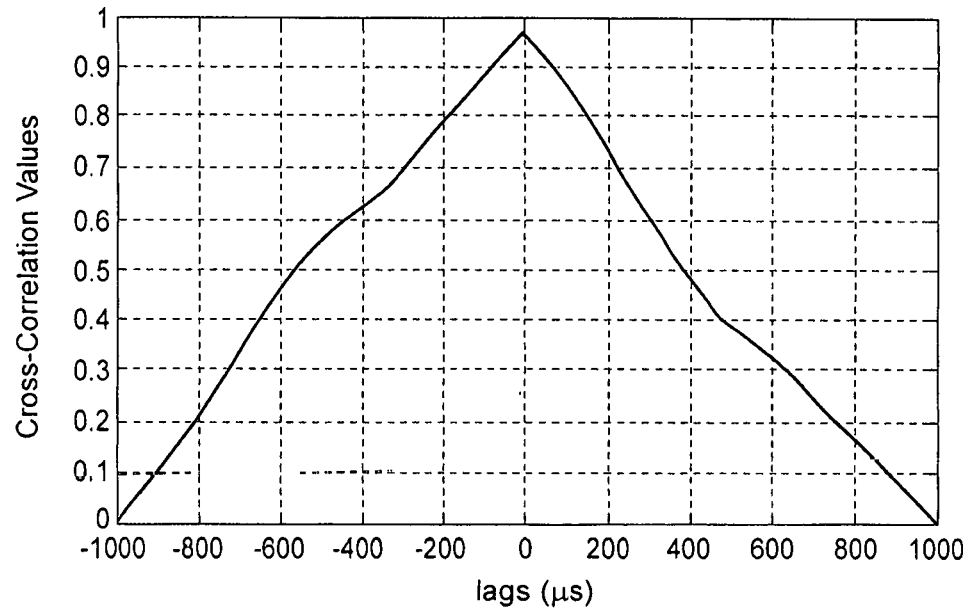
FIG. 21 is a crosscorrelation graph, plotting crosscorrelation values versus time lags (the time lags are in terms of microseconds in the time domain) according to an example of this invention, using certain signals from FIG. 14.
Figure 22:
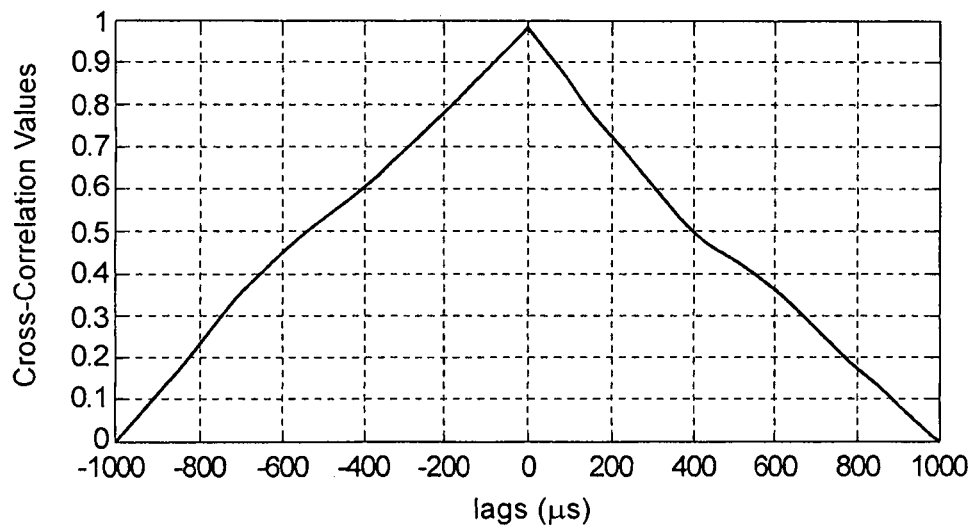
FIG. 22 is a crosscorrelation graph, plotting crosscorrelation values versus time lags (the time lags are in terms of microseconds in the time domain) according to an example of this invention, using certain signals from FIG. 14.
Figure 23:
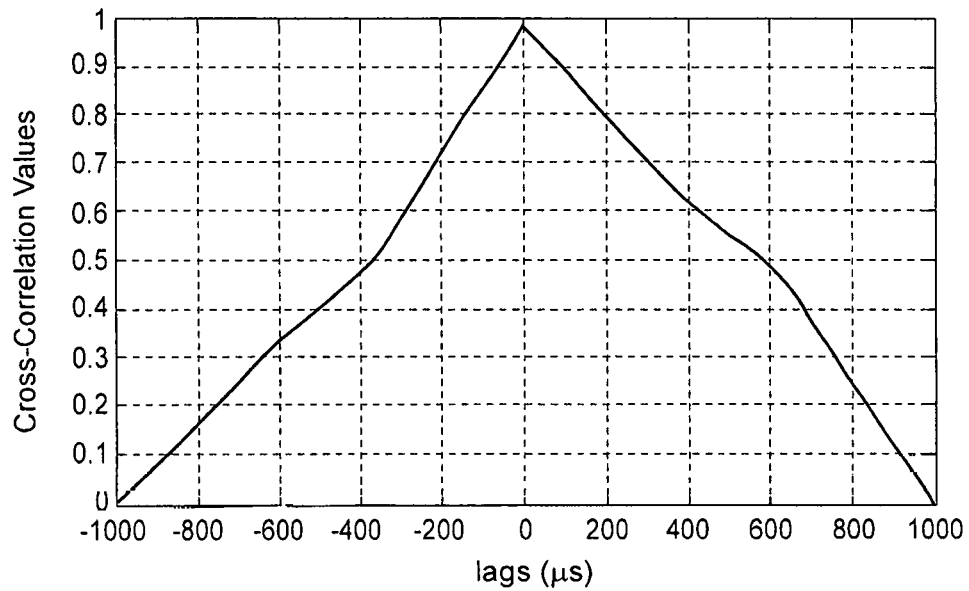
FIG. 23 is a crosscorrelation graph, plotting crosscorrelation values versus time lags (the time lags are in terms of microseconds in the time domain) according to an example of this invention, using certain signals from FIG. 14.
Figure 24:
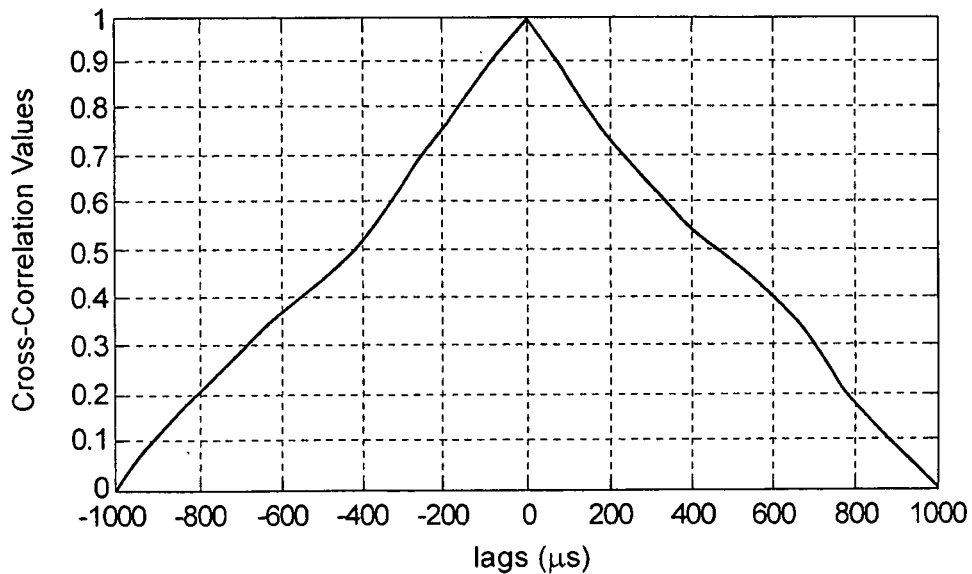
FIG. 24 is a crosscorrelation graph, plotting crosscorrelation values versus time lags (the time lags are in terms of microseconds in the time domain) according to an example of this invention, using certain signals from FIG. 14.

For purposes of example only, and understanding, FIG. 13 illustrates an example of autocorrelation. In FIG. 13, the values from (or relating to) sensing capacitor C1 are, at sequential times –t2, –t1, t0, t1, t2 and t3 are 0, 0, 1, 1, 0 and 0, respectively. Autocorrelation for time 0 (aco) is determined by multiplying the values relating to C1 in a non-offset manner, and then adding or summing the results. It can be seen in FIG. 13 that aco is equal to 2 in this instance. Thus, on the autocorrelation graph at the bottom of FIG. 13, an entry in the graph at time 0 is made for an autocorrelation value of 2. Note that the autocorrelation graph at the bottom of FIG. 13 is similar, but simpler, that the autocorrelation graph in FIG. 10 and the autocorrelation values may be obtained for FIG. 10 in a like manner. Next, still referring to FIG. 13, autocorrelation is performed using the capacitance values relating to C1 for the next point in time to obtain autocorrelation value ac1. This next autocorrelation value (ac1) is obtained by shifting the bottom row sequence of values for C1 relative to the top row as shown in FIG. 13, and then multiplying the values in the rows which line up with each other and summing the results. FIG. 13 illustrates that ac1 is equal to 1 for time 1. Thus, this autocorrelation value of 1 for time t1 may be entered in the graph at the bottom of FIG. 13 and a line is drawn between the two entered data points for purposes of example and understanding. The, for the next time value (or lag), the bottom row is again shifted another segment over relative to the top row and the process repeated, and so forth. It can be seen that the autocorrelation plots in FIG. 10 may be obtained in a similar manner. In FIG. 13, it will be appreciated that cross-correlation may be performed by replacing the C1-related values in the bottom row with values from or related to another capacitor such as C2 (or C3 or C4).

Examining autocorrelation and/or cross-correlation also can help distinguish between, for example, light rain and heavy rain. For example, if only the autocorrelation in time is high (and crosscorrelation is low), then there probably is only light rain. FIG. 12A is an exemplary correlation matrix showing light rain. Of note in FIG. 12A is that the correlations between C1 and C1, C2 and C2, C3 and C3, and C4 and C4 (these are autocorrelations) over a given time period are high, while the rest of the correlations (the cross-correlations) are low. By hypothesis and confirmed experimental data, a matrix of this sort would indicate a light rain.

On the other hand, if both autocorrelation and cross-correlation in time between capacitor signals are high, there is probably fast rain. FIG. 12B is an exemplary correlation matrix showing heavy rain. In FIG. 12B, not only are the autocorrelations of individual capacitors high (i.e., the auto-correlations are the correlations between C1 and C1, C2 and C2, C3 and C3, and C4 and C4), cross-correlations between different capacitors also are generally high (the correlations in FIG. 12B going diagonally from the upper-left to the bottom-right are the autocorrelations, and the rest are the cross-correlations). By hypothesis and confirmed experimental data, a matrix of this sort would indicate a fast rain. The degree of cross-correlation can be quantized to determine the relative speed of the rain. This data can, in turn, be used to trigger various wiper speeds, as appropriate for the speed of the rain. For instance, the more cross correlations that are high, the higher the wiper speed to be used.

More systematically, in step S812, cross-correlations are computed (correlations between data relating to different capacitors), and the two sides of the cross-correlation curve are used to determine a symmetry level L. If the symmetry level is lower than a predefined threshold $t_{min}$, step S814 directs the system to step S816 where wipers are activated at the lowest speed, and the system is returned to initialization step S800. If the symmetry level is greater than $t_{min}$ but less than an arbitrary value t, step S818 directs the system to step S820 where wipers are activated at a faster or medium speed, and the system is returned to initialization step S800. It will be appreciated that a plurality of arbitrary values $t_i$ may be specified, and a symmetry level falling between $t_i$ and $t_{i+1}$ will activate an appropriate corresponding wiper speed and then return the system to initialization step S800. Finally, in step S822, if the symmetry level is above a predefined level $t_{max}$, step S822 directs the system to step S824 where wipers are activated at the highest speed, and the system is returned to initialization step S800. Thus, correlations from the data output from the FIG. 4-5 circuit can be used to adjust wiper speed. In certain example embodiments, the more cross correlations that are high, the higher the wiper speed to be used due to the likelihood of heavier rain.

For purposes of example and understanding, FIGS. 14-24 illustrate examples of cross-correlation performed according to certain example embodiments of this invention. FIG. 14 sets forth cross-correlation data in certain example instances, whereas FIGS. 15-24 illustrate cross-correlation graphs of certain of the data from FIG. 14 where rain is detected. In FIGS. 15-24, each lag on the horizontal axis is one microsecond (1 µs) for purposes of example, and sampling was performed every one microsecond. As explained above with respect to FIG. 13, in FIGS. 15-24 at time=0 (lag 0), there is no shift in time of the values from the different capacitors being correlated. FIG. 14 illustrates that when rain was present (see signals S1-S5 and W1-W5), the delta signals relating to autocorrelation were high. FIGS. 15-24 are cross-correlation plots relating to these signals. It is helpful to look for symmetry between the plots on the left and right hand sides of each of FIGS. 15-24 (one side of zero is compared to the other side of zero). Generally speaking, if there is symmetry about the zero lag axis, there is not much cross-correlation which indicates that the detected rain is not very hard. However, if there is asymmetry about the zero lag axis, then this means more cross-correlation and indicates that the rain is hard or harder. For example, note the asymmetry in FIGS. 18, 19 and 23 about the zero lag axis due to the bumps or valleys on one or both sides. More cross-correlation indicates that the rain drops are moving from one capacitor's sensing area to another capacitor's sensing area. In this respect, each interaction of a rain drop and the surface of a windshield has its own correlation signature in the time domain. High cross-correlation indicates that the same drop is being detected at different capacitors, at different points in time (e.g., see FIG. 9 also). It is noted that the lower case "t" in FIG. 9 is the same as the lags axis in FIGS. 15-24.

Thus, it will be appreciated that certain example embodiments of this invention provide a moisture sensor (e.g., rain sensor) that can detect rain or other material on a vehicle window or other type of window or sheet/surface, without the need for a reference capacitor. Spatial temporal correlation may be used. All capacitors, or a plurality of capacitors, in the sensing array may be identical or substantially identical in shape in certain example embodiments. For purposes of example, at a given point in time (e.g., t1), the system may compare C1-relates values with C2 related values, and/or other capacitor related values. For this time t1, the system may also compare C1-related values with itself (autocorrelation), and may also compare autocorrelation for C1 with autocorrelation for C2 and/or other sensing capacitor(s).

FIGS. 4-5 illustrate switches for selectively coupling the various capacitors C1-C4 to the rest of the circuit, and FIG. 26 illustrates a multiplexer in this respect. The circuits shown in FIGS. 4-5 and/or 26 may read out signals from all of the capacitors C1-C4 simultaneously, or alternatively may only read out signals from one capacitor at a time selected from C1-C4, or as a further alternative may read out signals from a combination of some but not all of capacitors C1-C4 at a given point in time. An example non-limiting switching circuit for selective coupling the read-out electronics to one or more of capacitors C1-C4 as needed or as desired in discussed below in connection with FIG. 31. The FIG. 31 switching circuit, or the like, may or may not be used instead of the switches shown in FIGS. 4-5 and/or the multiplexer shown in FIG. 26.

Figure 31:
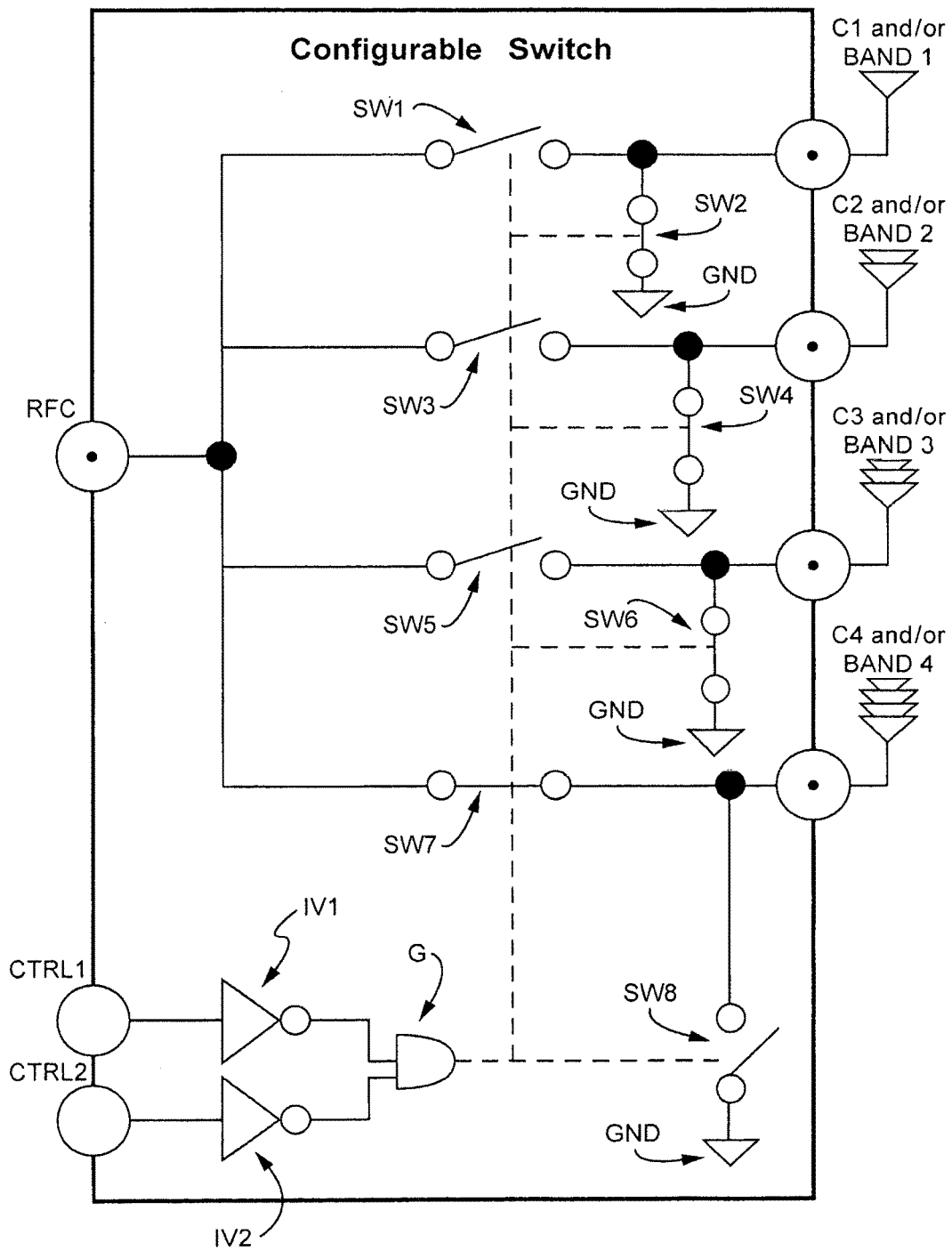

FIG. 31 illustrates an example switching circuit for selectively coupling or switching between different sensing capacitors C1-C4 or different combinations thereof, in order to change the sensing field being analyzed and/or change the feature being searched for. Thus, the FIG. 31 switching circuit allows the sensing field(s) and/or system to be selectively reconfigurable in certain example embodiments of this invention. For example, in certain example embodiments, the switching circuit may selectively switch between: (a) capacitor(s) (e.g., C1) for detecting rain on an exterior surface of the window, and (b) capacitor(s) (e.g., one or more of C2, C3 and/or C4) for detecting one or more of ice on an exterior surface of the window, mist on an exterior surface of the window, and/or moisture on an interior surface of the window. The read-out circuit(s) may read out signals from all of the capacitors C1-C4 simultaneously, or alternatively may only read out signals from one capacitor at a time selected from C1-C4, or as a further alternative may read out signals from a combination of some but not all of capacitors C1-C4 at a given point in time; the switching circuit of FIG. 31 permits each of these possibilities to be realized and selectively caused as desired. Thus, the switching circuit of FIG. 31 may be advantageous in that it may permit the system to be selectively adjusted, via the sensing field, in order to focus on different types of elements (e.g., rain, ice, mist, etc.) at different points in time. Capacitors C1-C4 may or may not have the same fractal pattern or geometry, and may or may not be of different shapes and/or sizes in different instances.

The switching circuit of FIG. 31 includes a power source connection at RFC, control connections at CTRL1 and CTRL2, inverters IV1 and IV2, AND gate G, and switches SW1, SW2, SW3, SW4, SW5, SW6, SW7 and SW8. The switches SW1-SW8 may be microelectromechanical (MEM) switches where application of voltage to the MEM causes the switch to be actuated, or any other sort of suitable switch in different instances. In this example embodiment, each capacitor has two switches associated therewith. For example, sensing capacitor C1 (and/or Band 1 if the sensing device is an antenna instead of a capacitor) has switches SW1 and SW2 associated therewith, sensing capacitor C2 (and/or Band 4 if the sensing device is an antenna instead of a capacitor) has switches SW3 and SW4 associated therewith, sensing capacitor C3 (and/or Band 4 if the sensing device is an antenna instead of a capacitor) has switches SW5 and SW6 associated therewith, and sensing capacitor C4 (and/or Band 4 if the sensing device is an antenna instead of a capacitor) has switches SW7 and SW8 associated therewith. In FIG. 31, for purposes of example, switches SW2, SW4, SW6 and SW7 are illustrated in the closed position, where switches SW1, SW3, SW5 and SW8 are illustrated in the open position.

Switches SW2, SW4, SW6 and SW8 are provided for selectively coupling the capacitors C1-C4 (and/or Bands 1-4) to ground GND. In certain example embodiments, when a given capacitor is coupled to the read-out circuitry (e.g., C4 is coupled to the read-out circuitry in FIG. 31 because switch SW7 is closed), that capacitor is decoupled from ground GND by opening its ground switch (e.g., ground switch SW8 is open in FIG. 31). However, when a given capacitor(s) is not coupled to read-out circuitry (e.g., capacitors C1, C2 and C3 are not coupled to read-out circuitry in FIG. 31 because read-out switches SW1, SW3 and SW5 associated therewith are open), that capacitor is grounded by closing its ground switch (e.g., ground switches SW2, SW4 and SW6 are closed in order to ground C1, C2 and C3, respectively, in FIG. 31). Grounding of capacitors not currently being read out is advantageous in that it permits noise and/or other problematic signals from interfering with the read-out circuitry or the overall switching circuit.

Still referring to FIG. 31, for purposes of example and without limitation, let us consider an example situation where capacitor C1 designed (e.g., shaped) and positioned for sensing rain on an exterior surface of the window (e.g., windshield), capacitor C2 is designed and positioned for sensing ice on an exterior surface of the window, capacitor C3 is designed and positioned for sensing mist or fog on an exterior surface of the window, and capacitor C4 is designed and positioned for sensing condensation/moisture on an interior surface of the window (e.g., if C4 detects such condensation and/or moisture on the interior surface, then a defroster may be turned on automatically or otherwise in order to remedy the same). In certain example such instances, each of the fractal capacitive sensors C1-C4 may have a different fractal pattern and/or shape, and/or a different orientation/direction. The switching circuit, in order to focus the read-out circuitry on detecting rain on an exterior surface of the window, can couple capacitor C1 to the read-out circuitry and isolate capacitors C2-C4 from the read-out circuitry; this can be done by sending control signals CTRL1 and CTRL2 which cause switches SW1, SW4, SW6 and SW8 to close and switches SW2, SW3, SW5 and SW7 to open. As another example, the switching circuit, in order to focus the read-out circuitry on detecting condensation and/or moisture on an interior surface of the window, can couple capacitor C4 to the read-out circuitry and isolate capacitors C1-C3 from the read-out circuitry; this can be done by sending control signals CTRL1 and CTRL2 which cause switches SW2, SW4, SW6 and SW7 to close and switches SW1, SW3, SW5 and SW8 to open as shown in FIG. 31. As another example, the switching circuit, in order to focus the read-out circuitry on detecting mist and/or fog on an exterior surface of the window, can couple capacitor C3 to the read-out circuitry and isolate capacitors C1-C2 and C4 from the read-out circuitry; this can be done by sending control signals CTRL1 and CTRL2 which cause switches SW2, SW4, SW5 and SW8 to close and switches SW1, SW3, SW6 and SW7 to open. As yet another example, the switching circuit of FIG. 31, in order to focus the read-out circuitry on both detecting ice and rain on an exterior surface of the window, can couple capacitors C1-C2 to the read-out circuitry and isolate capacitors C3-C4 from the read-out circuitry; this can be done by sending control signals CTRL1 and CTRL2 which cause switches SW1, SW3, SW6 and SW8 to close and switches SW2, SW4, SW5 and SW7 to open. It is also possible in certain example instances to couple all capacitors C1-C4 to the read-out circuitry, in which case switches SW1, SW3, SW5 and SW7 would be closed and switches SW2, SW4, SW6 and SW8 would be opened.

It will be appreciated that the switching circuit of FIG. 31 may or may not be used in combination with any other example embodiment discussed herein.

Moreover, it is possible that capacitors C1-C4 in connection with the FIG. 31 embodiment may be replaced with antennas such as fractal based antennas having respective Bands (see Bands 1-4 in FIG. 31). Thus, in this situation, the circuit of FIG. 31 would be able to selectively reconfigure fractal-based antennas of different bands in order to selectively change the band(s) being read out by the read-out circuitry. In such example instances, the read-out circuitry may be used to detect and/or process incoming waves such as AM, FM, Bluetooth, GPS, VHF, and/or UHF signals.

As is clear from the description provided above, certain example embodiments disclosed above relate to a fractal capacitor based rain sensor. Such capacitors allow for higher capacitance per unit area by using lateral fringing fields. As described in detail above, the fringing fields emanating at the surface of the glass may be used to detect moisture, debris, and/or the like. The amount of lateral fringing is proportional to the periphery, and thus the perimeter, of the structure. As noted above, such a fractal capacitor based rain sensor may be printed on glass using, for example, silver frit, which may be located on any one of surfaces 2, 3, and 4 of the windshield. Such arrangements are shown in, and described in connection with, FIGS. 1(b)-1(f).

Placing the pattern on surface 4 is practical and fairly easy to implement using conventional windshield manufacturing techniques. However, in practice, positioning the pattern here typically requires that springy contacts be used to connect the capacitors to the read-out electronics and computing circuitry. This design approach has proven to be effective despite several challenges. For example, first, a hermetic seal sometimes is required to decouple the condensation effects on surface 4 inside the vehicle. Second, there often may be inherent mechanical vibrations at the contact pads. Third, the contacts may be subject to corrosion.

The autocorrelation techniques described above help to overcome the first challenge, e.g., without the use of a hermetic seal. The second and third challenges may be overcome by using gold-coated spring loaded pins. However, this solution implies that such systems, if not properly mechanically designed, could be affected by vibrations at the contacts, e.g., creating minute changes in capacitance values while the vehicle is moving, for example. More generally, though, mechanically induced vibrations may, in turn, translate into capacitive noise that can affect the ultimate sensitivity of the rain sensor.

As such, although the example arrangements and design approaches described above have been successful, further improvements are still possible. For example, the above-noted potential challenges may be addressed in certain example embodiments by providing an integrated capacitive-based moisture and/or debris sensor having embedded electronics located on a flexible printed circuit board (PCB). In brief, the sensor may comprise an array of fringe effect capacitors, which may be, screen printed, etched directly, or otherwise located, on a flexible PCB in accordance with certain example embodiments. The flexible PCB, in turn, may include the read electronics components. Once the sensor array is formed on the flexible PCB, the assembly may be glued, laminated directly, or otherwise located onto the windshield. In certain example embodiments, the flexible PCB and sensor array assembly may be located on surface 4, whereas in certain example embodiments, the flexible PCB and sensor array assembly may be located between surfaces 2 and 3.

In certain example embodiments, the flexible PCB and sensor array assembly may comprise a multi-layer, distributed array of capacitors, stacked on top of each other, and electrically isolated and shielded from each other. In certain example embodiments, such an arrangement advantageously may be made compactly, as the length of the excitation and return lines to the capacitors may be reduced while all electronics required, in turn, may be embedded on the sensor.

As alluded to above, in certain example embodiments, the flexible PCB may be used to mechanically support and/or electronically connect electronic components using conductive pathways and/or traces, which may be etched from copper sheets laminated onto a non-conductive substrate. A flexible PCB generally comprises a flexible polymer film laminated to a thin sheet of copper that is etched to produce a circuit pattern. Patterns may be created on one or both sides of the film, and interconnections may be achieved, e.g., via plated through-holes, providing enhanced adaptability between component parts. A polymer overcoat may be added to insulate and/or environmentally seal the circuit.

One example of a flexible polymer film that may be used in connection with the flexible PCBs of certain example embodiments is Kapton®. Kapton® has a high heat resistance, is dimensionally stable, and has good dielectric strength and flexural capabilities. In general, these characteristics of the raw material help the flexible circuit maintain a high degree of durability and also help it to survive hostile environments. Of course, the flexible PCBs of certain example embodiments may include any suitable polymer film.

The flexible PCBs of certain example embodiments also may combine several single and/or double-sided circuits with complex interconnections, shielding surface mounted devices in a multi-layer design. Such multi-layer designs optionally may be combined with rigid circuit boards in certain example embodiments, e.g., to create a rigid/flexible circuit capable of supporting devices as, and when, needed.

Certain example embodiments may lead to one or more of the following and/or other advantages. First, it may be possible to more precisely place the complete sensor assembly on the windshield. That is, the flexural capacity of the polymer may allow the sensor pattern to conform to curvatures of the windshield, with reduced (e.g., free from) moving parts. Second, laminating, gluing, or otherwise connecting the flexible PCB to the windshield may reduce the influence of interior water condensation (and/or other moisture or debris) on the "wet" capacitors.

Third, placing the "wet" and "dry" capacitors on separate layers and each facing away from each other allows the sensor to discriminate between outside and inside conditions. This may be used to take more appropriate actions, e.g., to cause wipes when water is detected on the exterior windshield by the "wet" capacitors whereas defogging may be caused when the "dry" capacitors read a threshold value.

Fourth, having both sets of capacitors next to each other may allow for the effects of rapid temperature changes or exposure to EMI to be identified. Random EMI, for example, will simultaneously have very similar signatures on both the "dry" and "wet" capacitors. Such signatures may be differentiated with either external rain events or interior fogging, for example, Fifth, and as above, the sensor may comprise a plurality of modules, including a sigma-delta analog-to-digital channel converter, a microprocessor unit with a memory (e.g., SRAM and/or Flash), and a LIN transceiver. Such components may function using a lower power and may be fitted with an independent battery and/or wireless transceiver. In such cases, the system may include a cradle or other suitable recharging means to allow recharging, e.g., from the car battery or other source.

Figure 32:
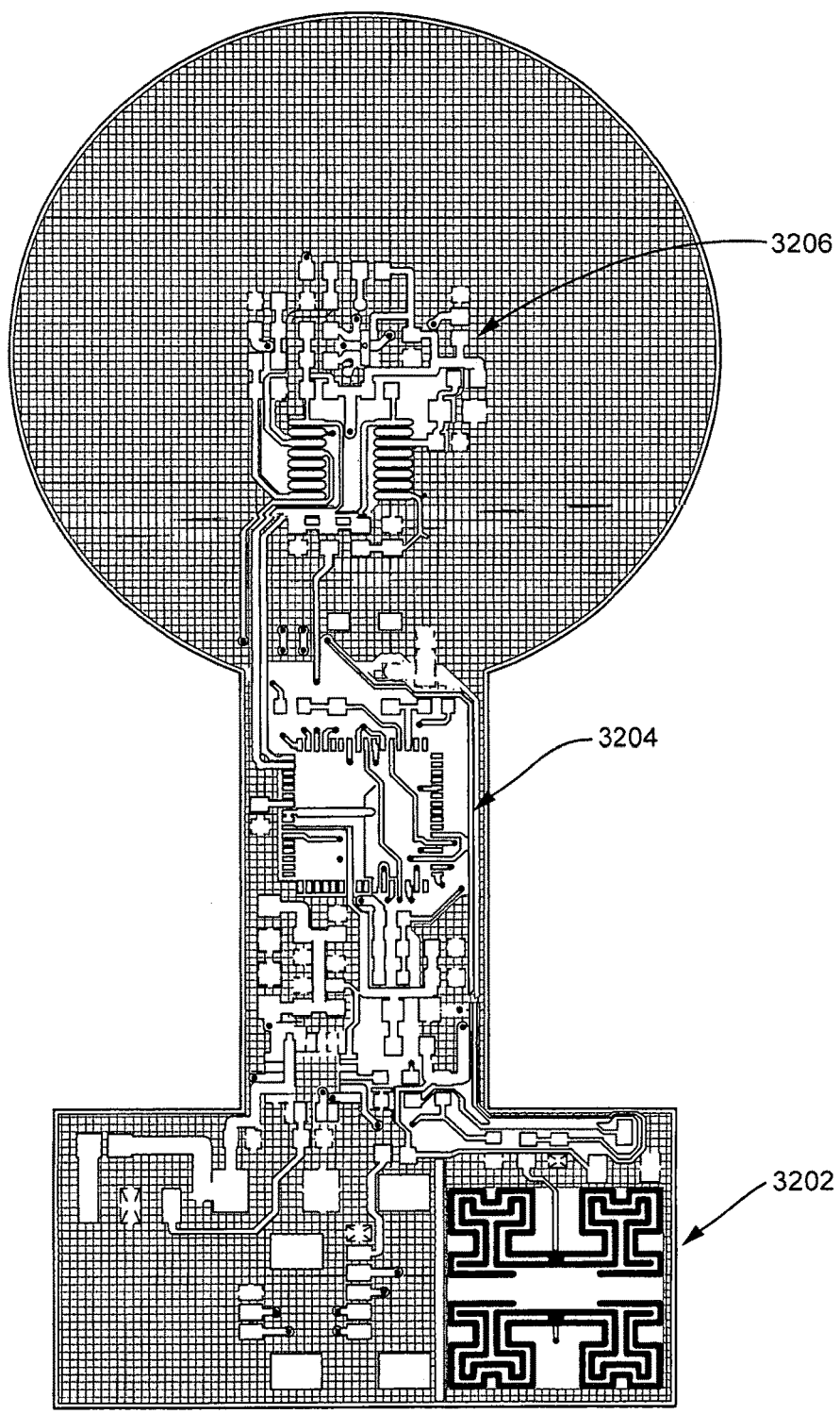
FIG. 32 shows an example first outer layer of a sensor according to an example embodiment.

FIGS. 32-35 show example layers comprising a PCB in accordance with an example embodiment. The PCB, as a whole, may be constructed from flex FR-4 or any suitable plastic, polyimide, polymer, etc., in certain non-limiting implementations. FIG. 32 shows an example first outer layer of a sensor according to an example embodiment. The first outer layer of FIG. 32 is designed to be located inside the car, on the side of the PCB closest to the driver. Thus, FIG. 32 includes an inside or "dry" capacitor array 3202, which may be formed in accordance with a fractal pattern in certain example embodiments. In certain example embodiments, multiple dry capacitor arrays 3202 may be formed on the first outer layer of FIG. 32, and/or the PCB of FIG. 32 may be connected to one or more "slave" PCBs in certain example embodiments. In the latter case, the slave boards may be tethered or wirelessly connected to the mater board. When slave boards are used, they may be attached to surface 4 of the glass directly or indirectly, e.g., to measure the humidity within the vehicle's cabin and/or moisture on the glass.

In either arrangement, the dry capacitor array(s) 3202 may be used to determine the presence of EMI and/or humidity (e.g., within the unit and/or car). EMI may be detected, for example, when the same or similar patterns are detected by both the wet and dry capacitor arrays at the same time or within a short predetermined time interval (e.g., within a few milliseconds or seconds or, more particularly, within about 20-40 ms), the wet and dry capacitor arrays being located on differing layers, and opposing sides, of the PCB. Connections 3204 are provided for a microprocessor (described in greater detail below). Connections 3206 also are provided for a sigma-delta converter/filter as described above.

One or more inner layers may be provided in certain example embodiments so as to provide shielding between the wet and dry capacitor arrays. This arrangement advantageously reduces the problems associated with some fields emanating outwardly and some fields emanating inwardly, which might cause spurious detections, measure the humidity within the vehicle when attempting to detect moisture outside the vehicle, etc. Thus, the one or more inner layers of certain example embodiments may help decouple the wet and dry capacitor arrays.

Figure 33:
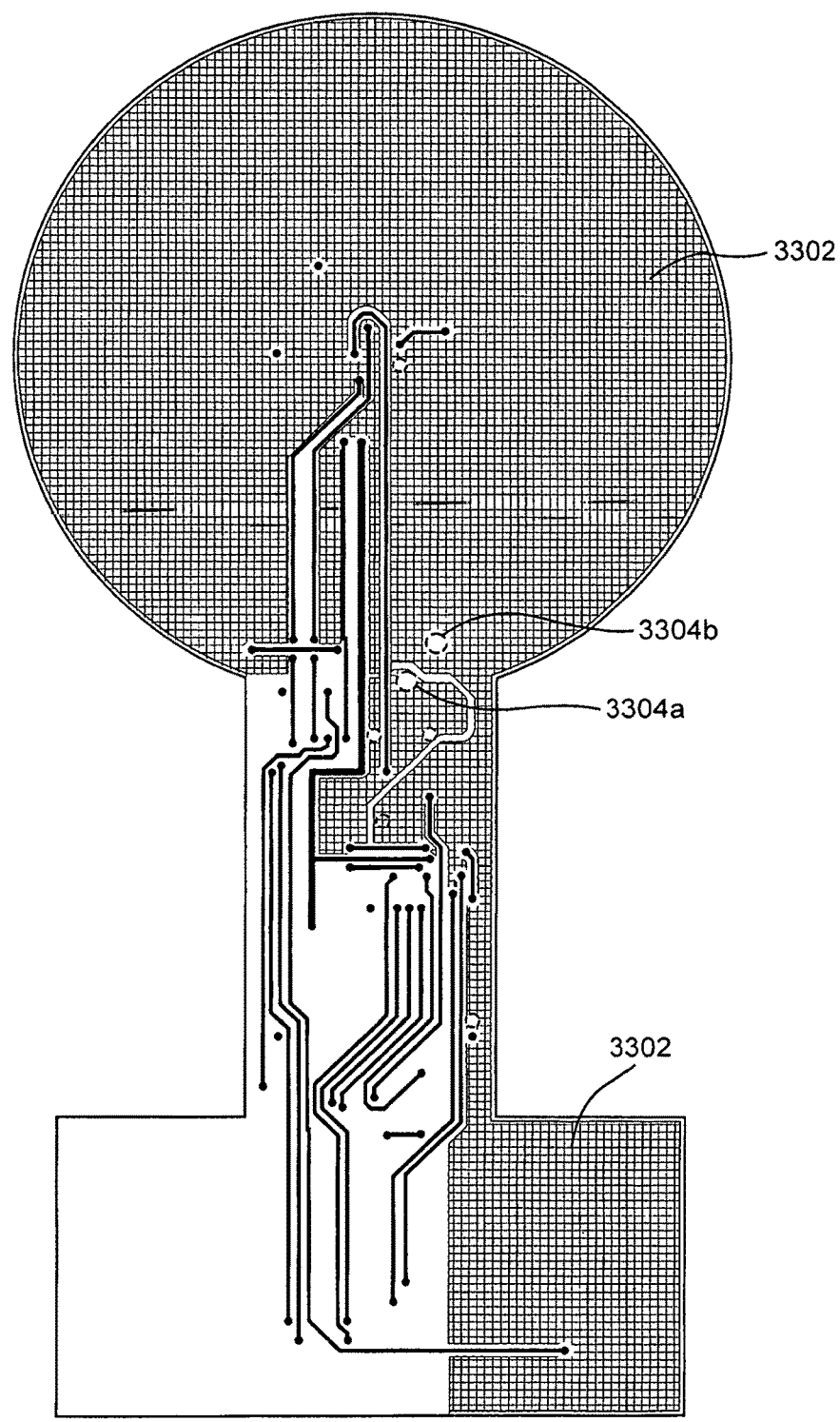
FIG. 33 shows an example first inner layer of a sensor according to an example embodiment.
Figure 34:
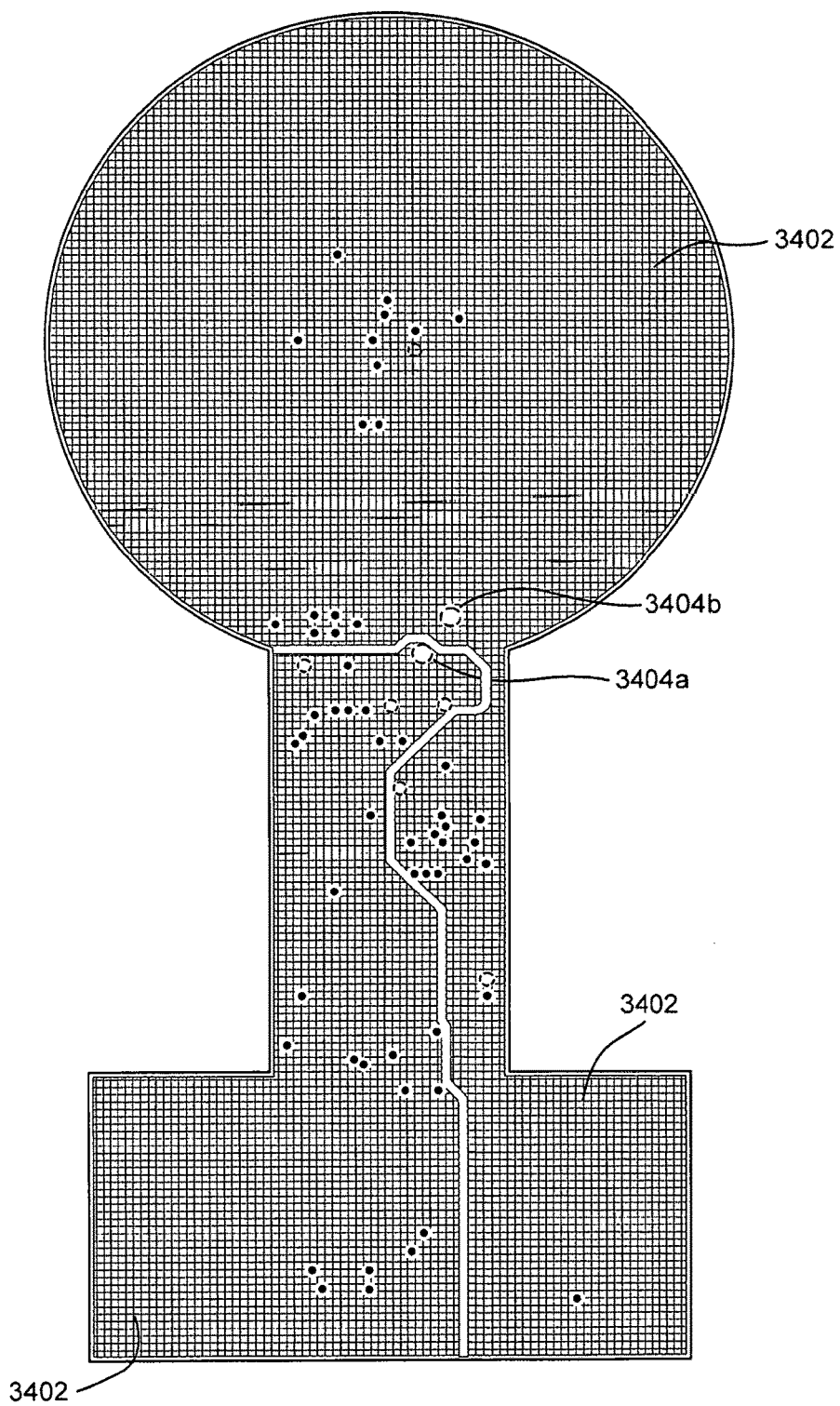
FIG. 34 shows an example second inner layer of a sensor according to an example embodiment.

As examples of the inner layers, FIG. 33 shows an example first inner layer of a sensor according to an example embodiment, and FIG. 34 shows an example second inner layer of a sensor according to an example embodiment. In FIG. 33, the majority of the layer is metallic 3302 (e.g., copper) and is at voltage potential. In addition to providing shielding, the metallic layer 3302 also makes it difficult for fields of the wet capacitor array to be coupled to the fields of the dry capacitor array, and vice versa. A number of conduits or lines connect between layers and also provide power to the chips. Digital and analog grounds 3304a, 3304b also are provided.

Figure 35:
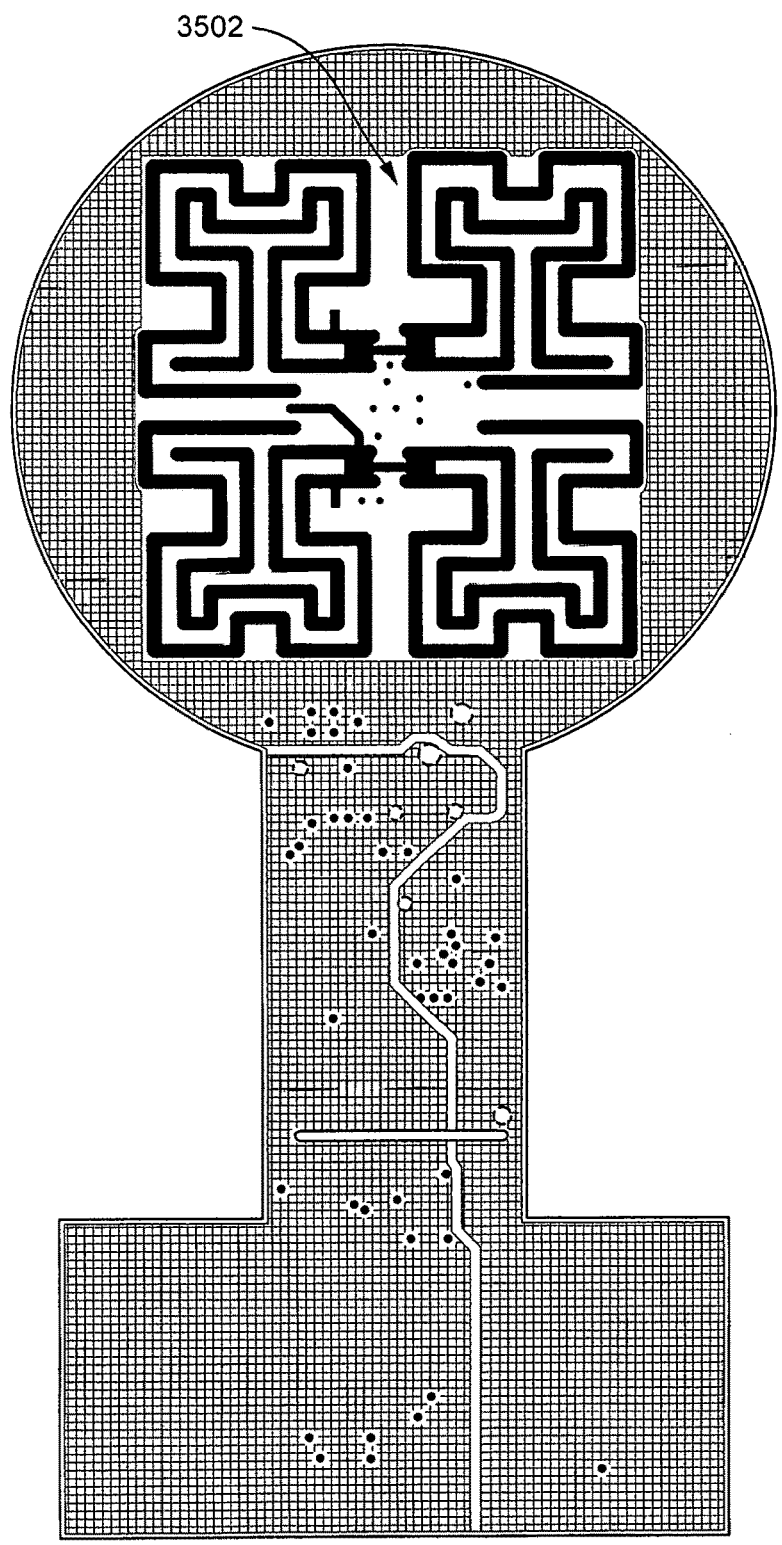
FIG. 35 shows an example second outer layer of a sensor according to an example embodiment.

The first inner layer shown in FIG. 33 is closer to the first outer layer shown in FIG. 32, whereas the second inner layer shown in FIG. 34 is closer to the second outer layer shown in FIG. 35. As above, the majority of the layer is metallic 3402 (e.g., copper), and digital and analog grounds 3404a, 3404b also are provided. As can be seen from FIGS. 33 and 34, the metallic, shielding portions are positioned on their respective layers so as to be at least adjacent to the wet and dry capacitor arrays, where the fields likely will be strongest.

FIG. 35 shows an example second outer layer of a sensor according to an example embodiment. The second outer layer of FIG. 35 is designed to be located inside the car, on the side of the PCB furthest from the driver and closest to the glass. Thus, FIG. 35 includes an outside or "wet" capacitor array 3502, which may be formed in accordance with a fractal pattern in certain example embodiments. The outside capacitance can be measured in a differential mode using Cin+ and Cin−, as well as in a single-ended mode in certain example embodiments. This may help reduce the signal to noise ratio considerably. Also, an RMS resolution of the system is above 16 bits in certain example implementations.

Figure 37A:
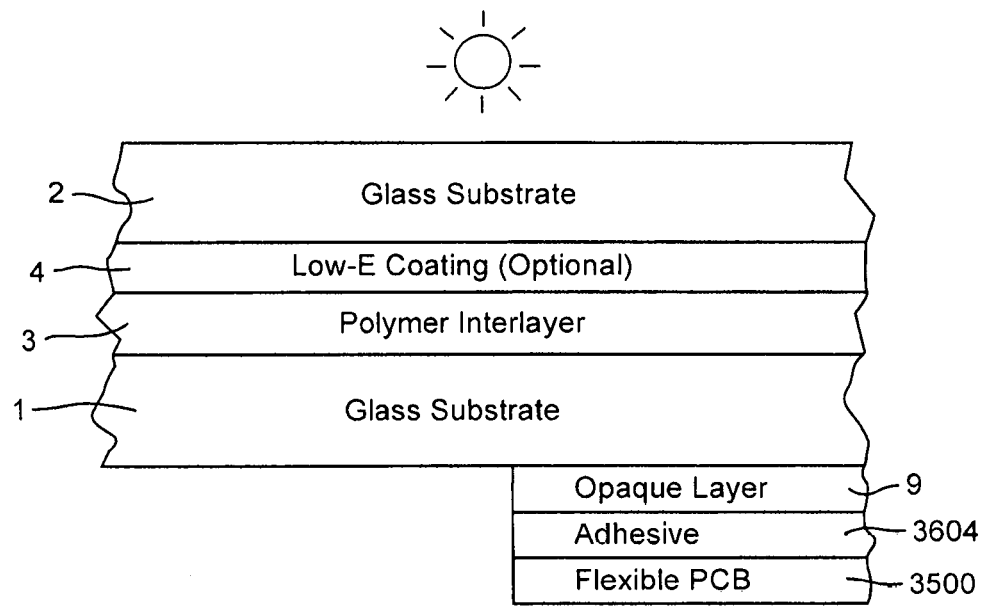
FIG. 37(a) is a cross-sectional view of a rain sensor supported by an interior surface of an inner glass substrate according to an example embodiment of this invention.

As noted above, one problem associated with current sensor technologies is a slight delamination or stress, or even improper installation, between the glass and sensor puts the optical system out of alignment. The bonding of certain example embodiments, however, helps reduce these and/or other precision alignment issues. In certain example embodiments, the PCB is attached to surface 4 of the windshield using an adhesive. For example, a double-sided adhesive tape may be used to secure the second outer layer to surface 4 of the windshield. In certain example embodiments, the PCB may be located behind the black frit printed on the glass. A double-sided adhesive tape advantageously may provide increased stability for the sensor (especially as compared to the pin design, which may allow for movement of the sensor and/or the individual pins directly and/or corrosion) while also substantially sealing it, reducing the chances of debris, moisture, and/or the like from coming into direct contact with the sensor and/or components thereof. In certain example embodiments, the glass and/or glass frit may be treated proximate to where the sensor is to be adhered, e.g., to facilitate the bonding process. For example, a silane-based precursor may be used to prepare the surface for adhesion. In certain example implementations, an adhesive tape commercially available from 3M such as VHB™ Adhesive Transfer Tapes with Adhesive 100MP (including F9460PC, F9469PC, and F9473PC) may be used to secure the PCB to the windshield. Of course, any suitable adhesive tape may be used in connection with certain example embodiments. An example of this arrangement is shown in FIG. 37(a).

In view of the above, it will be appreciated that the EM field lines for the outside capacitors in certain example embodiments probe only the outside of the car on the windshield surface and, on the inside, the outside capacitors' field lines are shunted via a "buried ground plane." Accordingly, its field lines do not probe inside the car or measure humidity from inside. The same rationale applies to the inside facing capacitors, as its field lines "see" the inside of the car. Free propagating EM waves (like EMI) can affect both sets of capacitors, and the occurrence of this event is indicative of an EMI event like a lightning strike. The inside array of capacitors also is able to pick up subtle changes in capacitance that relate to humidity level. It will be appreciated that the inclusion of a temperature sensor on the PCB set next to the inside capacitors enables the dew point to be accurately deduced.

Figure 36:
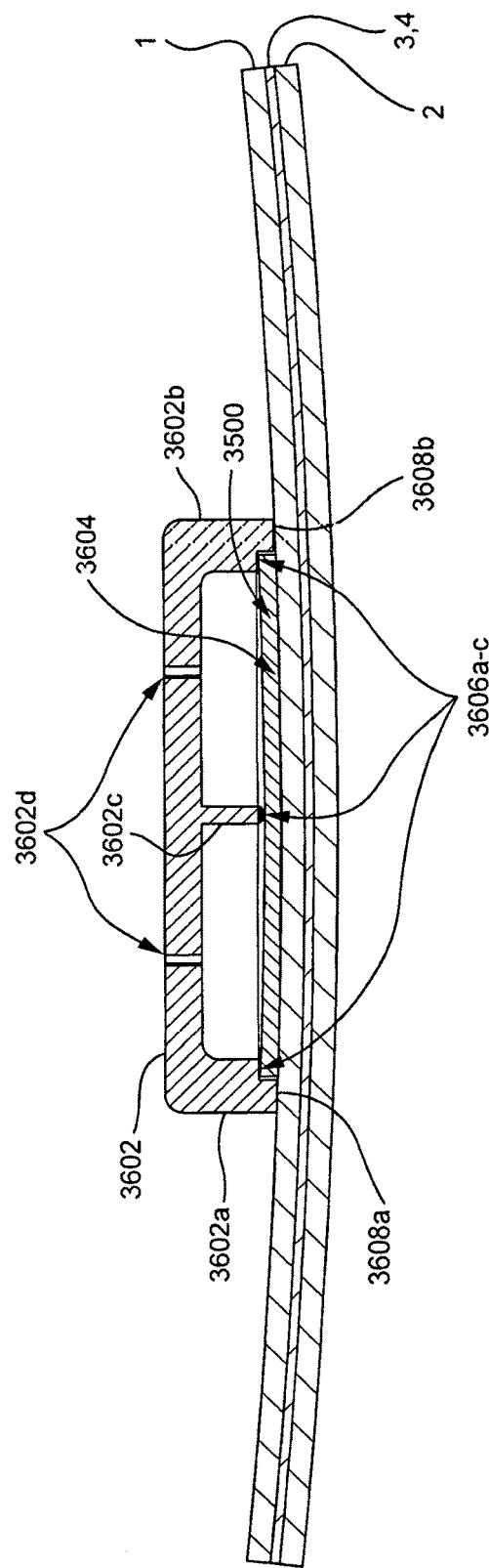
FIG. 36 is a cross-sectional view of an example PCB cover according to an example embodiment.

FIG. 36 is a cross-sectional view of an example PCB cover 3602 according to an example embodiment. The cover 3602 protects the PCB 3500, which is adhered to surface 4 of the inner glass substrate 1 of the windshield. The cover 3602 is substantially M-shaped when viewed in cross-section. As such, the cover 3602 includes a plurality of legs. In the example shown in FIG. 36, three such legs 3602a-c are shown, with left and right legs 3602a, 3602b, and a center leg 3602c. The left and right legs 3602a, 3602b are notched out so as to contact both surface 4 of the windshield and the PCB 1500. Soft plastic pieces 3606a-c may be added to the cover 3602 at the notched out portions of the left and right legs 3602a, 3602b, as well as at surface of the center leg 3602c that comes into contact with the PCB 1500, so as to hold the PCB in place while reducing the chances of damaging it. The portions of the left and right legs 3602a, 3602b that are not notched out may be adhered to surface 4 of the windshield using the adhesive tape 3604 that also serves to bond the PCB 1500 to surface 4 of the windshield. Alternatively or in addition, beads 3608a-b or other suitable fastening mechanisms may be used to bond the portions of the left and right legs 3602a, 3602b that are not notched out to surface 4 of the windshield. Because the PCB 1500 and/or components thereon may produce heat, one or more ventilation slots 3602d or through-holes may be provided to the cover 3602 so as to allow the heat to dissipate. Although not shown in FIG. 36, the cover 3602 may substantially fully enclose the PCB 1500.

Figure 37B:
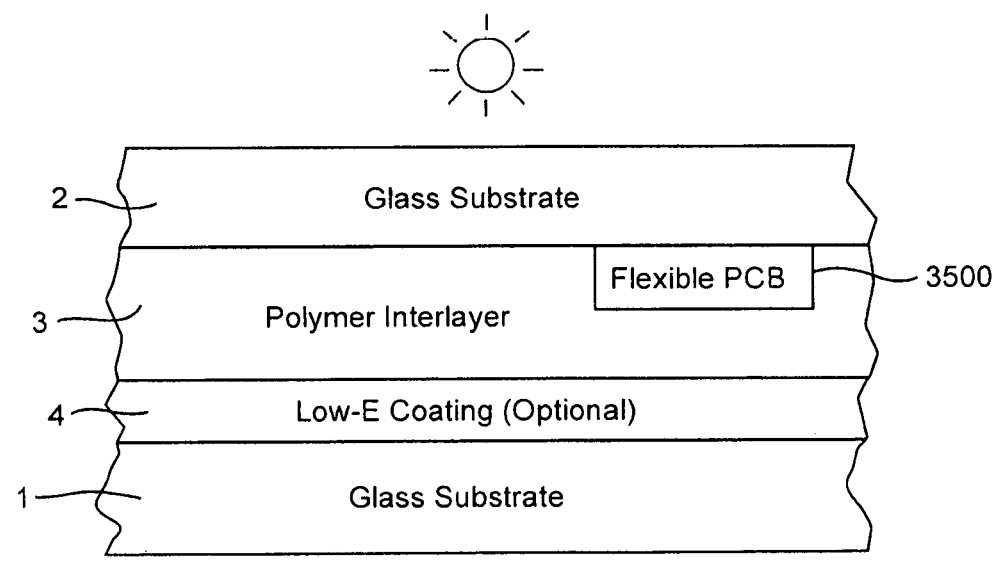
FIG. 37(b) is a cross-sectional view of a rain sensor supported by an interior surface of an outer glass substrate according to an example embodiment of this invention.
Figure 37C:
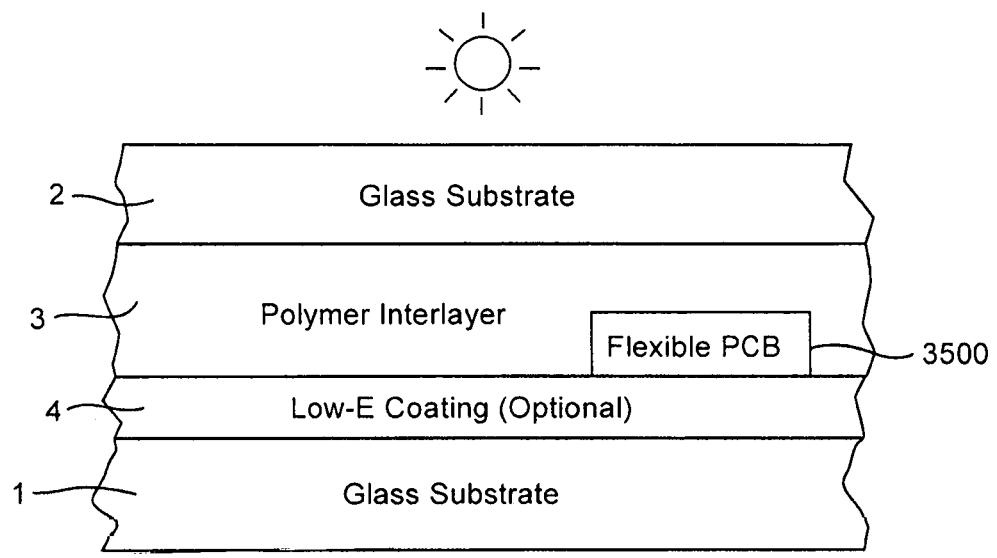
FIG. 37(c) is a cross-sectional view of a rain sensor supported by an outer surface of an inner glass substrate according to an example embodiment of this invention.
Figure 37D:
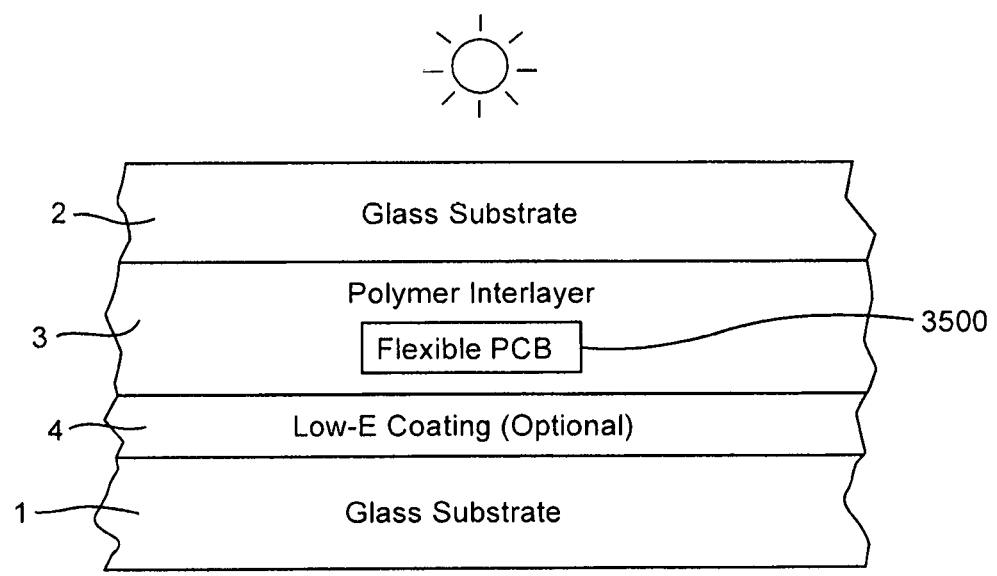
FIG. 37(d) is a cross-sectional view of a rain sensor embedded in a polymer interlayer according to an example embodiment of this invention.

In certain example embodiments, the rain sensor also may be supported by surface 2 as the example in FIG. 37(b) shows, surface 3 as the example in FIG. 37(c) shows, or in the polymer-inclusive layer between surfaces 2 and 3 as the example in FIG. 37(d) shows. In such example implementations, a flexible PCB may be assembled in accordance with the above-described techniques. The flexible PCB or layers of the flexible PCB may be embedded in or formed from a polymer or acrylic (including, for example, PET). In certain example embodiments, connecting wires (e.g., for power, transmission of data, etc.) may extend from the PCB in a mesh, which is also flexible. Alternatively, in certain example embodiments, the wires may be replaced by ITO or other suitable leads printed on the glass, thereby possibly providing a more transparent or cleaner arrangement. In either case, the "leads" may be connected to a bus.

The PCB may be located in an area generally not visible from the interior or exterior of the car. Thus, in certain example embodiments, the PCB may be located, for example, proximate to the rear view mirror. Optionally, the PCB may be further obscured from sight via a black protective coating, which may be printed on or formed around the PCB in the case that the windshield is not protected, or may be a black fit of the windshield itself. In addition to concealing the PCB from ordinary view, such a protective cover also may help to protect the PCB and/or its components from UV radiation. Furthermore, in certain example embodiments, the rain sensor and PCB may be sandwiched between surfaces 2 and 3 during lamination. Locating the rain sensor and PCB here also may help protect the rain sensor components from UV radiation by virtue of the material comprising the laminating layer (e.g., the PVB). An IR reflecting layer may still be coated on surface 3 of the windshield.

The rain sensor, flexible PCB, and leads all may be flexible. As above, this configuration advantageously may enable the rain sensor to conform to the shape of the windshield and also increase resiliency. Although slight deformation of the rain sensor, flexible PCB, leads, and/or components thereof may occur, e.g., by forces generated during lamination, heat, etc., baseline data may be collected after such processes (e.g., after lamination, etc.) so that the rain sensor algorithms are calibrated to take into account such changes. Also advantageous is the fact that the location and structure of the rain sensor, flexible PCB, and leads are unitized, thereby reducing the impact of shocks, vibrations, moisture, debris, etc.

Figure 38:
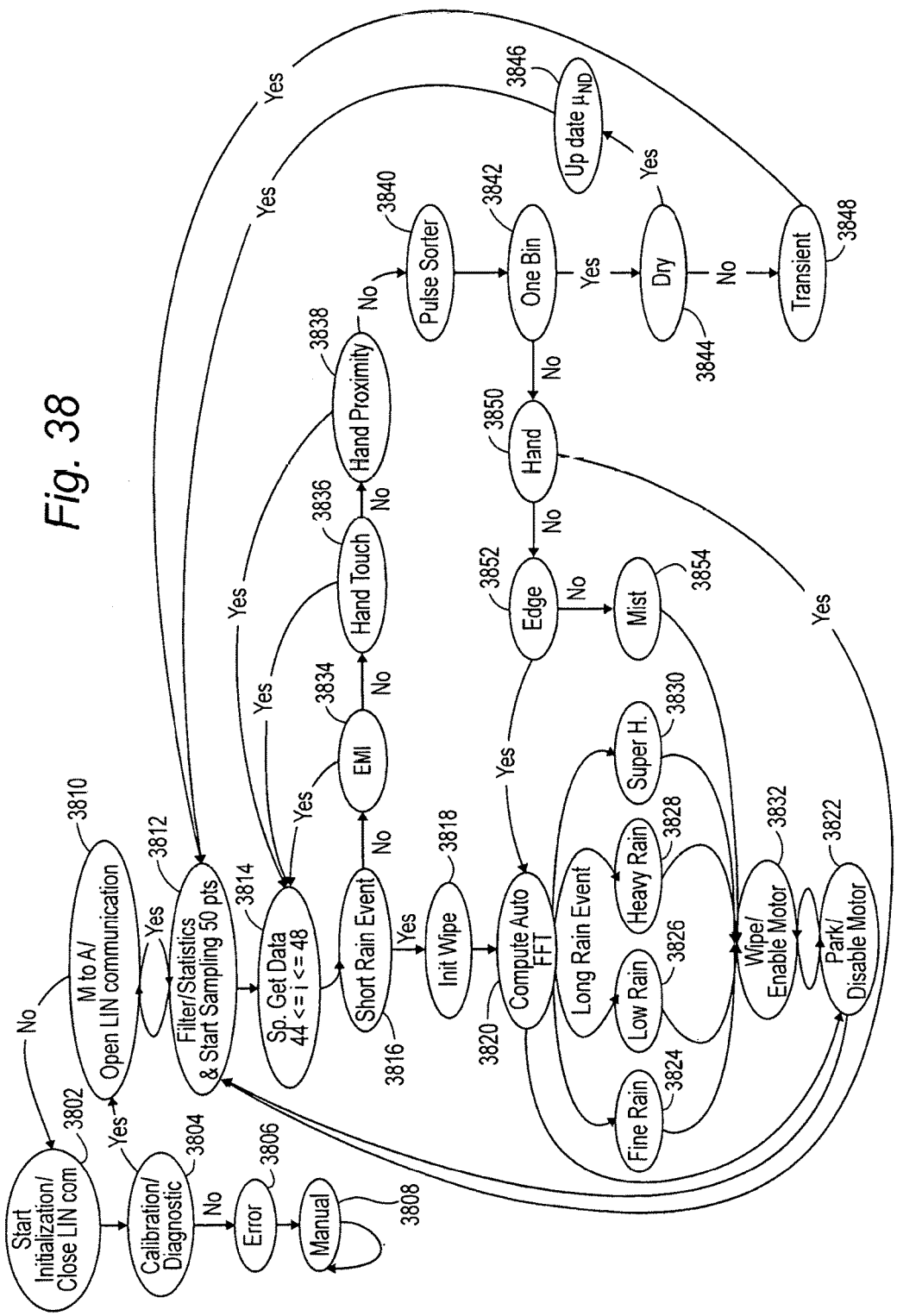
FIG. 38 is an exemplary flowchart or state diagram showing how windshield wipers may be actuated in accordance with an example embodiment.

FIG. 38 is an exemplary flowchart or state diagram showing how windshield wipers may be actuated in accordance with an example embodiment. In 3802, the system is started or initialized. If a communication to the LIN bus is already open, it is closed and/or reset. In 3804, the rain sensor including its capacitive arrays are calibrated or put into a diagnostic mode. This may enable baseline data to be gathered. If the calibration or diagnostic step fails in 3804, an error is generated in 3806 and the system is put into manual mode 3808. Alternatively, a user may initially put the system into manual mode 3808.

After calibrations are complete in 3804, LIN communication is opened in 3810. Filtering and/or statistics are applied in 3812 to a first buffer, which is filled over a first sampling interval. For example, 50 data points may be gathered over a predetermined time interval. A second buffer is filled with data from the first buffer in 3814. The second buffer may take only a subset of the data in the first buffer for analysis. For example, it may draw only the 44th through 48th data points.

Using the data in the first and/or second buffers, the system determines if there has been a short rain event in 3816. Here, as below, the determination of the existence of a perturbation (e.g., moisture, debris, etc.) may be determined using the techniques set forth above, including the matching of the signals from the capacitive arrays to predefined waveforms, performing auto- and/or cross-correlations, etc.

If a short rain event is detected in 3816, then a wipe is performed in 3818. The system may further classify the type of rain or moisture on the windshield and take further action appropriate for the type of rain. Thus, in 3820, a transform (e.g., a Fast Fourier Transform or FFT) is performed on the data. Then using the transformed data, the rain is classified as being one of a fine rain (e.g., something more than a fine mist) 3824, a low amount of rain 382, a heavy rain 3828, or super-hydrophylic rain 3830 (e.g., which tends to overwhelm the windshield). The wipers may be actuated or enabled in 3832 at a speed appropriate for the type of rain. They optionally may be temporarily parked or disabled in 3822 (which also may performed if the data cannot be transformed in 3820, or if the transformed data does not match a known rain pattern. The system may then return to 3812 to re-populate the first buffer, etc.

If a short rain event is not detected in 3816, the system determines whether EMI has affected the capacitive array(s) in 3834. If not, the system determines whether a hand touching the windshield has affected the capacitive array(s) in 3836. If not, the system similarly determines whether a hand (or other living or non-living article) coming into proximity with the windshield has affected the capacitive array(s) in 3838. If so in any of 3834, 3836, and 3836, the system returns to 3814 to re-populate the second buffer.

If no effects are attributable to EMI, a hand touch, or a hand coming into proximity with the windshield, a pulse sorter arranges the data from the first buffer in 3840. If the pulse-sorted data from 3840 fits into one bin as determined in step 3842 (e.g., there are no "edges" detected and thus the data is differentiable at all points), then the system determines whether the window is dry in 3844. If it is not, then there has been a transient change in capacitance 3848, which may be caused by, for example, a change in exposure to sun, wind, etc. In such a case, the system returns to 3812. If, however, the result of 3844 is different, the average baseline values for the capacitive arrays are updated in 3846, and the system returns to 3812. In this latter case, the system effectively may "learn" about the conditions and improve the accuracy of wipes.

If there is not one bin detected in 3842, the existence of a hand on the windshield is again determined in 3850. If a hand touch has been detected, the system returns to 3812. In 3852, the presence of any edges at all is determined. If there are any edges, then the system proceeds to 3820 to indicate that there is some kind of rain event other than a short rain event. If there are not any edges, then there is a mist 3854, and the motor is enabled and/or wipes commence in 3832.

As such, a feature of certain example embodiments is that the rain sensing code may perform an automatic normalization of the capacitance values. Over the course of day (even without water), the capacitance can change from about 0.6 pF to about 1 pF. This may be attributed to glass temperature changes. Certain prior art techniques simply try to subtract two signals, making the assumption that the difference does not vary with temperature. In fact, it has been determined that this is not correct. The normalization procedure of certain example embodiments helps ensure that sensing parameters do not have to change. There is nothing to calibrate, as the value is normalized by the mean. Accordingly, each time the rain sensing code goes through the "dry mode" on the state diagram, the normalization process occurs.

Certain example embodiments relate to light sensors. The light sensors may be mounted to the flexible PCBs described above. The connection of the light sensor to the flexible PCB may be accomplished using a flip-chip, wherein the light sensor is mounted to the back surface of the PCB (e.g., the surface of the PCB that faces away frump the vehicle exterior). In general, flip-chip mounting is one type of mounting used for semiconductor devices, such as integrated circuit (IC) chips, which reduces the need for wire bonds. The final wafer processing step deposits solder bumps on chip pads, which connect directly to the associated external circuitry. The processing of a flip-chip is similar to conventional IC fabrication. Near the end of the process of manufacturing a flip-chip, attachment pads are metalized to make them more suitable for soldering. This metalizing typically includes several treatments. A small solder dot is deposited on each of the pads. The chips are cut out of the wafer, as conventional. Additional processing generally is not required, and generally there is no mechanical carrier at all. When a flip-chip is attached to a circuit, it is inverted to bring the solder dots down onto connectors on the underlying electronics or circuit board. The solder is then re-melted to produce an electrical connection. This leaves a small space between the chip's circuitry and the underlying mounting. In most cases an electrically-insulating adhesive is then used to provide a stronger mechanical connection, provide a heat bridge, and to ensure the solder joints are not stressed due to differential heating of the chip and the rest of the system. The resulting completed assembly is much smaller than a traditional carrier-based system. The chip sits on the circuit board, and is much smaller than the carrier both in area and height.

The light sensor of certain example embodiments "sees" through a small hole (e.g., a pinhole) or slit. The small hole extends through a black frit or opaque layer (when such a layer is provided) and through the PCB. A pinhole design allows the light sensor of certain example embodiments to "see" what is in the line of view. It also acts as a form of lens in and of itself. Thus, in certain example embodiments, the need for a lens may be reduced and sometimes even completely eliminated. This is a change from conventional light sensor designs, which typically require such lenses. When an opaque layer is implemented, including only a small pinhole therein advantageously may shield and/or protect the non-light sensing components of the PCB, e.g., from UV, and/or effectively hide such components from a driver's field of vision.

Although certain example embodiments do not require a lens, in certain other example embodiments, a lens may be used in connection with the light sensor. In such a case, the lens may be a substantially flat, defractive lens. Such a substantially flat, defractive lens may be located over the light sensor (or light sensing arrays of the light sensor described in greater detail below).

The light sensor of certain example embodiments may be able to detect the presence of light and/or the amount of lux. This may be possible over the UV, IR, and visible light spectra. As such, the light sensor of certain example embodiments may detect the presence and amount of lux UV, IR, and visible light within a line of sight from the vehicle. Optionally, the same and/or similar measurements may be taken from within the vehicle. The internally oriented arrays of the light sensor of certain example embodiments may be used for baseline comparisons of changes in ambient light. For example, in certain example embodiments, the internally oriented arrays of the light sensor may be compared with the externally oriented arrays so as to determine when the vehicle is within a tunnel, for example. Similarly, at least some of the externally oriented arrays may be pointed towards the sky for baseline purposes (e.g., to determine whether the vehicle is under cloud cover).

Figure 39:
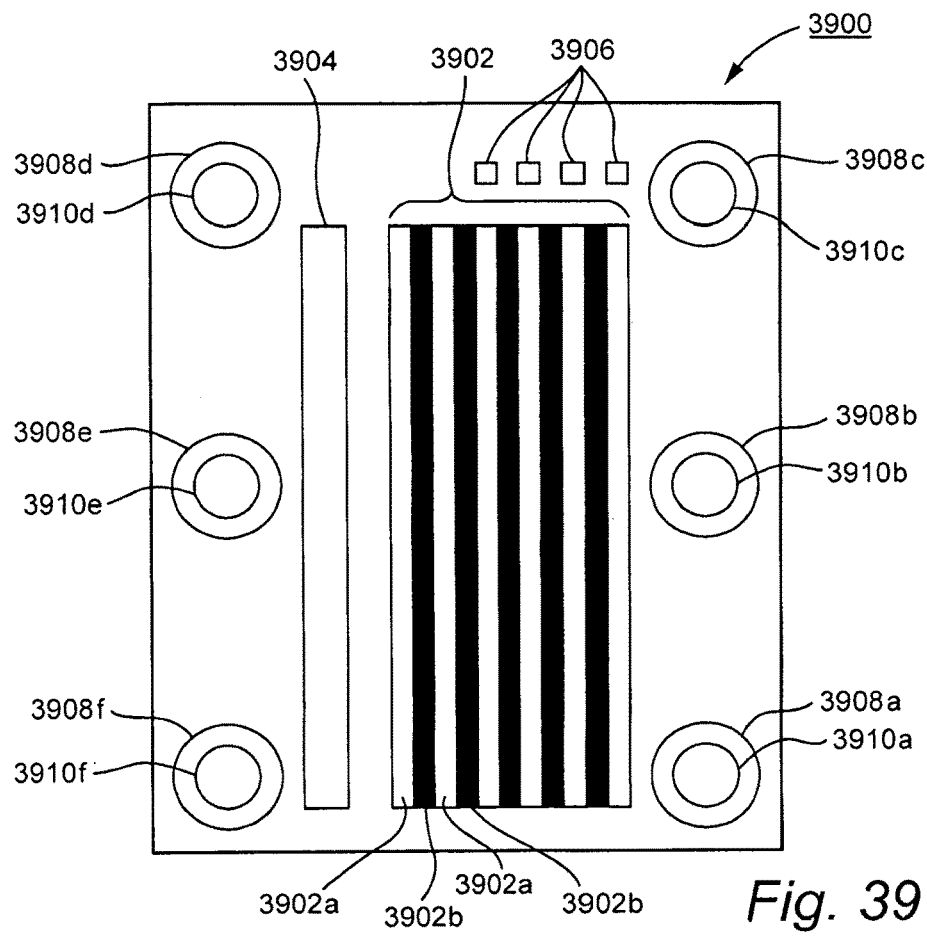
FIG. 39 is an illustrative view of a light sensor flip-chip design in accordance with an example embodiment.
Figure 43:
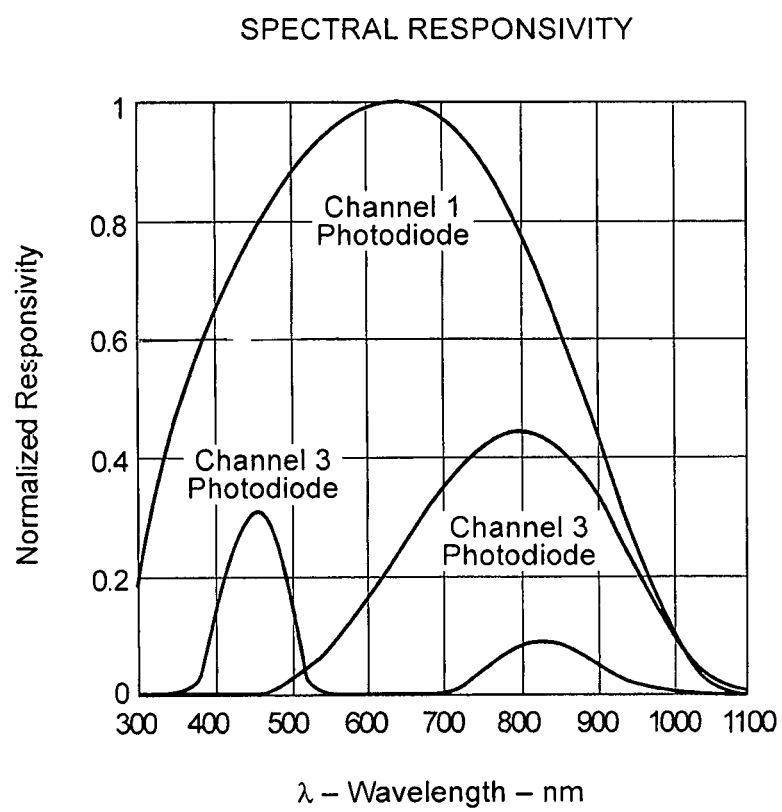
FIG. 43 is a graph showing the spectral responsivity of the photodiodes of the three channels of an illustrative light sensor according to an example embodiment.

FIG. 39 is an illustrative view of a light sensor flip-chip design 3900 in accordance with an example embodiment. A first array 3902 is provided. The first array 3902 includes bare silicon die 3902a in this photo-diode, and each silicon die is surrounded or covered by metal 3902b. In certain example embodiments, the metal 3902b may be used to generate baseline data in certain example embodiments. This first array 3902 may be multiplexed so as to "see" light in a broadband of from about 300 nm to about 1100 nm (and therefore including UV, visible and IR light), with responsivity peaking at about 650 nm, on a first channel, as well as on a third channel "seeing" light from about 400 nm to about 550 nm and peaking at about 500 nm (and thus "seeing" visible light). A second array 3904 may "see" light on a second channel, ranging from about 500 nm to about 1100 nm and peaking at about 800 nm (and thus "seeing" IR light). FIG. 43 is a graph showing the spectral responsivity of the three channels of an illustrative light sensor according to an example embodiment. The channels may be digital or analog channels in certain example embodiments, and in certain example embodiments, one or more processing registers 3906 or other memory locations may be used to help buffer, convert, or otherwise process light-related data. One or more separate analog-to-digital converters also may be provided.

No lens is shown in FIG. 39. This is because, as noted above, a pinhole and proximity of the sensor to the pinhole may render a lens optional. Of course, in certain example embodiments, a lens may be provided. As noted above, the lens may be a defractive index lens. The light sensor of certain example embodiments may have a frontal field of view of from about 50-70°, more preferably from about 55-65°, and still more preferably of about 60°, the angles being on either side of normal or being total visible angles.

A plurality of legs 3908*a-f* are provided. Each of the legs 3908*a-f* has a solder connection pin 3910*a-f* respectively associated therewith. In certain example embodiments, the legs 3908*a-f* may be made of ceramic or glass, and the solder connection pins 3910*a-f* may include metal. In certain example implementations, the pins 3910*a-f* may correspond to voltage or power supply, address, ground supply, clock, interrupt, and data pins. Of course, it is possible to use other pins alone or in combination with such arrangements. An interrupt function optionally may facilitate the capture of only large changes so as to help reduce the wasting of memory.

The light sensor may be convert light intensity to a digital signal output, which may be sent to an I²C link of a vehicle for processing by suitable programmed logic circuitry (which may be any suitable combination of hardware, software, firmware, and/or the like). Channels 1 and 2 described above optionally may be "muxed" together to derive UV channel data. Upon completion of the conversion from analog to digital signals, the conversion results may be sent across their respective channels. The transfers may be double-buffered to maintain data integrity.

Light sensors may be obtained and modified from commercial sources so as to function with certain example embodiments. For example, light sensors commercially available from TAOS (e.g., modified ALS FlipChip models TSL2560FC and TSL2561FC), Micron, and/or other sources, may be used.

Figure 40:
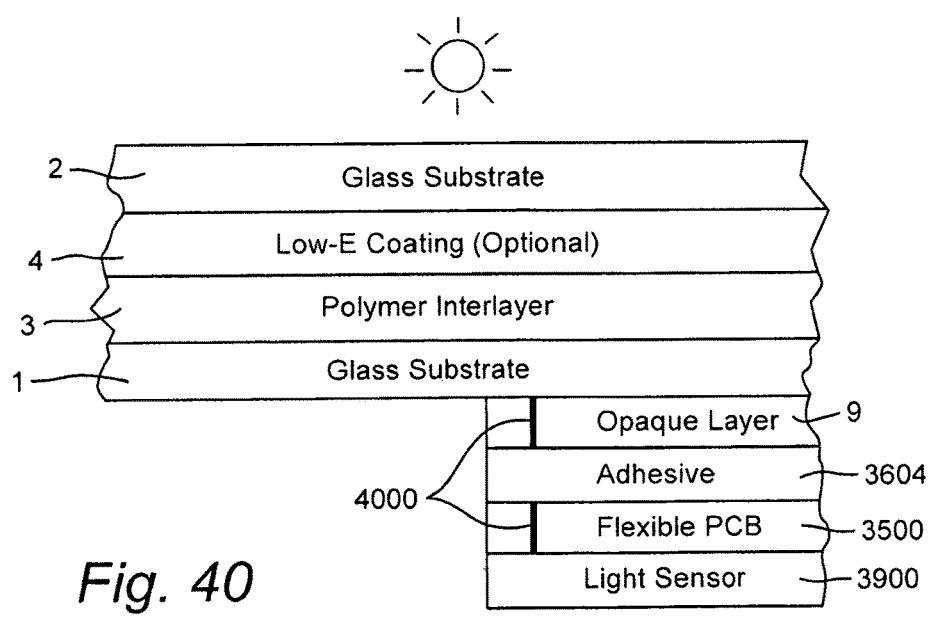
FIG. 40 is a cross-sectional view of a light sensor supported by an inner surface of an inner glass substrate according to an example embodiment of this invention.

FIG. 40 is a cross-sectional view of a light sensor supported by an inner surface of an inner glass substrate according to an example embodiment of this invention. Similar to the example embodiment shown in FIG. 37(*a*), in FIG. 40, a flexible PCB 3500 is connected to an opaque layer 9 via an adhesive 3604. The opaque layer is formed on an interior surface (e.g., a surface closest to the vehicle interior) of an inner glass substrate 1. The inner glass substrate 1 and the outer glass substrate 2 are laminated together via a polymer interlayer 3 (e.g., of PVB, EVA, etc.). A low-E coating 4 optionally may be applied to one or more of the interior surfaces of the substrates 1, 2. A hole 4000 is formed in the opaque layer 9 and the flexible PCB 3500. This hole 4000 may function as a lens, as described above. The light sensor 3900 is connected to the flexible PCB 3500 on a surface thereof that is closest to the vehicle interior using flip-chip mounting. Similar to above, the light sensor 3900 and flexible PCB 3500 may be mounted elsewhere in the windshield assembly (e.g., supported by surface 2 or 3, or floating within the polymer interlayer 3). An IR reflecting layer may or may not be deleted in certain example embodiments, e.g., depending on where the light sensor is located, the total effect of the IR reflecting layer, etc.

This example arrangement is advantageous for a number of reasons. For example, conventional light sensors typically include a plastic casing to protect the chips. Typical automotive testing requires functionality from about −40° C. to 105° C. The plastic casings protecting the chips in conventional design arrangements, however, have been found to melt at only about 85° C. This is troublesome, in that the glass substrates often reach temperatures of up to about 120° C. In contrast to typical designs, the design arrangement of certain example embodiments is stable up to at least about 120° C. This is true for several reasons. First, there is no plastic encasement to melt. Second, the chips and sensor itself are not in direct contact with the glass. That is, the ceramic legs and solder help insulate the chips from the heat. Additionally, the flexible circuit board (which may contain FR-4 and metal inner layers) may help deflect heat away from the light sensor.

The design arrangement of certain example embodiments also is advantageous, as water tends not to condense in front of or infiltrate the pinhole. This is because the arrangement of certain example embodiments may be protected by a substantially transparent adhesive (e.g., a tape and/or optional additional glue). Additionally, there is little movement because of the secure seal. Moreover, when there is movement, the entire PCB moves and thus baseline data may be maintained or recalculated.

Figure 41:
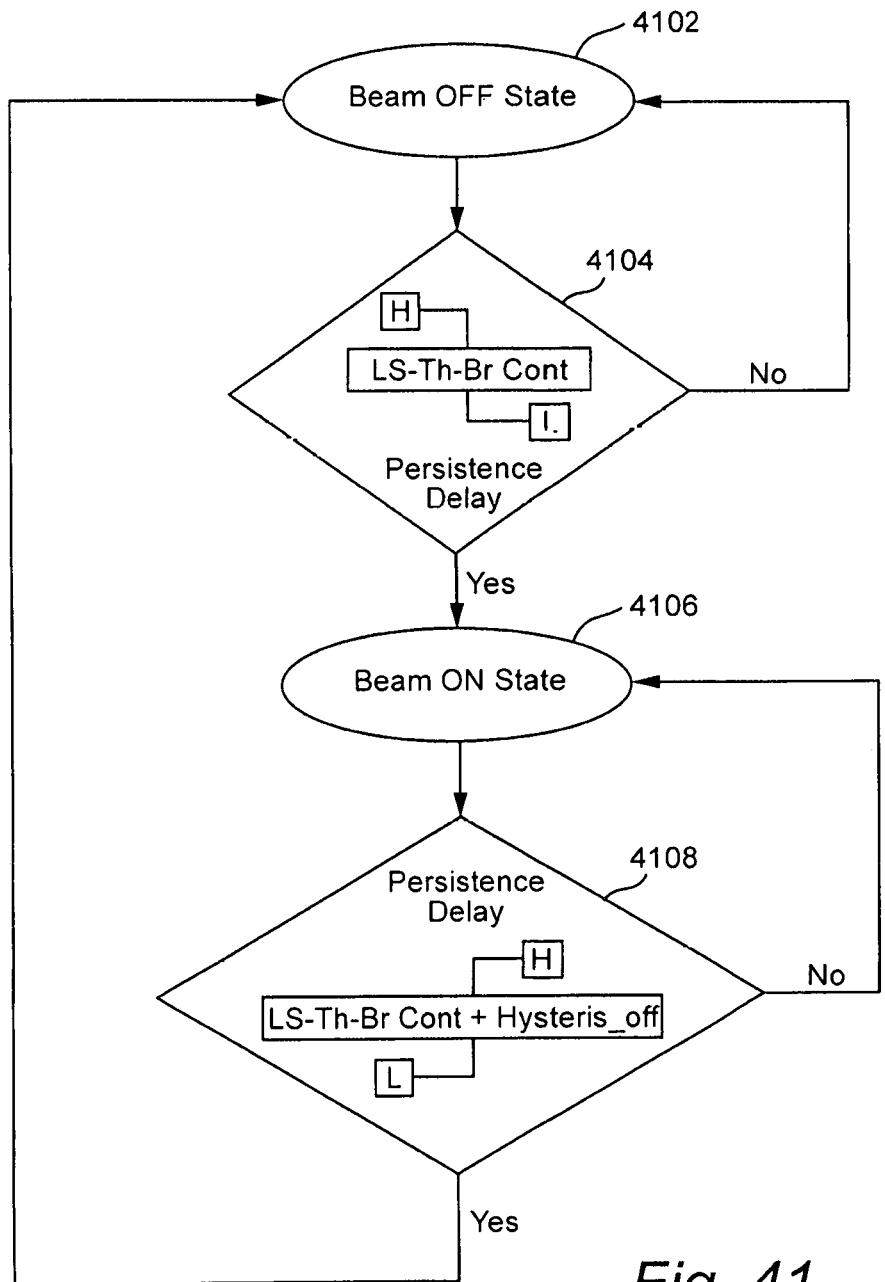
FIG. 41 is an illustrative flowchart or state diagram illustrating how lights may be turned on or off in dependence on data from the light sensor in accordance with an example embodiment.

Channel data from the light sensor may be compared to determine when and how to turn on/off the lights of a vehicle. The comparisons may be based on absolute values, ratios of channel outputs, etc. FIG. 41 is an illustrative flowchart or state diagram illustrating how lights may be turned on or off in dependence on data from the light sensor in accordance with an example embodiment. In FIG. 41, state 4102 represents a beam off state, and state 4106 represents a beam on state.

A FIFO buffer is built in certain example embodiments. In certain example embodiments, data for the buffer may be taken at a frequency of about 25 Hz, which generally is what is considered the rate at which the human eye sees. Of course, data may be sampled at other rates, which may be higher or lower than 25 Hz. A frame will comprise a predetermined number of points gathered at a predetermined interval. For example, frames may be captured at 25 Hz, with each frame including 50 points gathered at about every 40 ms. In certain example embodiments, the values from the buffer may or may not be filtered.

In essence, the light sensor may look for a stable edge change in the data in the buffer. If the edge change passes through a predefined threshold, the state should be switched. If the data is flat or substantially flat, there is no change in ambient light, and if the data does change but does not pass through a threshold, the states should not be switched.

Referring once again to FIG. 41, it is determined in decision 4104 whether the beams should be turned on, and it is determined in decision 4108 whether the beams should be turned off. LS-Th-Br-Cont is a light sensor threshold brightness control, which may be expressed in lux. A typical value for LS-Th-Br-Cont has been determined to be about 2,500 lux. H denotes a high level lux value, which has been determined to be about 4,000 lux or higher. L denotes a low level lux value, which has been determined to be about 1,000 lux or lower. Thus, if the signals pulled from the light sensor (e.g., in the butter) pass from H to L through LS-Th-Br-Cont, the lights may be changed. The change to low may be required to persist for a predetermined time. This time may be the equivalent of one frame, a half frame, etc. Here, and below, the persistence delay may prevent flashes of light or transient changes in ambient light from erroneously triggering a change in state.

In decision 4108, a hysteresis factor is introduced. As such, Hysteris_Off has been determined to be about 5,000 lux. It is added to LS-Th-Br-Cont to determine when to toggle to another state. Thus, if the signals pulled from the light sensor (e.g., in the buffer) pass from L to H through the sum of Hysteris_Off and LS-Th-Br-Cont, and the persistence delay condition is met, then the state may be changed.

The above-described methodology has been determined to work particularly well when a vehicle is stationary or traveling below a certain critical speed. If however, the vehicle meets or exceeds a certain speed threshold, denoted V-speed-th, then the LS-Th-Br-Cont may need to be incremented in certain example embodiments. For example, if the vehicle is traveling at a speed of about 100 km per hour or higher, the a delta of about 1,000 lux may be added to the LS-Th-Br-Cont.

This delta will be added to the LS-Th-Br-Cont until the car falls below V-speed-th less a V-speed-hysteresis. In such a case, the delta may be returned to 0. A typical value for V-speed-hysteresis is about 30 km per hour.

This example technique may be used with a single channel. Alternatively, or in addition, this example technique may be further refined by comparing the data over the three channels listed above. In the simplest case, the threshold may be set using channel 1 (e.g., the broadband channel). Decisions about when to turn on light may be based on 2 or more of the channels. In a more complicated case, edges may be detected across all three channels. Thus, certain example embodiments involve edge detecting in space and time, as well as wavelength.

Indeed, changes in the channels may be correlated. Channels 1 and 2 vary lineally. Thus, if channels 1 and 2 change, then the light state should also be changed. This kind of change would suggest a big change in the visible, ambient light. If channel 1 changes but channel 2 does not change, there should be no change in state. This result is indicative of a change in the IR spectrum only. This may occur, for example, when clouds block the sun. If there is a change in channel 3 and not channel 2, there should be a change in state. This may occur, for example, when a car enters into a tunnel.

Figure 42:
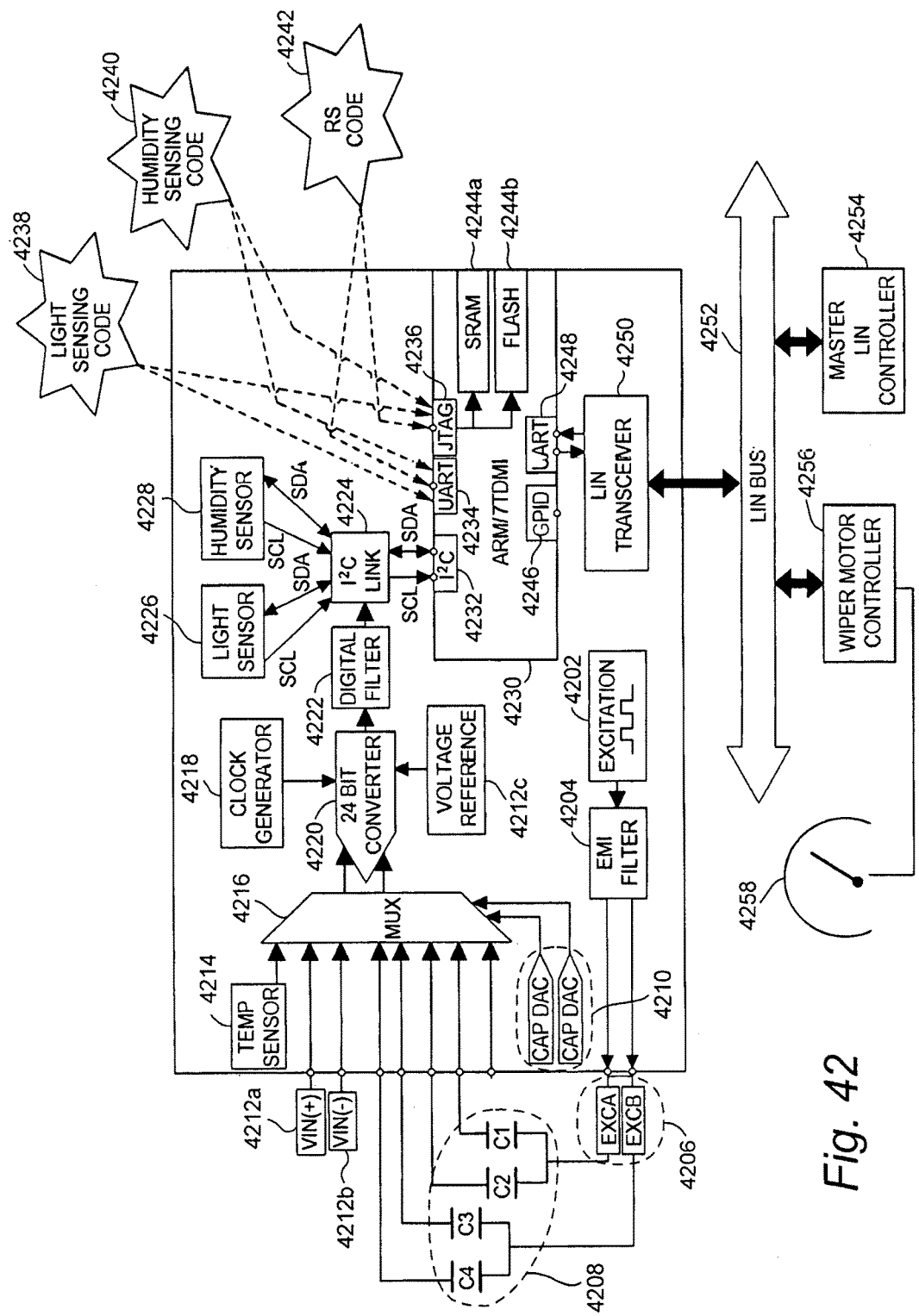
FIG. 42 shows example capacitive array circuitry according to an example embodiment.

FIG. 42 shows example capacitive array circuitry according to an example embodiment. In FIG. 42, excitations 4202 are filtered by an EMI filter 4204. Excitations signals EXC A and EXC B are processed by the capacitors in the capacitive array 4208. A multiplexer 4216 multiplexes the signals from the capacitive array 4208, capacitive digital-to-analog converters 4210, positive and negative voltage ins 4212*a-b*, and temperature sensor 4214. The multiplexed signal from multiplexer 4216 is fed into a 24-bit converter 4220, along with a clock signal generated by clock generator 4218 and a reference voltage 4212*c*. This signal is digitally filtered using a digital filter 4222 and fed into an I$^2$C link 4224. Output from the light sensor 4226 and humidity sensor 4228 also are fed into the I$^2$C link 4224.

The I$^2$C link 4224 is connected to an I$^2$C port 4232 of the processor 4230. Each of the light sensing code 4238, humidity sensing code 4240, and the rain sensor code 4242 are connected to first UART and JTAG ports 4234 and 4236 of the processor 4230. The codes may be implemented as programmed logic circuitry (e.g., any suitable combination of hardware, software, firmware, and/or the like), and/or may be tangibly stored as instructions on a computer-readable storage medium. The first JTAG port 4236 also is connected to one or more memory locations. The memory locations shown in the FIG. 42 example are SRAM and flash memory locations 4244*a* and 4244*b*. The processor 4230 also includes a GPID port 4246 and a second UART port 4248.

The second UART port 4248 is connected to a LIN transceiver 4250 which is ultimately connected to a central LIN bus 4252 of the vehicle. The LIN bus 4252 is connected to a master LIN controller 4254, as well as a wiper motor controller 4256. The wiper motor controller 4256 ultimately controls the wipers 4258 in dependence on the excitations 4202.

By way of example and without limitation, the AD7745 and AD7746 are a high resolution, $\Sigma$-$\Delta$ capacitance-to-digital converters that may be used in connection with certain example embodiments. Of course, it will be appreciated that other $\Sigma$-$\Delta$ capacitance-to-digital converters may be used in connection with certain example embodiments. Also by way of example and without limitation, the microprocessor may be an ADuC7128 microcontroller, which may be used in connection with an ARM7TDMI core. Of course, it will be appreciated that other microprocessors and/or microcontrollers may be used in connection with certain example embodiments.

It is noted that herein the use of the word "fractal" is not limited to a perfect fractal pattern, and instead also covers quasi-fractals such as the polygonal elements and geometric patterns having self-affinity such as those discussed for example in U.S. Pat. Nos. 6,809,692, 6,937,191, and/or 7,015,868 which are all incorporated herein by reference.

It is noted that while capacitors C1-Cn (where n is two, four, ten or any other suitable number) are preferred as the sensing devices in certain example embodiments of this invention, it is possible to use other types of sensing devices instead of or in addition to the capacitors in certain example instances.

In certain example embodiments, changes in field strength as low as 10 nV/cm can be detected at the receiving electrodes using a multi-channel on-chip 24 bit resolution sigma-delta converter. Sensing areas up to (1500 square mm) three times larger than current glass-based optical sensors also may be achieved in certain example embodiments.

Multiple layers of the distributed array of capacitors may be stacked on top of each other and electrically isolated and shielded from each other. In this compact design, the length of the excitation and return lines to the capacitors are kept low, while all electronics required are embedded on the sensor. Prior to placement, both the glass surface (e.g., surface 4 or between surfaces 2 and 3) and flexible sensor PCB may be cleaned and treated with a polymeric silicone based wetting agent. An ultra-thin double sided adhesive may be applied to the outward sensing side of the PCB. The latter is then affixed to the windshield surface by roll pressing. The flexible PCB conforms to the glass surface. The use of the wetting agent helps reduce the likelihood of the formation of air gaps or bubbles. The curing process for the adhesive can be as simple as a prescribed heat gun treatment. The adhesive used may be UV and humidity resistant. In addition, or in the alternative, in the area of placement on the glass, a black frit may be used to provide extra protection to solar UV weathering. A polymer overcoat may be added to insulate and environmentally seal the circuit.

The flexible PCB may be made of a material that possesses high heat resistance, dimensional stability, dielectric strength, and flexural capability suitable for automotive environments. The flexible PCB may also combine the sensor pattern's double-sized circuits with complex interconnections, shielding, and surface-mounted devices in a multi-layer design. This new configuration of the EFS allows for a system that has increased accuracy in the placement of the overall sensor on the windshield. The flexural capability of the polymer allows the sensor pattern to conform to the curvature of the windshield with no moving parts and removes the need for hermetic sealing. In addition, decoupling two distinct sets of electrodes (e.g., on each side of the PCB) allows the sensor to discriminate between outside and inside conditions and take appropriate actions to only wipe when water is detected on the exterior of the windshield by the "wet" capacitors while the defogger will come on when the "dry" capacitors read a threshold value.

As alluded to above, it is possible in certain example embodiments to laminate one or more flexible PCBs with moisture and/or light sensors thereon, within the two sheets of glass or glass and polycarbonate, etc., to form a sensor farm. In certain implementations, a light and capacitive moisture/touch/other disturbance detector may be provided on a common side of a PCB, potentially adjacent to one another. Circuitry may be sandwiched between EVA or PVB interlayers and the glass, with the leads to the outside (e.g., the Vbat, GND, and Lin bus lines) potentially being the only exposed parts in certain example embodiments. In certain example embodiments, the flexible PCB may be coated with a fine silicone spray that acts like a barrier between the PCB and plasticizers in the PVB. This example arrangement may be advantageous to an installer and a final customer, as the sensor may become ruggedized since it is in a near hermetic. This arrangement may be provided in place of, or together with an O-ring to cocoon the electronics. With the use of an optional small solar cell, Li-polymer or Li-ion battery, and a WiFi enabled chip, it becomes possible to embedded everything in the glass without having any tether coming out of the glass. Providing a materials around the sensors may also make them EMI insensitive.

The inventors of the instant application have recognized that the example moisture and/or light sensing techniques described herein may in addition or in the alternative be applied to refrigerator/freezer or other merchandiser systems. For instance, the example moisture and/or light sensing techniques described herein may be used in connection with a deicer/defogger to reduce the likelihood of condensation forming in a refrigerator/freezer merchandiser.

Current refrigerator/freezer systems display fresh and frozen food products in a product display area and include glass doors to provide clear visibility of the food product to potential consumers. Unfortunately, however, condensed moisture tends to accumulate on the exterior surface of the cold glass, which obscures the view of the product in the merchandiser. The moisture in the relatively warm ambient air of the store can condense on the outside surface of the glass door. Similarly, moisture can also or alternatively condense on the cold inside of the glass door, e.g., when it is opened. This is a problem for doors that do not use an insulating glass (IG) unit configuration, as well as for some IG unit configurations.

Some current approaches to the condensation problem on the inner glass pane involve applying a hydrophilic coating to reduce the optical distortion induced by the condensed water. Further improvements to this approach would be desirable, however, in that the inner pane tends to saturate when the door is open for extended periods of time at which point, for example, a thick layer of ice may develop on the glass, requiring several minutes to clear. Another drawback associated with this approach is the relatively poor mechanical durability of the hydrophilic treatment.

Thus, it will be appreciated that there is a need in the art for a more mechanically robust and faster-acting solution to the condensation problem.

Some door manufacturers have attempted to overcome these and/or other issues by continuously or constantly applying current to a conductive layer so as to heat the inner surface of the door. Unfortunately, however, this heating technique heats up the whole glass bulk and consequently consumes a large amount of energy.

In some cases, the glass doors are highly insulating IG units or laminated configurations with high R-values. Such configurations are designed to reduce the amount of heat from the outside encroaching into the cold volume. As a result, when the defogging cycle is initiated, the compressor has to work harder to keep the refrigerator/freezer at its set temperature and thus consumes more energy. This inefficiency may be compounded in the repeated cycles of fogging and defogging.

At the other extreme, in configurations with no heating, the condensation on the outside and inside of the glass door may not clear quickly and may obscure the food product in the merchandiser. Long periods of obscured food product caused by condensation may detrimentally impact sales of the products.

Some glass doors include a Fabry-Perot structure metallic-based coating or semi-conducing film (e.g., of or including tin oxide) provided on the glass door to remove condensation and/or fog. The ohmic coating may supply heat to the glass door via current flow through the coating caused by a supply of electrical potential or electricity from the merchandiser. Typically, the heat applied to the glass door is controlled by a controller based on a duty cycle. These duty cycles are varied between an "on" state (heat applied to the door) and an "off" state (heat not applied to the door) so as to regulate the time that heat is applied to the glass door. They generally are defined by the percentage of time that the duty cycle is in the "on" state.

Some refrigerator/freezer units include a knob or other manual control that may be used by an operator to set the percentage of time that the duty cycle in the "on" state based on, for example, experience of the operator. Other existing merchandisers use a sensor to sense parameters of the ambient environment surrounding the merchandiser such as, for example, humidity, temperature, etc. A controller is in electrical communication with the sensor and may help determine a duty cycle to remove condensation from the glass door based on the sensed parameters.

Typically, sensors of conventional control systems are attached to the merchandiser at a relatively large distance from the glass door and the refrigerated/frozen display area (e.g., on an exterior wall of the merchandiser, on a wall adjacent to the merchandiser, etc.) to help avoid an adverse impact on the sensed parameters caused by infiltration of relatively cold, dry air when the glass door is opened. However, placement of conventional sensors at relatively long distances from the glass door limits the effectiveness of the sensor to accurately measure ambient conditions adjacent to the glass door. As a result, the duty cycle determined by the controller may not be adequate to clear the glass door because insufficient heat may be supplied by the resistive coating. Insufficient heat applied to the glass door can cause poor dissipation of condensation and fog. Similarly, inaccurate measurements by the sensor may cause the controller to supply too much heat to the glass door, thereby potentially resulting in increased energy costs.

Certain example embodiments relate to an active, intelligent defogging system for a refrigerator/freezer merchandiser that heats up a glass surface to reduce (and sometimes even eliminate) condensation on the glass surface. Advantageously, certain example embodiments provide for fast clearing time for fogged glass doors (e.g., related to water condensation on the inner-cold surface), and certain example embodiments advantageously improve energy efficiency. More particularly, certain example embodiments relate to a water-sensing-feedback technique that initiates a fast surface heating process for a refrigerator/freezer door upon the detection of the presence of moisture using a multi-functional sensor affixed to the glass surface. The sensor may be the same as or similar to a capacitive array rain and light sensor described herein. The sensor may trigger appropriate pulse heating using a LIN protocol in response to changes in glass surface moisture. The heating process may stop once the water is gone. The sensor may be small in size so that it is easily concealed and/or has a reduced visible impact on the display capability of the door. In certain example embodiments, two sensors may be affixed to the glass door, e.g., at the top and bottom of the unit, at the left and right areas of the unit, along diagonals, etc. The sensors may be bonded to the inside surface of the glass within an IG configuration (e.g., on any appropriate surface such as, for example, on surface 5), be laminated inside the glass, etc. When multiple sensors are included, each may be associated with a respective zone. Thus, in certain example embodiments, multiple sensors sensing condensation, etc., within respective zones may be provided. A controller or at least one processor may receive signals from the sensors and actuate a heating system in dependence on such signals. These signals may be indicative of the presence and/or type of condensation, debris, or other disturbance to the system, and the controller or processor(s) may take an appropriate action (e.g., initiating heating in one or more corresponding zones, taking no action in the event that the disturbance is a human touch or a dirt, etc.).

Figure 44:
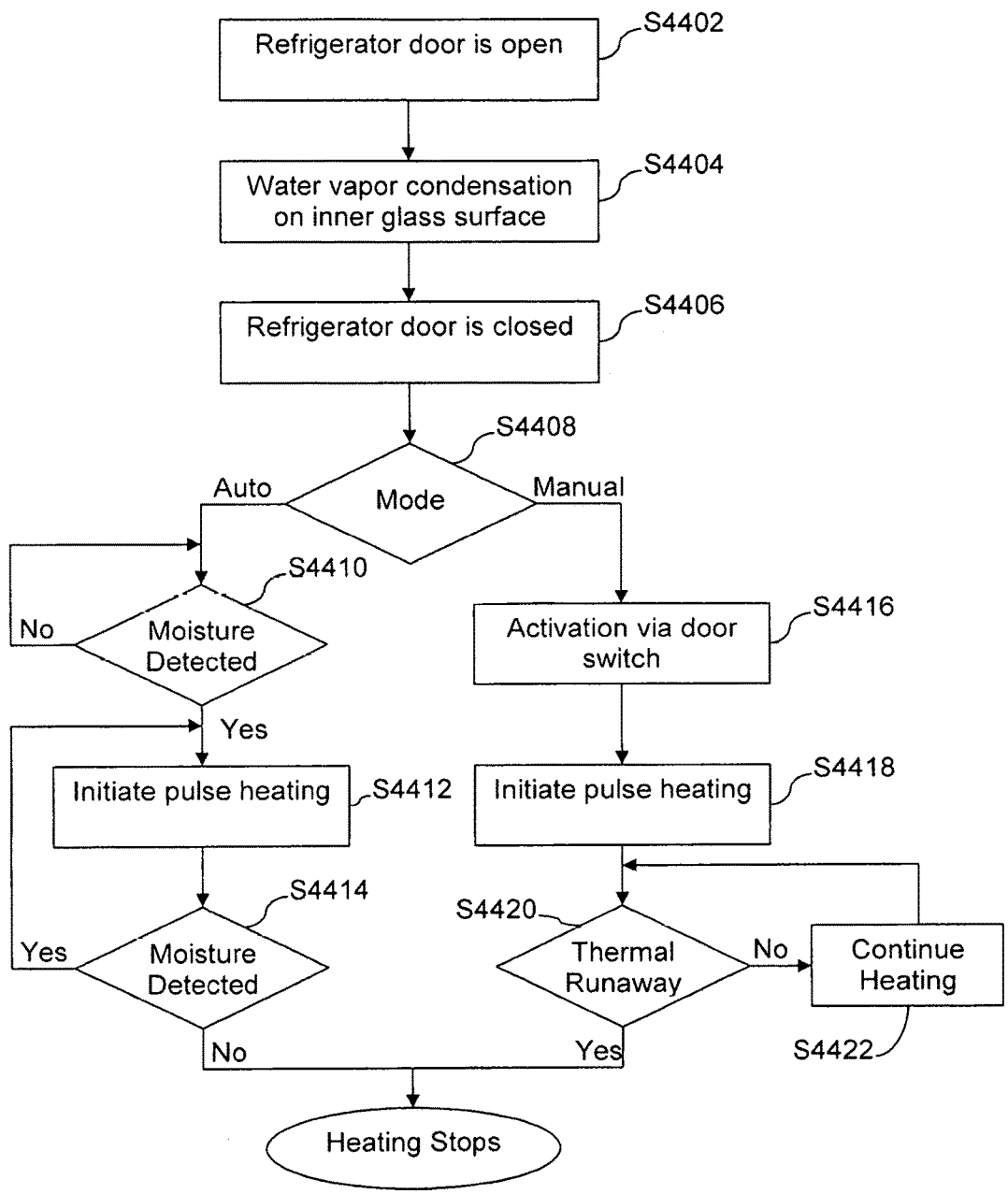
FIG. 44 is an illustrative flowchart illustrating how a moisture sensor may be used in connection with a refrigerator/freezer merchandiser according to an example embodiment.

Certain example embodiments may incorporate a sensor connected to a power supply. Once pulsing is initiated (e.g., once triggered by an electromechanical, magnetic, or other switch or device), the resulting heating of the conductive coating may result in an increase in the coating resistance that would be sensed by the power supply as a change in the circuit load. FIG. 44 is an illustrative flowchart illustrating how a moisture sensor may be used in connection with a refrigerator/freezer merchandiser according to an example embodiment. When a refrigerator/freezer door is opened in step S4402, water vapor condensation may form on an inner surface of the inner glass substrate in step S4404. The door is then closed in step S4406. Certain example embodiments may function in one of two modes, e.g., as shown in the FIG. 44 example flowchart. In an automatic mode, a determination is made in step S4410 as to whether moisture is detected. When moister is detected in step S4410, heating is initiated in step S4412. The type of heating may be a conventional type of heating in certain example embodiments, e.g., wherein an electrical current is passed to a conductive layer. However, in certain example embodiments, pulsed heating may be applied. After the heating, a determination is made in step S4414 as to whether there is moisture. If there is any moisture detected, the flow returns to step S4412 for additional heating. If there is no more moisture detected, the heating stops.

In a manual mode, a door switch rather than an automatic detector may be used to determine whether heating is to be applied. Thus, in step S4416, when a door switch is activated, heating (e.g., of the type(s) described above) is initiated in step S4418. In step S4420, a detector monitors for a thermal runaway. As is known, thermal runaway is a kind of "positive feedback" and generally refers to a situation where an increase in temperature changes the conditions in a way that causes a further increase in temperature. If there is no thermal runaway, the heating is continued in step S4422, and the process again moves to step S4420 to monitor for a thermal runaway. If a thermal runaway is detected in step S4420 (e.g., initially or after some amount of heating), the heating stops.

Figure 45A:
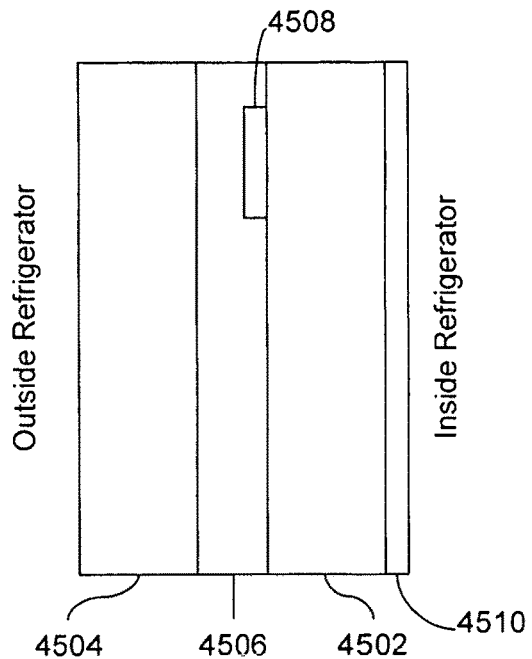
FIG. 45(a) is a schematic, cross-sectional view of a laminated article incorporating a moisture sensor and heating element according to an example embodiment.
Figure 45B:
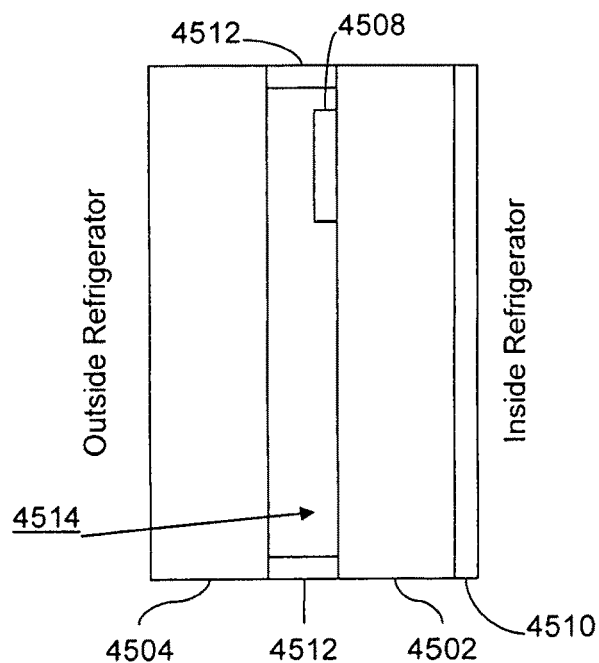
FIG. 45(b) is a schematic, cross-sectional view of an insulating glass (IG) unit incorporating a moisture sensor and heating element according to an example embodiment.

FIGS. 45(a) and 45(b) are exemplary refrigerator/freezer door configurations. More particularly, FIG. 45(a) is a schematic, cross-sectional view of a laminated article incorporating a moisture sensor and heating element according to an example embodiment, and FIG. 45(b) is a schematic, cross-sectional view of an insulating glass (IG) unit incorporating a moisture sensor and heating element according to an example embodiment. Both FIGS. 45(a) and 45(b) include inner and outer glass substrates 4502 and 4504. A moisture sensor 4508 (e.g., of the type described above) is may be located between the inner and outer glass substrates 4502 and 4504 in certain example embodiments. However, in certain other example embodiments, the sensor may be provided on an outer surface of the inner or outer glass substrate 4502/4504.

In FIG. 45(a), a polymer-based interlayer 4506 laminates together the inner and outer glass substrates 4502 and 4504. The polymer-based interlayer 4506 may be any suitable material such as, for example, PVB, EVA, and/or the like. The sensor 4508 in the FIG. 45(a) example may be at least partially surrounded by and/or hermetically sealed in the polymer-based interlayer 4506 in certain example embodiments.

By contrast, in the FIG. 45(b), the refrigerator/freezer door may be thought of as being an insulated glass unit, in that it includes spacers 4512 helping to maintain the inner and outer glass substrates 4502 and 4504 substrates in substantially parallel, spaced apart relation to one another so as to form a gap 4514 therebetween. As alluded to above, the sensor 4508 may be located within the gap 4512 between the inner and outer glass substrates 4502 and 4504 in certain example embodiments.

A transparent conductive coating (TCC) 4510 may be disposed on one or more major surfaces of the inner and/or outer glass substrates 4502/4504. In FIGS. 45(a) and 45(b), for example, the TCC 4510 is disposed on an outer surface of the inner substrate 4502 and thus is adjacent and possibly exposed to the inside of the refrigerator/freezer unit. In different example embodiments, however, the TCC may be provided on an inner surface of the inner substrate 4502 or of the outer substrate 4504 (e.g., adjacent the polymer-based interlayer 4506 or the gap 4514 depending on the overall structure of the door), on an outer surface of the outer substrate 4504, etc. In certain example embodiments, the TCC 4510 may be continuous or patterned. In certain example embodiments, the TCC may be a layer of or including ITO, AZO, Ag, fluorine-doped tin oxide, and/or a layer stack with combinations thereof. For instance, an ITO/Ag/ITO stack may be used in certain example embodiments.

Figure 46:
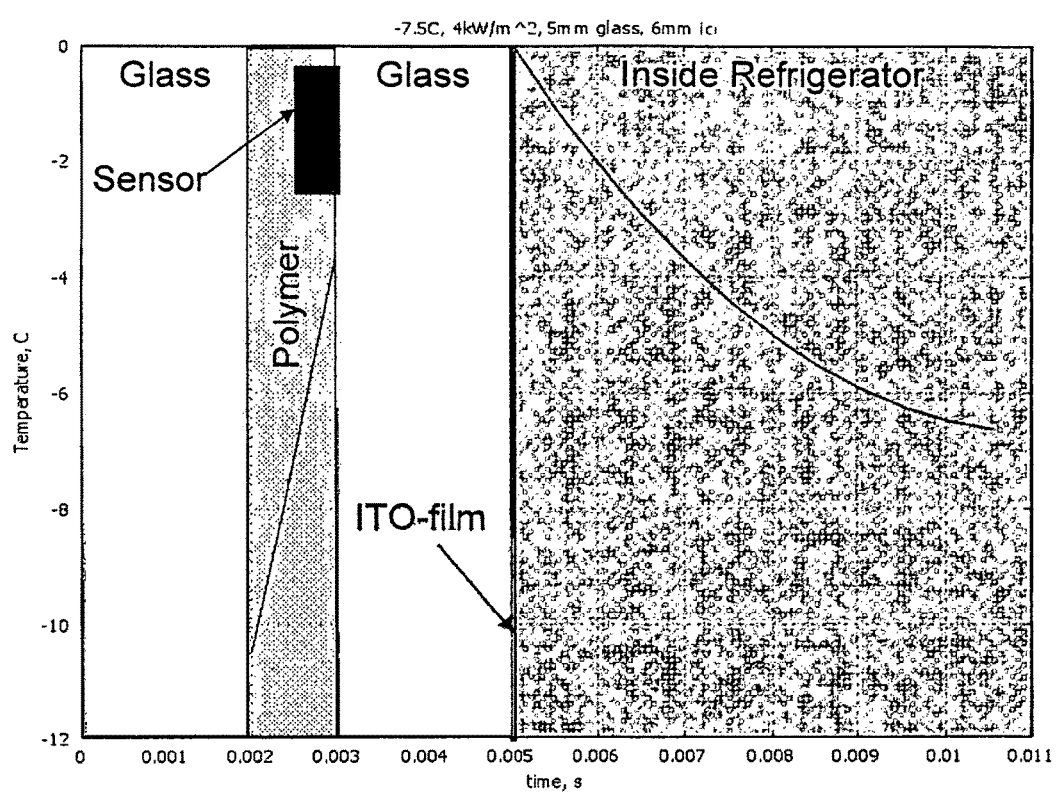
FIG. 46 is a graph plotting the temperature gradient of an example laminated article according to an example embodiment.

FIG. 46 is a graph plotting the temperature gradient of an example laminated article according to an example embodiment. The TCC in the FIG. 46 embodiment is ITO and is disposed on an outer surface of the inner glass substrate. As can be seen, the inner substrate heats very quickly and to the highest levels, thereby helping to reduce the incidence of moisture, ice, and/or other forms of condensation.

Figure 47:
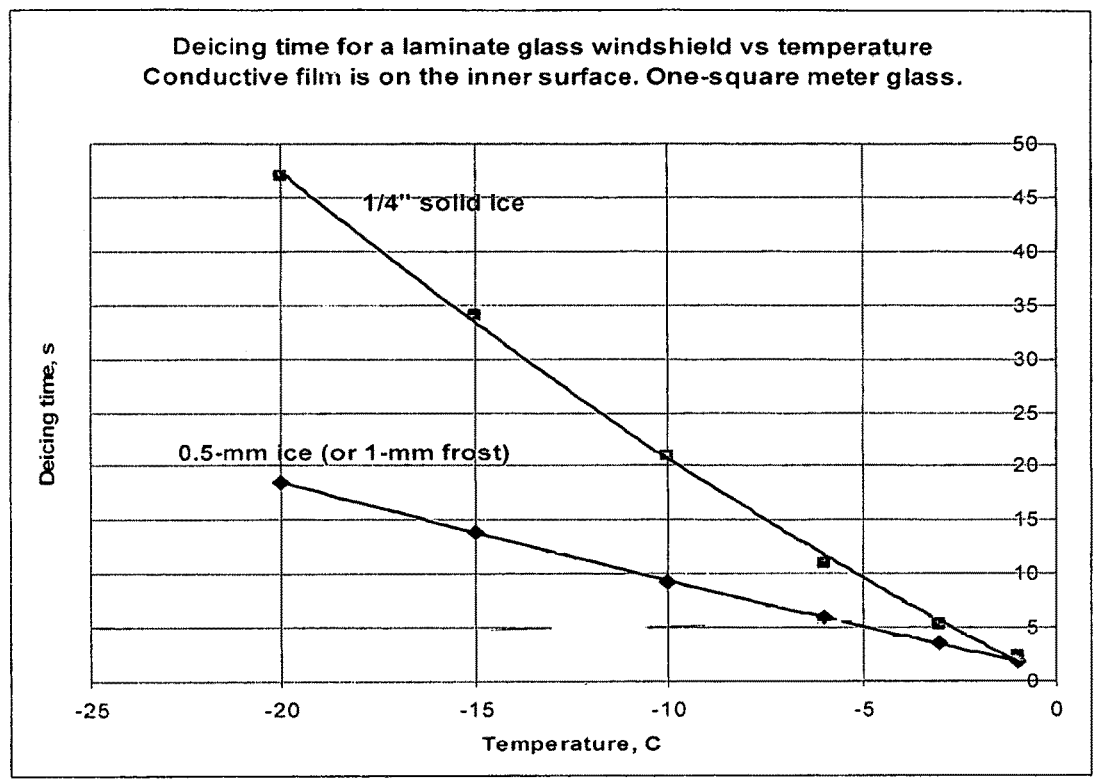
FIG. 47 is a graph plotting the deicing time for an illustrative laminated article vs. temperature according to an example embodiment.

FIG. 47 is a graph plotting the deicing time for an illustrative laminated article vs. temperature according to an example embodiment. Of course, a perhaps more likely scenario for merchandisers involves 0.5 mm of ice or 1 mm of frost, which line would fall between the two extremes in FIG. 47. In any event, the fast deicing time for solid ice demonstrates that the example arrangements described herein are suitable for merchandisers and the perhaps more harsh environments that many vehicle windshields, mirrors, commercial or residential windows, and/or the like may encounter. Thus, it will be appreciated that the example detection and pulsed heating techniques described herein may be used in connection with other applications including, for example, vehicle windshields, mirrors, commercial or residential windows, and/or the like.

Figure 48:
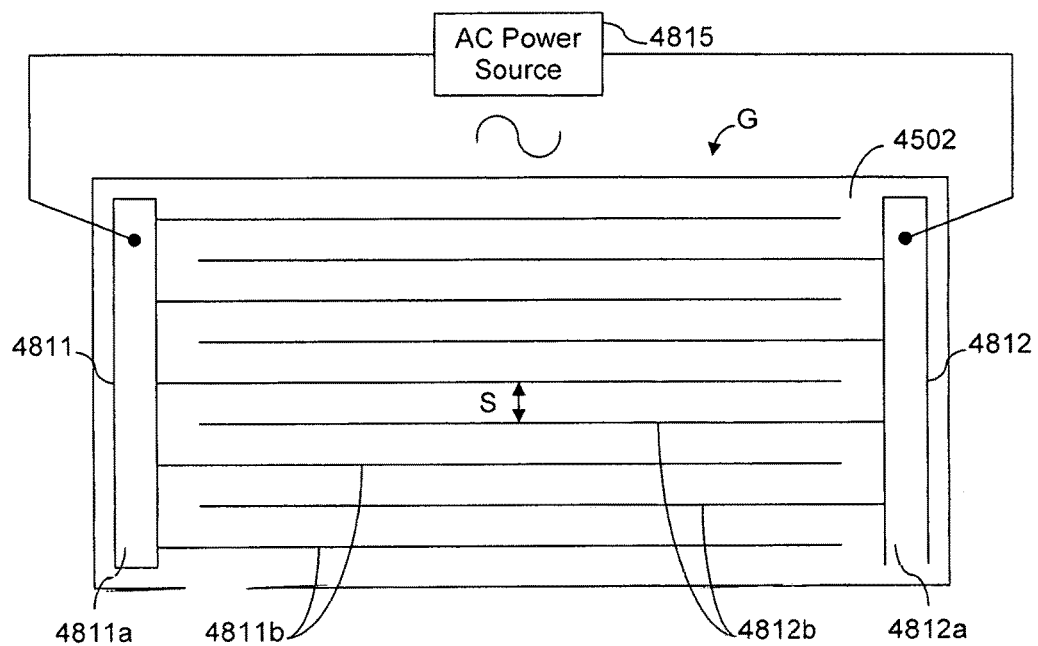
FIG. 48 illustrates an illustrative conductive grid G formed by the interspersed conductors (or electrodes) formed on the interior surface of a glass substrate suitable for use with the pulsed heating techniques of certain example embodiments.

Example pulsed heating techniques are disclosed, for example, in U.S. Pat. No. 7,518,093, the entire contents of which are hereby incorporated herein by reference. When such techniques are employed, the TCC may be disposed in a pattern including lines and/or a grid. FIG. 48 illustrates that the conductive grid G formed by the interspersed conductors (or electrodes) 4811 and 4812 is formed on the interior surface of a glass substrate in the door. The FIG. 48 example includes comb-shaped conductors 4811 and 4812, which include conductive bus bars 4811a and 4812a, respectively. The comb-shaped conductors 4811 and 4812 further include conductive comb teeth 4811b and 4812b, respectively, which extend across a viewing area of the window from the bus bars. The conductors (or electrodes) 4811 and 4812 may be provided directly on and contacting the surface of the glass substrate 4502. From AC power source 4815, AC tuned to an ice removal frequency is caused to run through the electrode(s) 4811 and/or 4812. In accordance with the laws of physics (e.g., Maxwell's Equations), the passing of the AC through the conductors 4811, 4812 causes electromagnetic fields to be generated. The electromagnetic fields generated by the AC passing through the conductive structure propagate through the glass substrate and encompass and/or reach an exterior surface of the substrate and can be absorbed by ice, thereby causing the ice to melt and/or be removed from the window. Differently stated, once the de-icing circuit is driven with AC, electromagnetic energy from the circuit is coupled to ice on the exterior surface of the door. This electromagnetic energy is absorbed by the ice, thereby causing ice removal from the window via melting and/or delamination.

In certain example embodiments of this invention, the ice-removal structure allows the impedance of the circuit to be tuned so that only, or substantially only, when ice is present the circuit becomes lossy and dissipates energy to the ice; but otherwise the circuit resonates. Thus, the circuit may be termed an ice-induced lossy circuit which is not significantly lossy when ice is not present on the exterior surface of the window. This is advantageous in that power consumption may be made more efficient.

In certain example embodiments, it has been found that an AC frequency from the power source 4815 tuned to ice removal is from about 5-40 kHz, more preferably from about 10-25 kHz, and most preferably from about 10-20 kHz. It has surprisingly been found that the use of AC at this frequency causes generation of electromagnetic energy that is most efficiently absorbed by ice on the exterior surface of the door, thereby resulting in the most efficient ice removal. A sine wave and/or square wave type of AC may be used in different example embodiments. In certain example embodiments, a pulsing technique used may be the so called chirping mode whereby a sinusoidal wave is modulated by square pulses. In certain example embodiments, it has also been found that application of such AC at about 300-500 V is particularly effective at ice removal.

In certain example embodiments, the pattern or grid may be formed by first depositing a continuous conductive layer of Ag, Cr, Au, ITO, or the like on the glass substrate. Layer stacks of these and/or other materials also may be used (e.g., an ITO/Ag/ITO layer stack may be used). The conductive layer can then be laser scribed into the two conductors (e.g., at the peripheral edges of the substrate) with a spatial frequency such that line widths (e.g., the width of comb teeth) may be no larger than about 200 µm, more preferably no larger than about 100 µm, in certain example embodiments. Such a gridded system would be difficult to be seen by the naked eye and may even appear transparent to a vehicle operator or one exterior the vehicle. In certain example embodiments, the spacing S between adjacent approximately parallel conductive grid members may be from about 100 to 800 µm, more preferably from about 100 to 500 µm, and sometimes from about 125 to 250 µm.

The AC is put into the conductive material, with resistive and capacitive components. Although the example is given for ice, the frequency of the AC can be matched to the loss function of water, fog, condensation, etc. An ultra-low frequency AC may be provided so as to act like a pulse function, decomposing into a sequence of sine or square waves with fundamental harmonics, that help dissipate the ice, water, fog, condensation, etc. Thus, the example pulsed heating techniques described herein may be extended for use with water, fog, condensation, etc.

Although certain example embodiments have been described in connection with refrigerator doors, the techniques described herein may be applied to other structures. For example, the techniques of certain example embodiments may be applied to freezer doors, etc. Such applications may be horizontally oriented, vertically oriented, etc. Furthermore, the example embodiments described herein may be used in connection with so-called active heating/defogging/defrosting applications, applications where thin film layer stacks are provided to provide low hemispherical emissivity coatings in connection with more passive solutions, etc. See, for example, U.S. Publication Nos. 2011/0212279 and 2010/0209730, as well as U.S. application Ser. No. 12/923,953, filed on Oct. 15, 2010, the entire contents of each of which are hereby incorporated herein by reference.

Regardless of the end application in which the example sensors described herein are used, Bayesian inferences may be made as to the various excitations in order to help predict the likelihood of a current or future excitations and, thus, to help improve the quality of the sensing. The source of a disturbance may be of any number of possible origins including, for example, water (e.g., as in film-wise or drop-wise condensation), human or other touch, visible and IR light, EMI, etc. These disturbances affect the capacitive sensor field (EFS) and/or light detector's incoming flux. Each of these sources of disturbances may be fingerprinted as a model "M" with their respective parameterization. Certain example embodiments that implement a Bayesian approach assume that M represents a model as well as its parameterization, I is the background information and any underlying information about data retrieval and applicability of the model, and D is data (experimental and/or numerical) that may be used to improve the knowledge of the suitability of the model M.

In certain example embodiments, the algorithm may begin with an a priori probability of M based on the background information or evidence I given to it at the outset. It may then set out to re-compute this probability as new evidence "D" streams in from the sensor. The algorithm may perform computations to determine which model M best represents the disturbances being sensed. Example computations follow in the description below.

The algorithm may compute the probability P(M|D,I) based on the evidence of new data D by using the fact that the latter quantity is proportional to the product of the prior probability distribution and the maximum likelihood distribution. This sort of calculation follows from Laplace's treatise on inductive logic on the principle of inverse probability, and Bayes' theorem.

The algorithm may represent the process by which the sensor "learns" from experience. It starts out with the probability of M based on the background information I [P(M|I)]. As time goes, it is given new evidence in the form of new data stream D. This theorem tells our sensor how to re-compute and update the probability of the model M [P(M|D,I)]. The degree of truth of the model M is quantified by the probability as data is collected by the system. It repeats this process over and over again. As a result, certain example embodiments may use the condensation and/or light sensors to perform such computations and re-computations quickly using the principle of correlation functions. In certain example embodiments, it is possible to discriminate with a high certainty between various models. In certain example embodiments, the level of certainty is greater than 90%, preferably greater than 95%, still more preferably higher than 99%.

Certain example embodiments look for a plausible reason to admit a given model M based on the evidence of data. Bayes' theorem can be used to effectively update the current state of knowledge about M after arrival of some data set D. More particularly, P(M|D,I)=P(M|I)P(D|M,I)/P(D|I).

P(M|I) is known as the prior distribution, and expresses the state of knowledge about M prior to the arrival of data. P(D|M,I) is termed the likelihood function when considered as a function of M. It is known as the sampling function when considered as a function of D. P(M|D,I) is the complete solution to the inference problem. P(D|I) is the evidence.

One advantage of using a probabilistic approach is that the sensors of certain example embodiments can make the best of whatever information of the outside world that it senses. For instance, the data stream that it registers (e.g., frame-to-frame) allows it to make very fast decisions about which model best characterizes the situation.

By way of illustration, consider a single point source (disturbance) that causes a disturbance in the capacitive field with intensity Q and located at position r and intensity $q_s$. These source properties can be encoded as a vector $q_s$=([C], L), where [C] is an array that constitutes a frame.

$$Q=q_s\delta(x-x_s)[H(t-t_{on})-H(t-t_{off})]$$

Detectors measuring or sensing the disturbances in the electric field may be arranged in the glass door of a refrigerator/freezer unit, in the windshield, or elsewhere in other applications. The source creates disturbances in the electric field, which are quasi-stationary.

Consider first a single disturbance source defined by the parameters m from model M. The process is not yet concerned with calculating the evidence term. Furthermore, by using the Markov Chain Monte Carlo (MCMC) method or the like, it is possible to draw samples from the posterior probability density function (PDF) without knowing the normalization constant. This allows for a simplified version of the equation to be used, namely, P(m|d,I)=P(m|I)P(d|m,I), where d represents the capacitive field data measured by the array of detectors. Pseudo-code for the Hamiltonian Markov Chain Algorithm is provided in FIG. 49.

Given that the source of the disturbance is described by the parameters m, there is a probability that an array of detectors will observe a certain set of capacitance C and light intensity values I. The likelihood function may be used to quantify the probability of the discrepancy between the measured (C, I) and the corresponding set of modeled ($C_s$, $I_s$), termed as the theoretical source-sensor relationship. For simplicity, in this example, denote d=(C, I) and z=($C_s$, $I_s$).

The measured value denoted by the $i^{th}$ detector is $d_i$. $z_i$ is the value that the $i^{th}$ detector would theoretically measure if the source were characterized correctly by the parameters of model m. The discrepancy between the measured and modeled concentration at the $i^{th}$ detector $d_i$ and $z_i$ arises from two main sources of error, namely, measurement error and model error.

In an example case, $<d_i>=d_i^{true}+e_i^{meas}$, where $d_i^{true}$ is the true unknown value of the mean capacitance and light intensity measurement and $e_i^{meas}$ is the measured error. The noise may be assumed normal in certain example embodiments, although other distributions can be used in other example embodiments. Similarly, $<z_i>=z_i^{true}+e_i^{mod}$, where $e_i^{mod}$ is the modeled error.

The measurement error is then given by:

$$P(d \mid d^{true}, m, I) \propto \exp\left[-\frac{1}{2}\sum_i \frac{(d_i - d_i^{true})^2}{\sigma_{D,i}^2}\right] \quad (i)$$

The model error is given by:

$$P(d^{true}, m, I) \propto \exp\left[-\frac{1}{2}\sum_i \frac{(d_1 - r_i(m))^2}{\sigma_{R,i}^2}\right] \quad (ii)$$

This states that the probability that the true data is predicted by the model for the disturbance-detector relationship when the source parameters are m. The likelihood is then obtained by the joint PDF:

$$P(d \mid m, I) = \int_{all\ d^{true}} P(d, d^{true} \mid m, I) dd^{true}$$

$$= \int_{all\ d^{true}} P(d \mid d^{true}, m, I) P(d^{true}, m, I) dd^{true}$$

Thus, the posterior is given by joint PDF:

$$P(m \mid d, I) \propto I(m \in \Omega) \exp\left[-\frac{1}{2}\sum_{i,j} \frac{(d_i^{(j)} - r_i^{(j)}(m))^2}{\sigma_{D,i,j}^2 + \sigma_{R,i,j}^2}\right].$$

Thus, $$P(m \mid d, I) \propto P(m \mid I) P(d \mid m, I) \propto I(m \in \Omega) \exp\left[-\frac{1}{2} \sum_{i,j} \frac{(d_i - r_i(m))^2}{\sigma_{D,i}^2 + \sigma_{R,i}^2}\right]$$

This is because:

$$r_i^{(j)}(m) = q_s \int_{on}^{min(l_j^{(j)}, t_{off})} C_i^{*(j)}(x_s, t_s) dt_s.$$

Figure 50:
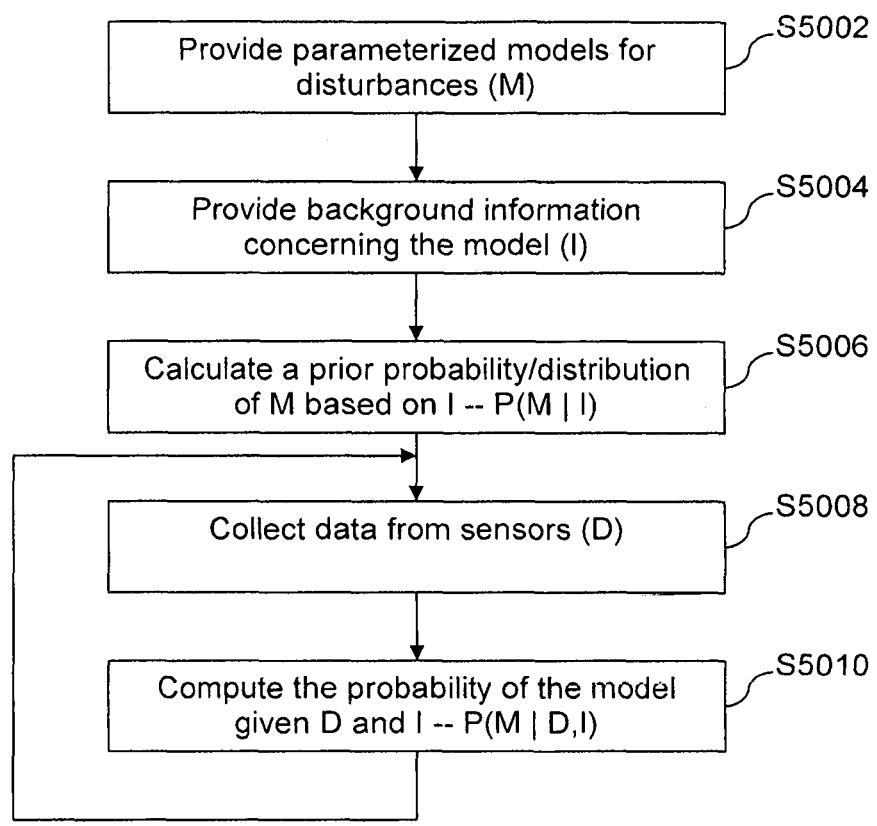
FIG. 50 is an illustrative flowchart illustrating how Bayesian techniques may be used to improve the quality of detections according to an example embodiment.

FIG. 50 is an illustrative flowchart illustrating how Bayesian techniques may be used to improve the quality of detections according to an example embodiment. In step S5002, parameterized models (M) for disturbances are provided. As indicated above, the disturbances may be, for example, formation of ice or condensation, human touch, EMI, etc. These models may be fingerprinted, e.g., as discussed above. In step S5004, background information concerning the model (I) is provided. The prior probability or prior distribution of the model (M) based on the background information (I) is calculated, e.g., according to P(M|I). Data (D) is collected from the sensors in step S5006. This may be accomplished using the capacitive moisture sensors and/or light sensors described above, e.g., to sense disturbances in the electric field for a given frame or area of interest (for instance, on the refrigerator/freezer door, windshield, etc.). The disturbances may be simplified or represented one or more point source disturbances having a position and intensity. In step S5008, the probability of the model (M) given the data (D) and the background information (I) may be computed. This calculation may be facilitated by recognizing that the data (D) is sometimes proportional to the product of prior probability distribution and the maximum likelihood distribution. In other words, P(M|D,I) may be calculated as P(M|I) P(D|M,I)/P(D|I), where P(M|I) is the prior distribution, P(D|M,I) is the likelihood function when considered as a function of M, and P(D|I) is the evidence. The computation may be repeated as more and more data (D) streams in. In certain example embodiments, as the process progresses, the background information (I) may be updated based on the recently received data (D).

In certain example embodiments, a model may be accepted or rejected based on the probability calculation and, for example, whether the probability meets or exceeds a predetermined threshold value. For instance, a model may be accepted once its likelihood is greater than or equal to 90%, more preferably greater than or equal to 95%, and sometimes even greater than or equal to 99%. Once a particular model is accepted, an appropriate action may be triggered. For instance, a vehicle's windshield wipers may be actuated or defroster activated, a merchandiser's door may be actively heated (e.g., using the pulsed heating techniques described above), etc. Alternatively, once a particular model is accepted, no action may be taken. For instance, a vehicle's windshield wipers may continue to function or not function if the windshield is touched or comes into contact with dirt or debris, a merchandiser's door may not be heated in the presence of EMI, etc.

As alluded to above, there are a number of different applications that could benefit from the Bayesian techniques described herein. Of course, it will be appreciated that the different applications may involve different data being used to accept or reject different models. One example application applies to merchandiser (e.g., refrigerator/freezer) apparatuses. As will be appreciated from the discussion above, a moisture and/or condensation sensor could be used to trigger selective heating (e.g., through the pulses, as described above). These techniques could in some cases be further improved by providing the example Bayesian analysis disclosed herein, but in yet further ways. For example, it has been discovered that the combination of the example Bayesian analysis disclosed herein and the example condensation detectors disclosed herein can be used to effectively pre-emptively trigger defogging, even before a door is opened. In essence, capacitive arrays as disclosed herein may be used as proximity sensors, e.g., to determine when people are nearby the products, when they approach products, when the place their hands on merchandiser door handles or the like, etc. The example Bayesian analysis techniques disclosed herein essentially offer a learning system that serves as a rough proximity sensor, triggers a few pulses as a person's hand approaches a door and/or touches a handle, and then continues to pulse as the door is opened, thereby removing beaded water, condensation, and/or the like more efficiently than otherwise might be possible (e.g., in connection with active approaches, approaches that rely on mechanical open/close switches, etc.).

This approach is at least partially enabled by using Bayesian techniques to differentiate situations where a person is merely walking by a suitably configured merchandizers, from situations where a person is approaching and likely to open the door. This differentiation can be used to start heating (e.g., via pulsing at one or more appropriate frequencies) at a time sufficiently early to make sure that too much heat is not being introduced into the merchandiser, while still ensuring that the door remains hot enough to ensure that condensation will not be formed if/when the door is opened. In so doing, condensation does not have a chance to form. The learning system also over time reduces the likelihood of "false positives," which might correspond, for example, to the system thinking that the door might be opened and triggering the heating unnecessarily, thereby consuming power and introducing heat into the cooled merchandiser.

In certain example embodiments, capacitive array "fingerprints" are developed for a person or persons walking by a merchandiser, a person or persons approaching a merchandiser, a person moving his/her hand towards a door, a person placing his/her hand on a door or handle of the door to open it, etc. This information may be supplied as background information to the Bayesian system. Further data may be gathered, contrasting this a priori data with actual usage patterns of real consumers. For example, thus, the model may be refined over time as the system observes and thus gathers data concerning consumers walking by, approaching, and interacting with doors to merchandisers. Further refinements may be made over time as yet further data is gathered concerning the time between a consumer's approach and actual opening of the merchandiser, how much time and/or energy it takes to remove condensation, how early to start the heating to ensure that condensation does not have a chance to build up on an opened door, etc.

In certain example embodiments, at least one processor may be configured to execute instructions corresponding to the example method steps described above. In certain example embodiments, such instructions may be provided in a program stored on a non-transitory computer readable storage medium for subsequent execution.

"Peripheral" and "edge" seals herein do not mean that the seals are located at the absolute periphery or edge of the unit, but instead mean that the seal is at least partially located at or near (e.g., within about two inches) an edge of at least one substrate of the unit. Likewise, "edge" as used herein is not limited to the absolute edge of a glass substrate but also may include an area at or near (e.g., within about two inches) of an absolute edge of the substrate(s).

As used herein, the terms "on," "supported by," and the like should not be interpreted to mean that two elements are directly adjacent to one another unless explicitly stated. In other words, a first layer may be said to be "on" or "supported by" a second layer, even if there are one or more layers therebetween.

In certain example embodiments, there is provided a method of detecting moisture on a glass substrate. The method comprises: providing a parameterized model (M) for a possible moisture-related disturbance; providing background information (I) concerning the model, I being known a priori; calculating a prior probability of M given I, P(M|I); collecting data from at least one sensor (D) connected to the substrate; computing a probability of the model given D and I, P(M|D,I); repeating the computing of P(M|D,I) as additional data is collected; and accepting the model if P(M|D,I) is greater than 0.9, and otherwise rejecting the model. The glass substrate is a part of a vehicle window, building window, or merchandiser.

In addition to the features of the previous paragraph, in certain example embodiments, the at least one sensor may be configured to sense disturbances in an electric field proximate the substrate for a given frame in time.

In addition to the features of the previous paragraph, in certain example embodiments, the data for each frame may be simplified to point source disturbances having position and intensity values.

In addition to the features of any of the three previous paragraphs, in certain example embodiments, D may be proportional to the product of a prior probability distribution and a maximum likelihood distribution.

In addition to the features of any of the four previous paragraphs, in certain example embodiments, P(M|D,I) is calculated as P(M|I)P(D|M,I)/P(D|I), where: P(M|I) is a prior distribution, P(D|M,I) is a likelihood function when considered as a function of M, and P(D|I) is evidence.

In addition to the features of any of the five previous paragraphs, in certain example embodiments, the at least one sensor may include a capacitive sensor configured to measure a disturbance in the capacitive field set up by the sensor, the capacitive field having different detected intensities at different positions in the field.

In addition to the features of any of the six previous paragraphs, in certain example embodiments, the at least one sensor may include a light sensor.

In addition to the features of any of the seven previous paragraphs, in certain example embodiments, a heater may be activated if the model is accepted, so as to facilitate removal of condensation on the substrate.

In certain example embodiments, there is provided a method of detecting moisture on a glass substrate. The method comprises: providing a plurality of parameterized models (Mx) for different possible disturbances; providing background information (Ix) concerning each of the models; calculating a prior probability of Mx given Ix, P(Mx|Ix); collecting data from at least one sensor (D) connected to the substrate; computing a probability of each said model given D and Ix, P(Mx|D,Ix); repeating the computing of P(Mx|D,Ix) as additional data is collected; comparing the probability of each said model to a predetermined threshold; accepting or rejecting each said model based on the comparing; and when a particular model is accepted, causing an action to be taken relative to the glass substrate in dependence on the particular model that is accepted.

In addition to the features of the previous paragraph, in certain example embodiments, parameterized models may be provided for moisture-related disturbances and/or non-moisture-related disturbances.

In addition to the features of the previous paragraph, in certain example embodiments, the moisture-related disturbances may include the presence of liquid condensation, frost, and/or ice.

In addition to the features of the either of the two previous paragraphs, in certain example embodiments, the non-moisture-related disturbances may include EMI and/or human touch.

In addition to the features of any of the four previous paragraphs, in certain example embodiments, the substrate may be a part of a vehicle window built into a vehicle, and the action may includes actuating windshield wipers of the vehicle and/or turning on a defroster of the vehicle; and/or the substrate may be a part of a refrigerator/freezer merchandiser, and the action may include heating at least the substrate.

In certain example embodiments, there is provided a non-transitory computer readable storage medium tangibly storing instructions that, when executed by at least one processor, perform a method according to any one of the thirteen previous paragraphs.

In certain example embodiments, there is provided an electronic device located in close relative proximity to a glass substrate. A first memory location stores a plurality of parameterized models (Mx) for different possible disturbances. A second memory location stores background information (Ix) concerning each of the models. At least one sensor is configured to collect data from at least one sensor (D) connected to the substrate. At least one processor is configured to: calculate a prior probability of Mx given Ix, P(Mx|Ix); compute a probability of each said model given D and Ix, P(Mx|D,Ix); repeat computations of P(Mx|D,Ix) as additional data is collected by the at least one sensor; compare the probability of each said model to a predetermined threshold; and accept or reject each said model based on the comparison.

In addition to the features of the previous paragraph, in certain example embodiments, parameterized models may be stored for moisture-related disturbances and/or non-moisture-related disturbances.

In addition to the features of the previous paragraph, in certain example embodiments, the moisture-related disturbances may include the presence of liquid condensation, frost, and ice, and/or the non-moisture-related disturbances may include EMI and human touch.

In addition to the features of any of the three previous paragraphs, in certain example embodiments, the at least one processor may be further configured to cause an action to be taken in respect of the glass substrate when a particular model is accepted, the action to be taken being selected based on the particular model that is accepted.

Certain example embodiments may relate to a vehicle comprising the device of the previous paragraph, for example, with the glass substrate potentially being at least a part of a vehicle windshield, and with the action to be taken potentially being selected from the group consisting of turning on/off windshield wipers, turning on/off defrosters, and turning on/off the vehicle's lights. Alternatively, certain example embodiments may relate to a merchandiser comprising the device of the previous paragraph, for example, with the glass substrate potentially being at least a part of a door to the merchandiser, and with the action to be taken potentially including turning on/off a heater so as to facilitate removal of condensate built up on the door.

While the invention has been described in connection with what is presently considered to be the most practical and preferred embodiment, it is to be understood that the invention Is not to be limited to the disclosed embodiment, but on the contrary, is intended to cover various modifications and equivalent arrangements included within the spirit and scope of the appended claims.

What is claimed is:

1. A method of detecting moisture on a glass substrate, the method comprising:
    providing a parameterized model (M) for a possible moisture-related disturbance;
    providing background information (I) concerning the model;
    calculating a prior probability of M given I, P(M|I);
    collecting data from at least one sensor (D) connected to the substrate;
    computing a probability of the model given D and I, P(M|D,I);
    repeating the computing of P(M|D,I) as additional data is collected; and
    accepting the model if P(M|D,I) meets and/or exceeds a predetermined threshold,
    wherein the glass substrate is a part of a vehicle window, building window, or merchandiser window; and
    wherein acceptance of the model triggers an action to be taken relative to the glass substrate, the action being selected from the group consisting of: (i) causing a wiper to remove moisture from a vehicle window, (ii) heating the glass substrate, and (iii) defrosting the glass substrate.

2. The method of claim 1, wherein the at least one sensor is configured to sense disturbances in an electric field proximate the substrate for a given frame in time.

3. The method of claim 1, wherein D is proportional to the product of a prior probability distribution and a maximum likelihood distribution.

4. The method of claim 1, wherein P(M|D,I) is P(M|I) P(D|M,I)/P(D|I), where:
    P(M|I) is a prior distribution,
    P(D|M,I) is a likelihood function when considered as a function of M, and
    P(D|I) is evidence.

5. The method of claim 1, wherein the at least one sensor includes a capacitive sensor configured to measure a disturbance in the capacitive field set up by the sensor, the capacitive field having different detected intensities at different positions in the field.

6. The method of claim 1, wherein the at least one sensor includes a light sensor.

7. The method of claim 1, further comprising activating a heater when the model is accepted, so as to facilitate removal of condensation on the substrate.

8. A method of detecting moisture on a glass substrate, the method comprising:
    providing a plurality of parameterized models (Mx) for different possible disturbances;
    providing background information (Ix);
    calculating a prior probability of Mx given Ix, P(Mx|Ix);
    collecting data from at least one sensor (D) connected to the substrate;
    computing a probability of each said model given D and Ix, P(Mx|D,Ix);
    repeating the computing of P(Mx|D,Ix) as additional data is collected;
    comparing the probability of each said model to a predetermined threshold;
    accepting or rejecting each said model based on the comparing; and
    when a particular model is accepted, causing an action to be taken relative to the glass substrate in dependence on the particular model that is accepted, the action being one or more of: (i) causing a wiper to activate for wiping a vehicle window, (ii) heating the glass substrate, (iii) defrosting the glass substrate, and (iv) turning on or off vehicle lights.

9. The method of claim 8, wherein parameterized models are provided for moisture-related disturbances.

10. The method of claim 8, wherein the moisture-related disturbances include the presence of liquid condensation, frost, and ice.

11. An electronic device for detecting moisture on a glass substrate, the electronic device comprising:
    a first memory storing a plurality of parameterized models (Mx) for different possible disturbances;
    a second memory storing background information (Ix);
    at least one sensor configured to collect data from at least one sensor (D); and
    at least one processor configured to:
        calculate a prior probability of Mx given Ix, P(Mx|Ix);
        compute a probability of each said model given D and Ix, P(Mx|D,Ix);
        repeat computations of P(Mx|D,Ix) as additional data is collected by the at least one sensor;
        compare the probability of each said model to a predetermined threshold; and
        accept or reject each said model based on the comparison, wherein acceptance of a model triggers an action to be taken relative to the glass substrate, the action being one or more of: (i) activating a wiper for wiping a vehicle window, (ii) heating the glass substrate, (iii) defrosting the glass substrate, and (iv) turning on or off vehicle lights.

* * * * *